(12) United States Patent
Wengreen et al.

(10) Patent No.: US 9,814,651 B2
(45) Date of Patent: Nov. 14, 2017

(54) STORAGE SYSTEMS AND METHODS FOR MEDICINES

(71) Applicants: Sandy Wengreen, Sammamish, WA (US); Eric John Wengreen, Sammamish, WA (US)

(72) Inventors: Sandy Wengreen, Sammamish, WA (US); Eric John Wengreen, Sammamish, WA (US)

(*) Notice: Subject to any disclaimer, the term of this patent is extended or adjusted under 35 U.S.C. 154(b) by 57 days.

(21) Appl. No.: 15/172,152

(22) Filed: Jun. 3, 2016

(65) Prior Publication Data

US 2016/0279029 A1    Sep. 29, 2016

Related U.S. Application Data

(63) Continuation-in-part of application No. 14/849,884, filed on Sep. 10, 2015, now Pat. No. 9,707,156, which
(Continued)

(51) Int. Cl.
| | |
|---|---|
| *F25D 25/00* | (2006.01) |
| *A61J 1/16* | (2006.01) |
| *B65B 63/08* | (2006.01) |
| *A61M 5/00* | (2006.01) |
| *A61J 1/18* | (2006.01) |
| *B65D 81/38* | (2006.01) |

(Continued)

(52) U.S. Cl.
CPC .............. *A61J 1/165* (2013.01); *A61J 1/1412* (2013.01); *A61J 1/18* (2013.01); *A61M 5/002* (2013.01); *B65B 63/08* (2013.01); *B65D 81/383* (2013.01); *F25D 3/00* (2013.01); *F25D 3/08* (2013.01); *A61J 1/1418* (2015.05); *A61J 2200/40* (2013.01); *A61J 2200/50* (2013.01); *A61J 2200/72* (2013.01); *A61J 2205/70* (2013.01); *A61M 2005/3125* (2013.01); *A61M 2205/127* (2013.01); *A61M 2205/3368* (2013.01); *A61M 2205/3633* (2013.01); *A61M 2205/8206* (2013.01); *F25D 2303/085* (2013.01); *F25D 2303/0843* (2013.01); *F25D 2303/08222* (2013.01)

(58) Field of Classification Search
CPC ................. F25D 3/10; F25D 2331/804; F25D 2303/0822
USPC ........................ 62/62, 371, 457.1, 457.2, 530
See application file for complete search history.

(56) References Cited

U.S. PATENT DOCUMENTS

| | | |
|---|---|---|
| 2,263,865 A | 11/1941 | Lewis |
| 3,034,845 A | 5/1962 | Haumann |
| | (Continued) | |

OTHER PUBLICATIONS

Wikipedia Article: "Phase Change Material," downloaded Feb. 5, 2015 from http://en.wikipedia.org/wiki/Phase-change_material.
(Continued)

*Primary Examiner* — Melvin Jones

(57) ABSTRACT

People can damage their medicines by taking them outside in hot or cold weather. On the other hand, some people need to carry their medicines with them wherever they go (even if the weather is extremely hot or cold). Specially constructed storage systems can protect medicines from damage due to hot and cold weather without requiring bulky structures or expensive components that consume electricity to regulate temperature.

21 Claims, 47 Drawing Sheets

Related U.S. Application Data is a continuation-in-part of application No. 14/616,652, filed on Feb. 6, 2015, now Pat. No. 9,151,531, application No. 15/172,152, filed on Jun. 3, 2016, which is a continuation-in-part of application No. 15/161,241, filed on May 21, 2016, which is a continuation-in-part of application No. 15/151,457, filed on May 10, 2016, which is a continuation of application No. 15/151,446, filed on May 10, 2016, application No. 15/172,152, which is a continuation-in-part of application No. 15/170,465, filed on Jun. 1, 2016.

(60) Provisional application No. 62/293,691, filed on Feb. 10, 2016.

(51) Int. Cl.
  *F25D 3/00* (2006.01)
  *F25D 3/08* (2006.01)
  *A61M 5/31* (2006.01)
  *A61J 1/14* (2006.01)

(56) References Cited

U.S. PATENT DOCUMENTS

| | | | |
|---|---|---|---|
| 3,401,692 A | 9/1968 | Harris | |
| 3,872,864 A | 3/1975 | Allen | |
| 3,910,441 A | 10/1975 | Bramming | |
| 3,961,720 A | 6/1976 | Potter | |
| 4,287,943 A | 9/1981 | Hotta | |
| 4,292,817 A * | 10/1981 | Loucks | A47J 41/00 62/372 |
| 4,323,066 A | 4/1982 | Bourdon | |
| 4,738,364 A | 4/1988 | Yeager | |
| 5,317,883 A | 6/1994 | Newman | |
| 5,330,810 A | 7/1994 | Nishino | |
| 5,390,791 A | 2/1995 | Yeager | |
| 5,435,142 A * | 7/1995 | Silber | B01L 3/508 422/939 |
| 5,531,255 A | 7/1996 | Vacca | |
| 5,615,772 A | 4/1997 | Naganuma | |
| 5,976,400 A | 11/1999 | Muffett | |
| 6,044,650 A * | 4/2000 | Cook | A61J 1/165 62/130 |
| 6,104,611 A | 8/2000 | Glover | |
| 6,336,340 B1 | 1/2002 | Laby | |
| 6,584,797 B1 | 7/2003 | Smith | |
| 6,634,417 B1 | 10/2003 | Kolowich | |
| 6,968,888 B2 | 11/2005 | Kolowich | |
| 7,041,123 B2 | 5/2006 | Stapf | |
| 7,059,387 B2 | 6/2006 | Kolowich | |
| 7,294,374 B2 | 11/2007 | Romero | |
| 7,328,583 B2 | 2/2008 | Hillman | |
| 7,412,846 B2 | 8/2008 | Sekiya | |
| 7,836,722 B2 | 11/2010 | Magill | |
| 7,908,870 B2 | 3/2011 | Williams | |
| 7,934,537 B2 | 5/2011 | Kolowich | |
| 8,074,465 B2 | 12/2011 | Heroux | |
| 8,096,975 B2 | 1/2012 | Lewis | |
| 8,205,468 B2 | 6/2012 | Hemminger | |
| 8,225,616 B2 | 7/2012 | Wilkinson | |
| 8,550,703 B2 | 10/2013 | Cutting | |
| 8,607,581 B2 | 12/2013 | Williams | |
| 9,151,531 B2 | 10/2015 | Wengreen | |
| 9,181,015 B2 | 11/2015 | Booska | |
| 9,707,156 B2 | 7/2017 | Wengreen | |
| 2003/0012701 A1 | 1/2003 | Sangha | |
| 2005/0016895 A1 | 1/2005 | Glenn | |
| 2005/0188714 A1 | 9/2005 | Wallace | |
| 2006/0191282 A1 | 8/2006 | Sekiya | |
| 2006/0271014 A1 | 11/2006 | Hynes | |
| 2007/0000484 A1 | 1/2007 | Magill | |
| 2007/0017533 A1 | 1/2007 | Wyrick | |
| 2007/0158325 A1 | 7/2007 | Cao | |
| 2007/0210090 A1 | 9/2007 | Sixt | |
| 2009/0078708 A1 | 3/2009 | Williams | |
| 2009/0230138 A1 | 9/2009 | Williams | |
| 2011/0155621 A1 | 6/2011 | Lindquist | |
| 2011/0207824 A1 | 8/2011 | Douleau | |
| 2012/0073312 A1 | 3/2012 | Cutting | |
| 2013/0025298 A1 | 1/2013 | Schryver | |
| 2013/0134347 A1 | 5/2013 | Edgar | |
| 2013/0221013 A1 | 8/2013 | Kolowich | |
| 2013/0255824 A1* | 10/2013 | Williams | B65D 81/18 141/1 |
| 2014/0259912 A1 | 9/2014 | Sutterlin | |
| 2014/0343493 A1 | 11/2014 | Wengreen | |
| 2015/0151893 A1 | 6/2015 | Wengreen | |
| 2016/0250101 A1 | 9/2016 | Wengreen | |
| 2016/0251140 A1 | 9/2016 | Wengreen | |
| 2016/0262979 A1 | 9/2016 | Wengreen | |
| 2016/0271015 A1 | 9/2016 | Wengreen | |
| 2016/0279029 A1 | 9/2016 | Wengreen | |

OTHER PUBLICATIONS

PureTemp: "About Entropy Solutions, Inc.," downloaded Feb. 5, 2015 from http://www.puretemp.com/stories/about-entropy-solutions-inc.

Fastcoexist.com Listing: "Passive Vaccine Storage Device," downloaded Aug. 15, 2013 from http://www.fastcoexist.com/1682578/this-bill-gates-backed-super-thermos-saves-lives-with-cold-vaccines.

Howstuffworks.com Article: "How Thermoses (Vacuum Flasks) Work," downloaded Jun. 14, 2013 from http://home.howstuffworks.com/thermos2.htm.

Wikipedia Article: "Epinephrine Autoinjector," downloaded Jun. 14, 2013 from http://en.wikipedia.org/wiki/Epinephrine_autoinjector.

Aliexpress.com Listing: "Retail Medicine Storage Product Mini EpiPen Fridge," downloaded Jun. 14, 2013 from http://www.aliexpress.com/item/Retail-medicine-storage-product-mini-epipen-fridge-maintains-the-inside-temperature-at-2-8-degreeC-CE/827311928.html.

Aliexpress.com Listing: "Pharmacy Product JYK-A Portable EpiPen Fridge," downloaded Jun. 14, 2013 from http://www.aliexpress.com/item/Pharmacy-product-JYK-A-Portable-epipen-fridge-AC-DC-li-battery-comes-with-16-5hrs-leading/723856846.html.

Amazon.com Listing: "Epinephrine-Mate Auto-Injector Carrying Case," downloaded Jun. 14, 2013 from http://www.amazon.com/EPInephrine-Mate-Auto-Injector-Carrying-Case/dp/B000VM9HGK.

Lindongroup.com Graphic: "Epinephrine-Mate Auto-Injector Carrying Case," downloaded Jun. 14, 2013 from http://www.lindongroup.com/uploads/images/Lindon%20Design/epinephrinemate%20package.jpg.

Omaxcare.com Listing: "LegBuddy," downloaded Jun. 14, 2013 from http://omaxcare.com/LegBuddy.html.

Amazon.com Listing: "AllerMates EpiPen & Allergy Medicine Carrying Case," downloaded Jun. 14, 2013 from http://www.amazon.com/AllerMates-Allergy-Medicine-Carrying-Squares/dp/B00CBLWMRA.

Esty.com Listing: "EpiPen Case Pouch," downloaded Jun. 14, 2013 from http://www.esty.com/listing/81915096/epi-pen-pouch-carrior-insulated.

Allergyapparel.com Listing: "AllerMates EpiPen Carrying Case," downloaded Jun. 17, 2014 from http://www.allergyapparel.com/AllerMates-EpiPen-Carrying-Case-allermates-epicase-blu-pnk.html.

EpiPen.com: "EpiPen.com FAQ," downloaded Jun. 14, 2013 from http://www.epipen.com/professionals/faq.

Ball Article: "How Beverage Cans are Made," downloaded Apr. 21, 2016 from www.ball-europe.com/Production-process-of-beverage-cans.htm.

PureTemp Article: "PCM Products," includes Vesl products, downloaded Apr. 21, 2016 from www.puretemp.com/stories/products.

(56) References Cited

OTHER PUBLICATIONS

Vesl: "TubeVesl," downloaded Apr. 21, 2016 from www.veslpcm.com/tubevesl/.
Vesl: "MatVesl," downloaded Apr. 21, 2016 from www.veslpcm.com/matvesl/.
Allergyapparel.com Listing: "Kool Blanket," downloaded Jun. 3, 2016 from www.allergyapparel.com/kool-blanket.
Frioinsulincoolingcase.com Listing: "Frio Case," downloaded Jun. 3, 2016 from www.frioinsulincoolingcase.com/media/FRIO%20Brochure.pdf.
Veta Smart Case, downloaded Oct. 19, 2016 from https://www.aterica.com/how-it-works.
"AnAPPhylaxis" Case, downloaded Oct. 19, 2016 from http://www.adanmi.com/anapphylaxis.
FlexiFreeze Medicine CooleRx, downloaded Oct. 31, 2016 from https://www.amazon.com/FlexiFreeze-FF0MC03-0MCBK-Medicine-CooleRx/dp/B001P30362/ref=sr_1_4?ie=UTF8&qid=1477930020&sr=8-4&keywords=FlexiFreeze.

\* cited by examiner 736 proximal retention member 736 proximal retention member 738 distal retention member 738 distal retention member

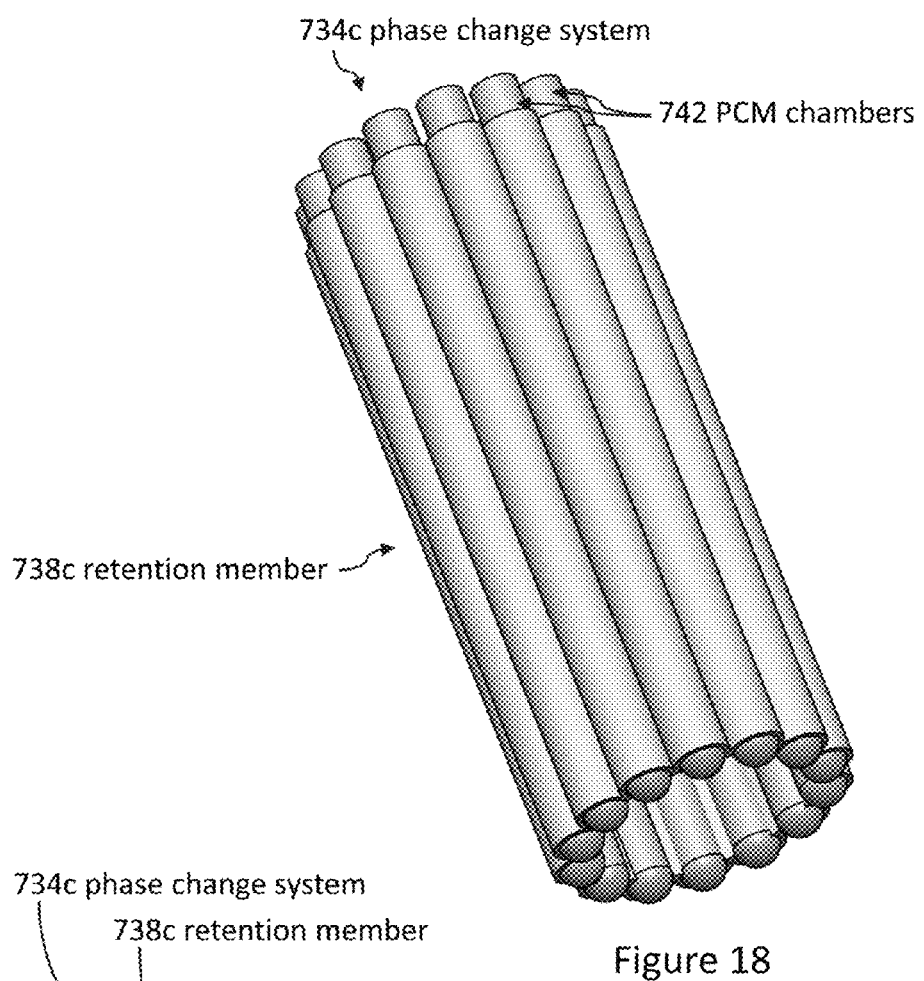
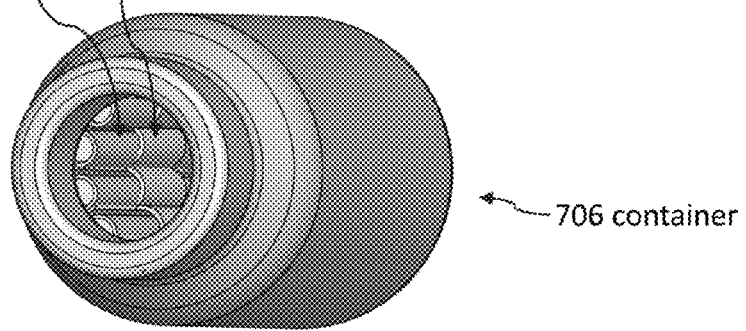
Figure 18
Figure 19

742e PCM chamber

742e PCM chamber 34  34

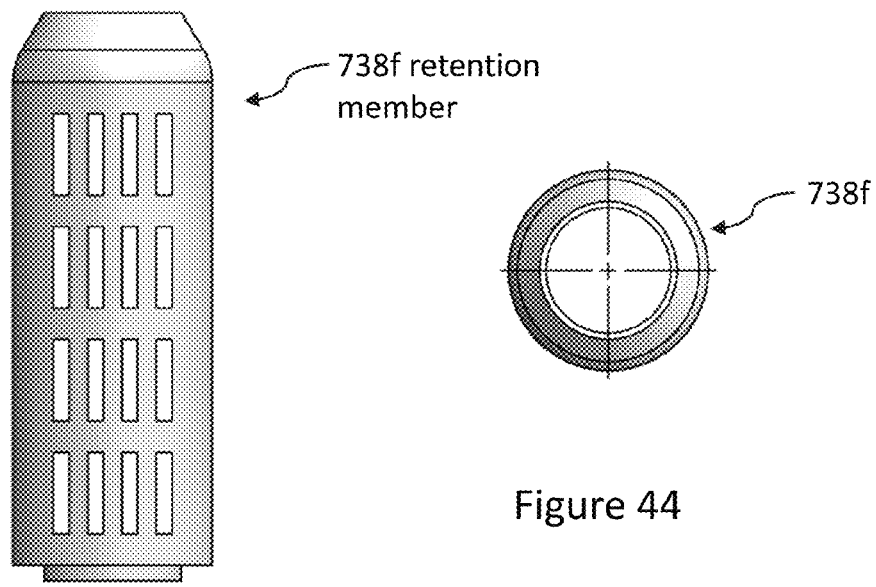
Figure 43
Figure 44
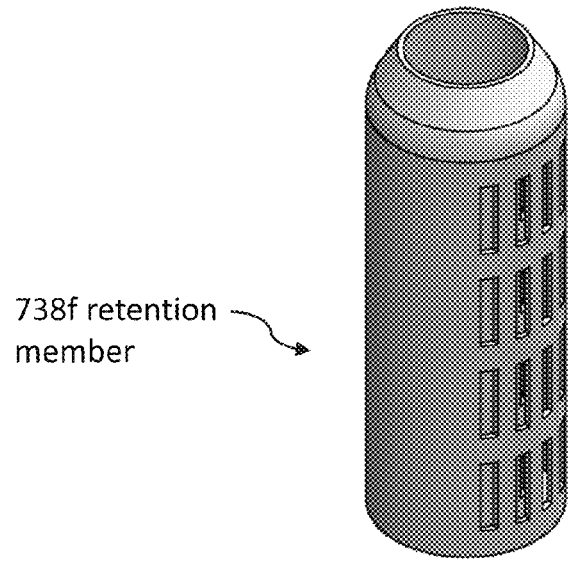
Figure 45

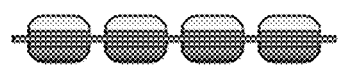
Figure 46
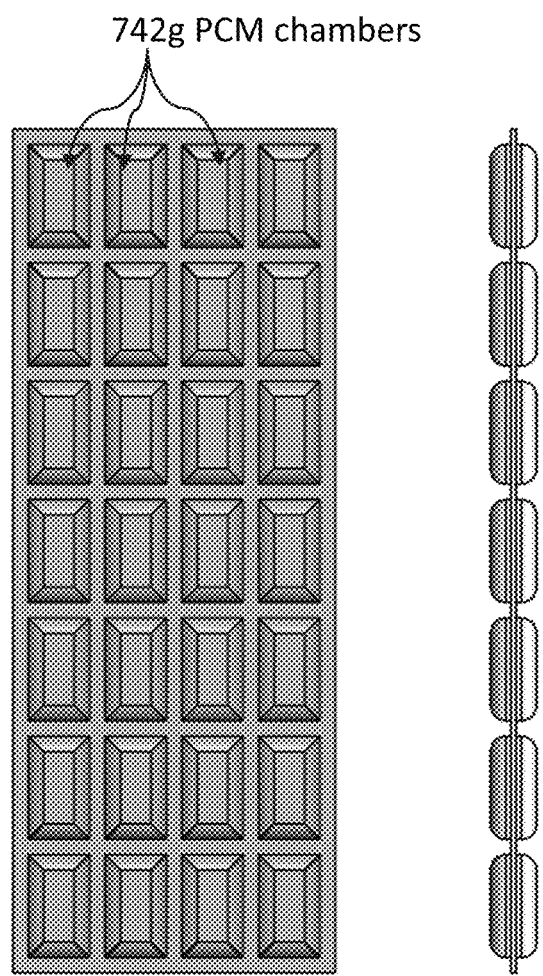
Figure 47  Figure 48

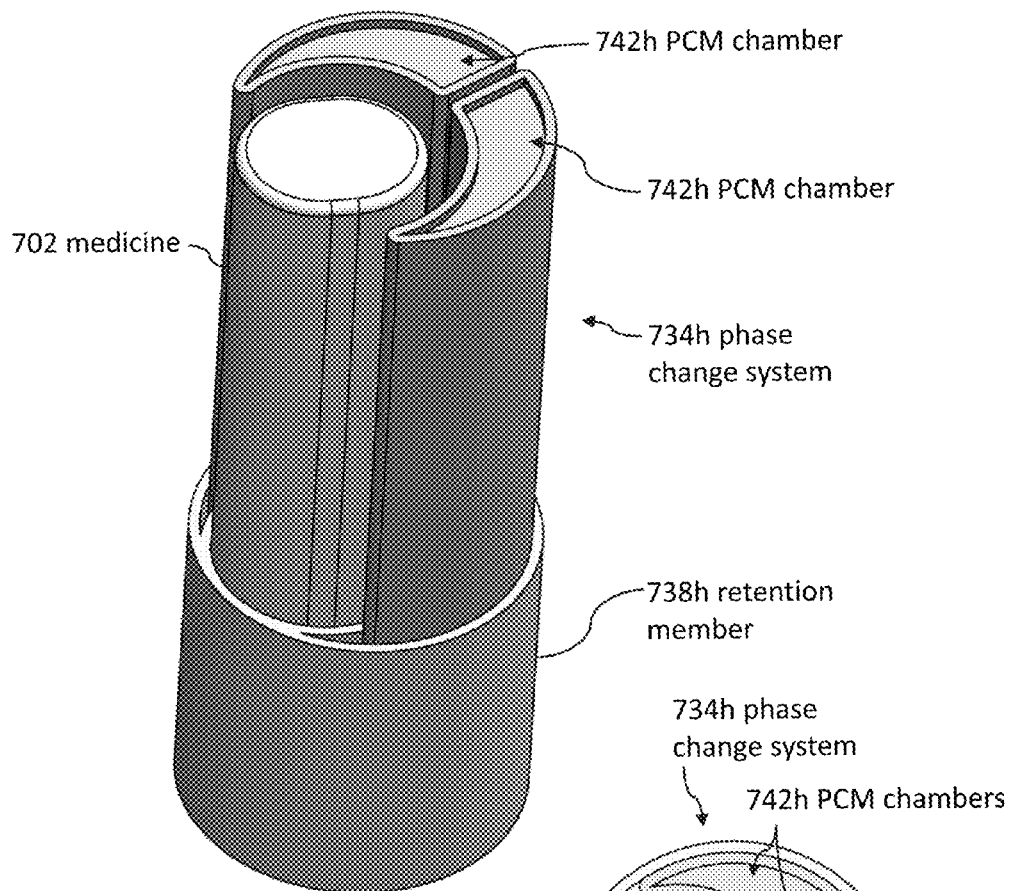
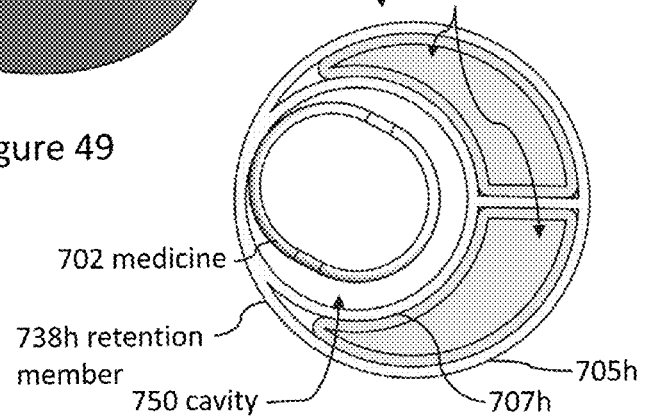
Figure 49
Figure 50

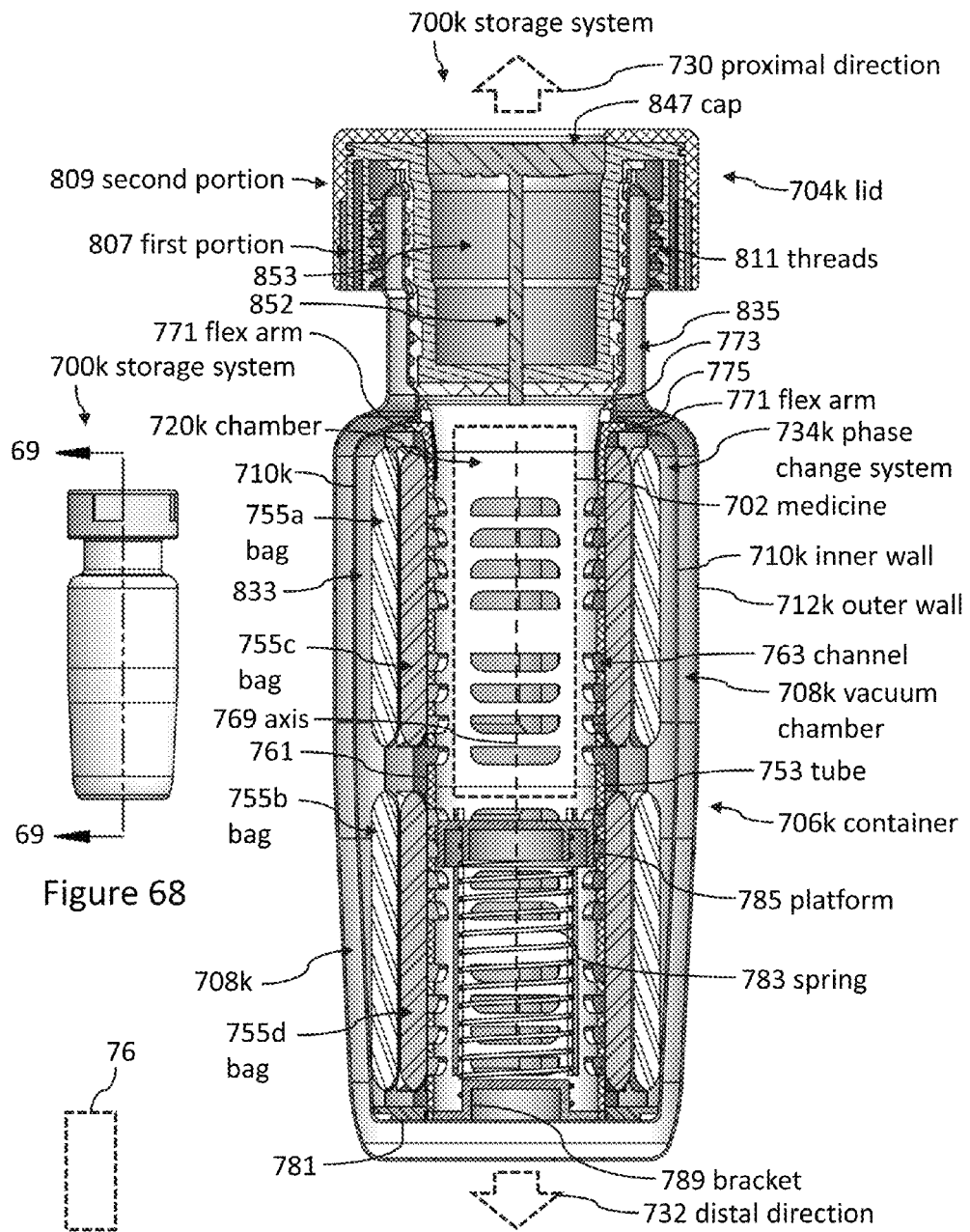
Figure 68
Figure 69

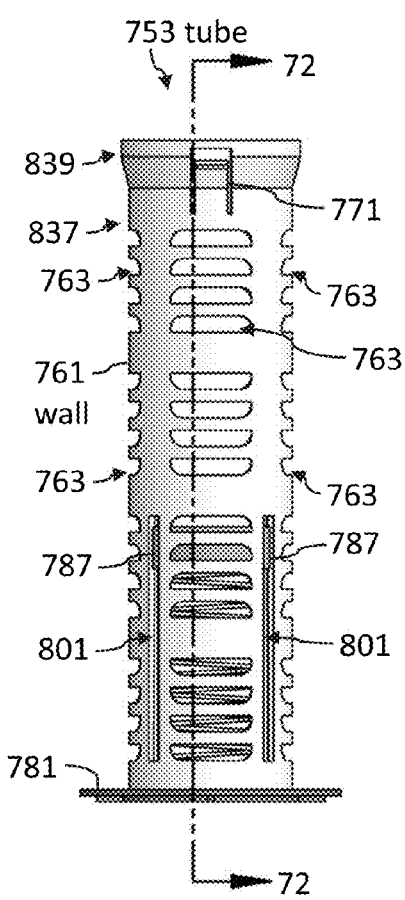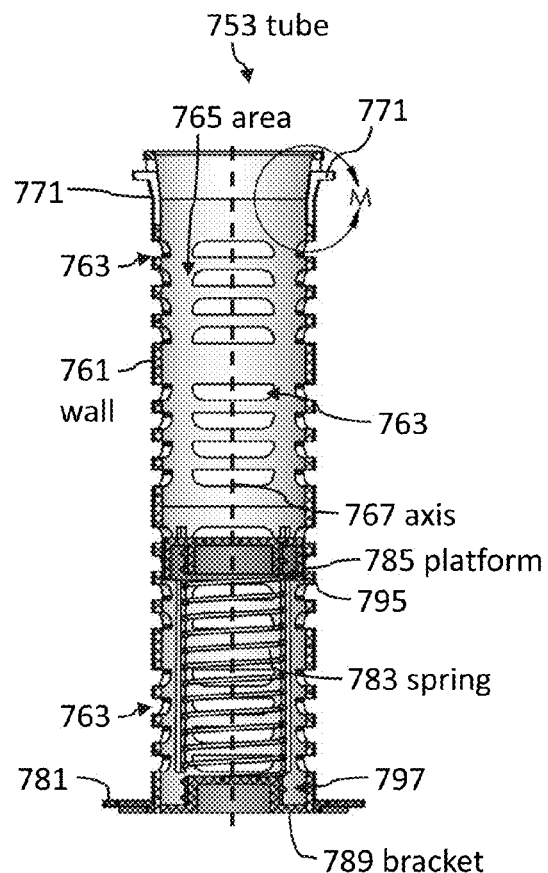
Figure 71
Figure 72
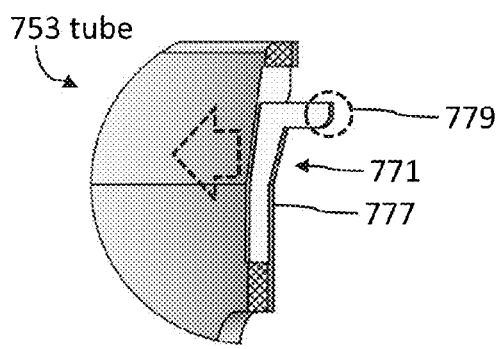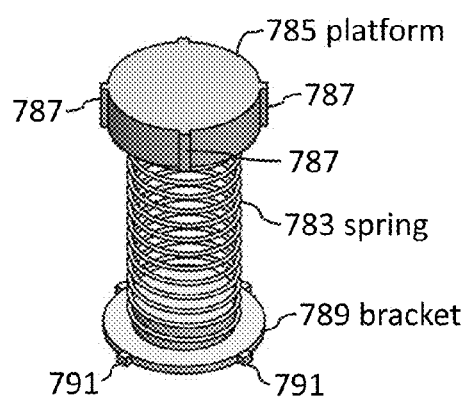
Figure 73
Figure 74

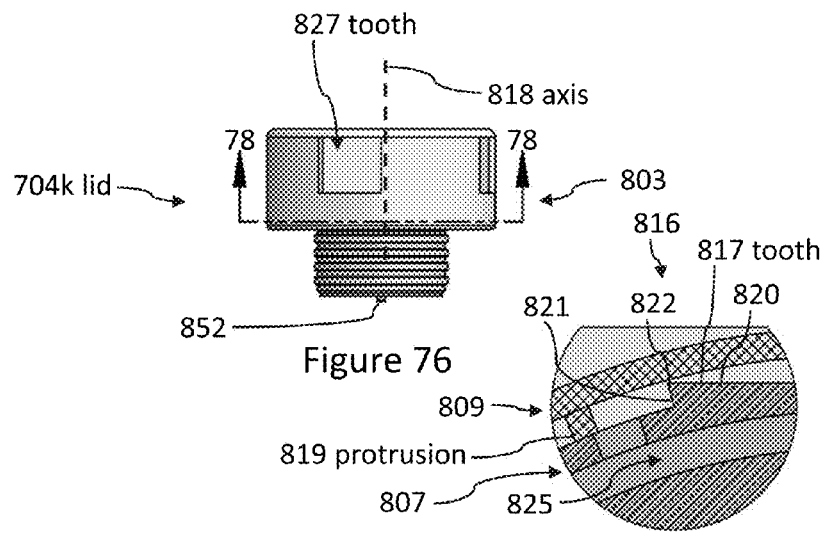
Figure 76
Figure 77
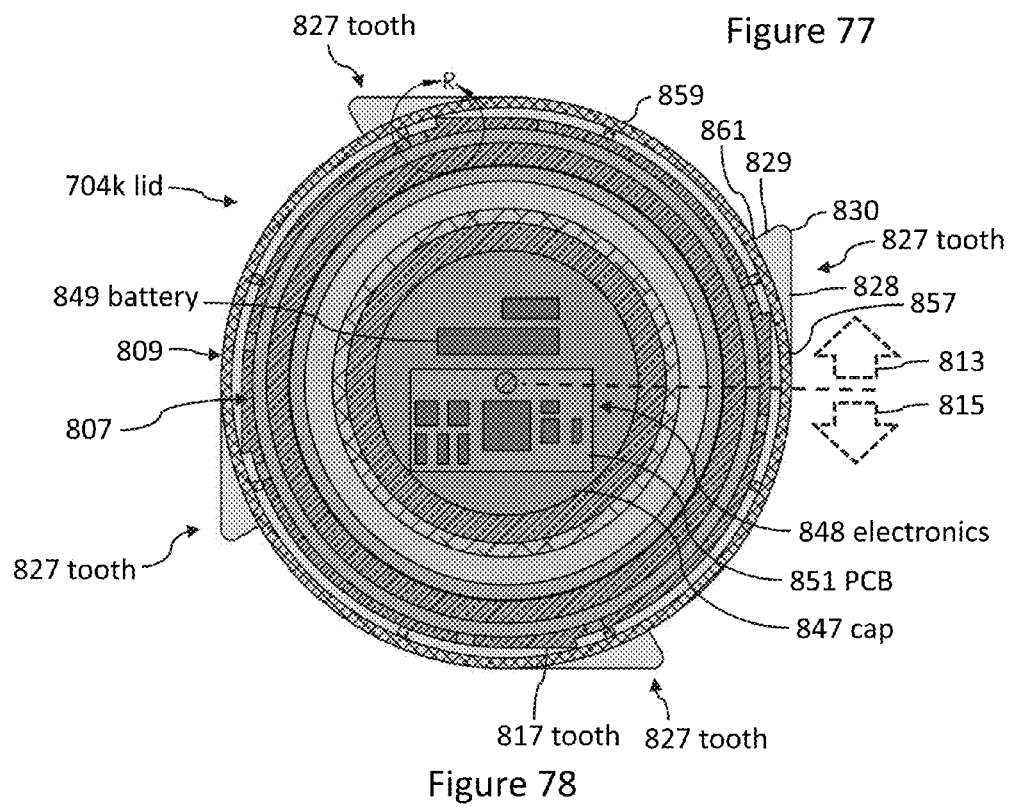
Figure 78

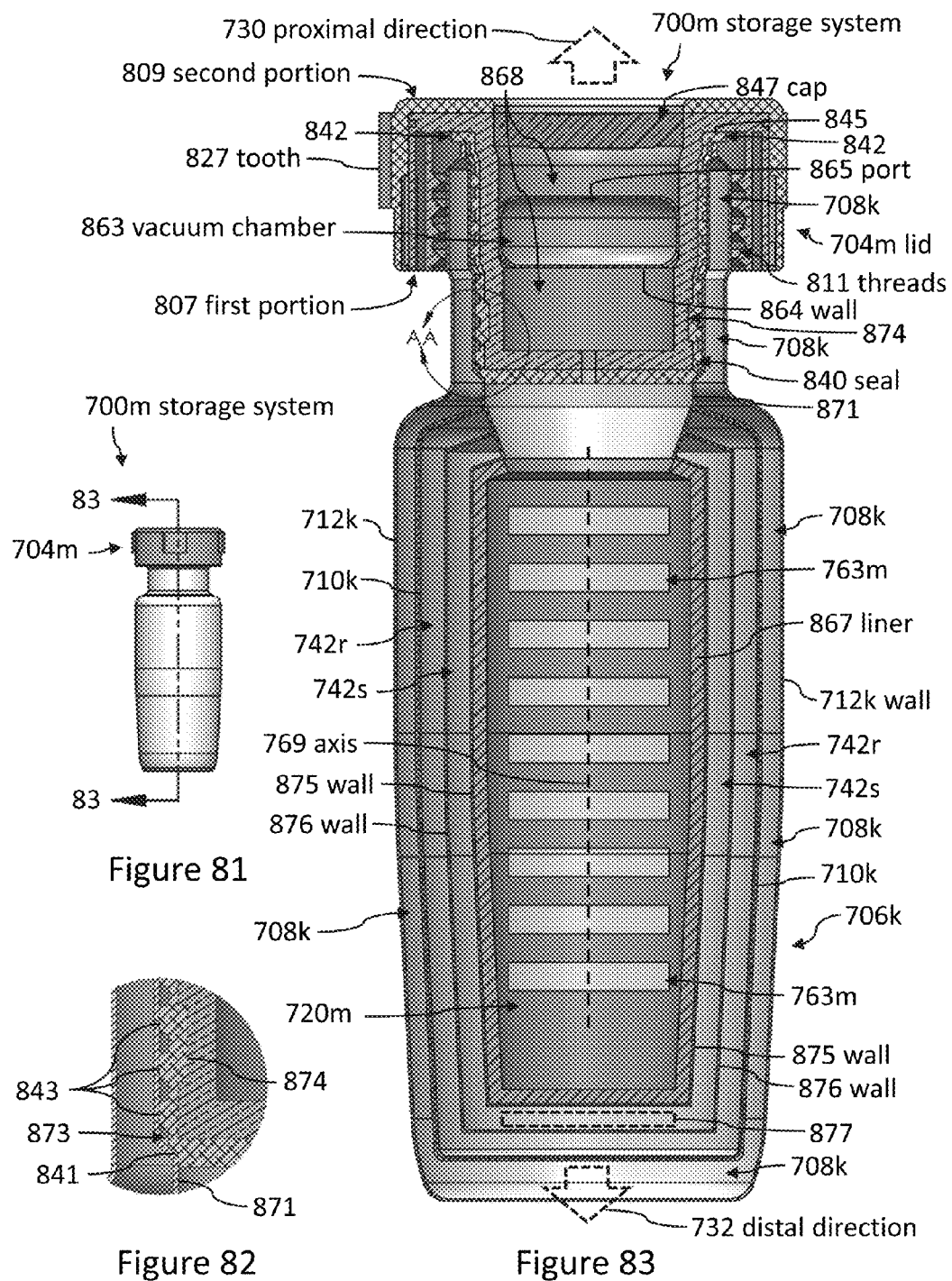

STORAGE SYSTEMS AND METHODS FOR MEDICINES

CROSS-REFERENCE TO RELATED APPLICATIONS

The entire contents of the following patent application are incorporated by reference herein: U.S. Nonprovisional patent application Ser. No. 15/170,465; filed Jun. 1, 2016; and entitled STORAGE SYSTEMS AND METHODS FOR MEDICINES.

The entire contents of the following patent application are incorporated by reference herein: U.S. Nonprovisional patent application Ser. No. 15/161,241; filed May 21, 2016; and entitled STORAGE SYSTEMS AND METHODS FOR MEDICINES.

The entire contents of the following patent application are incorporated by reference herein: U.S. Nonprovisional patent application Ser. No. 15/151,457; filed May 10, 2016; and entitled STORAGE SYSTEMS AND METHODS FOR MEDICINES.

The entire contents of the following patent application are incorporated by reference herein: U.S. Nonprovisional patent application Ser. No. 15/151,446; filed May 10, 2016; and entitled STORAGE SYSTEMS AND METHODS FOR MEDICINES.

The entire contents of the following patent application are incorporated by reference herein: U.S. Provisional Patent Application No. 62/293,691; filed Feb. 10, 2016; and entitled STORAGE SYSTEMS AND METHODS FOR MEDICINES.

The entire contents of the following patent application are incorporated by reference herein: U.S. Nonprovisional patent application Ser. No. 14/849,884; filed Sep. 10, 2015; and entitled STORAGE SYSTEMS AND METHODS FOR MEDICINES.

The entire contents of the following patent application are incorporated by reference herein: U.S. Nonprovisional patent application Ser. No. 14/616,652; filed Feb. 6, 2015; and entitled STORAGE SYSTEMS AND METHODS FOR MEDICINES.

The entire contents of the following patent application are incorporated by reference herein: U.S. Nonprovisional patent application Ser. No. 13/896,211; filed May 16, 2013; and entitled STORAGE SYSTEMS AND STORAGE METHODS FOR INJECTABLE SUBSTANCES.

BACKGROUND

Field

Various embodiments disclosed herein relate to systems and methods to store medicines. Certain embodiments relate to maintaining medicines at a suitable temperature.

Description of Related Art

Users of medicines, such as epinephrine, adrenaline, and insulin, are faced with a difficult challenge. On one hand, physicians often advise patients to take their medicines with them wherever they go. Yet on the other hand, the temperature of many medicines typically should be maintained within a temperature range that is incompatible with outdoor temperatures. For example, a certain injectable substance might need to be stored within a temperature range of 65 degrees Fahrenheit to 85 degrees Fahrenheit. Outdoor temperatures are often colder than 65 degrees Fahrenheit or warmer than 85 degrees Fahrenheit. As a result, patients who need injectable substances sometimes must remain indoors, risk going outdoors without the safety of carrying the injectable substance, or risk reducing the efficacy of the injectable substance by carrying it into environments with temperatures outside of the recommended range.

Prior art solutions have included refrigerators set to particular temperatures to store medicines within a suitable range. (The suitable range can be the storage range recommended by the manufacturer of the medicine.) Refrigerators require substantial electrical power. Constantly having to plug a refrigerator into a power supply, changing batteries, or recharging batteries is inconvenient. In addition, users sometimes forget to provide adequate power, which can result in harming the medicine, and thereby, creating a health risk to the user. Thus, there is a need for systems and methods to store injectable substances within a suitable temperature range while requiring little or no electrical power.

Prior art solutions have also included bulky insulation systems that are inconvenient for patients to carry outside. Due to this inconvenience, many patients do not carry vital medicines when they go outside. As a result, many patients have suffered medical emergencies and some patients have died. Thus, there is a need for systems and methods that are convenient enough for patients to carry their medicines outdoors.

SUMMARY

Several embodiments include methods of storing injectable substances, inhalers, pharmaceuticals, or drugs. In some embodiments, the storage system includes an outer case; a vacuum flask located inside the outer case; and/or a thermal bank located inside the vacuum flask. Some embodiments include isolating the injectable substance from fluids located outside of the injection device.

In some embodiments, the first phase change material can have a first melting temperature greater than 40 degrees Fahrenheit and less than 74 degrees Fahrenheit. The second phase change material can have a second melting temperature greater than 74 degrees Fahrenheit and less than 100 degrees Fahrenheit. The first melting temperature can be at least four degrees Fahrenheit less than the second melting temperature. For example, 74 degrees Fahrenheit can be approximately equal to a typical room temperature (although room temperatures commonly range from 67 degrees Fahrenheit to 80 degrees Fahrenheit in rooms having temperature controlled environments enabled by heating and/or air conditioning).

Using a "temperature dividing line" of 74 degrees Fahrenheit helps enable some embodiments to avoid inappropriately triggering melting and/or freezing while the storage system is located in a temperature controlled room. Imagine if the second phase change material had a melting temperature of less than 74 degrees. As a result, the second phase change material could completely melt before a person even moved the storage system from a room temperature into a hot outdoor environment that is warmer than a maximum recommended storage temperature of the medicine. In this case, the phase change of the second phase change material would not help reduce the rate of temperature rise inside the first chamber in response to heat transfer caused by the hot environment. Similarly, this "temperature dividing line" helps ensure the first phase change material will have a sufficiently low melting temperature such that the first phase change material should not solidify before the storage system is moved from a room temperature to an environment that is colder than a minimum recommended storage temperature.

In some embodiments, the first phase change material can have a first melting temperature greater than 63 degrees Fahrenheit and less than 74 degrees Fahrenheit. The second phase change material can have a second melting temperature greater than 74 degrees Fahrenheit and less than 83 degrees Fahrenheit. In some embodiments, the first phase change material can have a first melting temperature greater than 55 degrees Fahrenheit and less than 74 degrees Fahrenheit. The second phase change material can have a second melting temperature greater than 74 degrees Fahrenheit and less than 90 degrees Fahrenheit. These melting temperatures can be particularly effective to create a system that quickly responds (e.g., by changing phases) to temperature changes caused by leaving an indoor environment and entering an outdoor environment. Meridian Medical Technologies, Inc. makes a medicine called an EpiPen. EpiPens can have a minimum recommended storage temperature of 68 degrees Fahrenheit and a maximum recommended storage temperature of 77 degrees Fahrenheit. Other medicines often have different minimum and maximum recommended storage temperatures.

In several embodiments, a medicine storage system is configured to protect a medicine from a first external temperature less than a minimum recommended storage temperature and from a second external temperature greater than a maximum recommended storage temperature by utilizing phase changes to regulate a temperature of the medicine. Medicine storage systems can include an outer circular wall; an inner circular wall coupled to the outer circular wall; and a first vacuum chamber system located between the inner circular wall and the outer circular wall. The first vacuum chamber system can comprise at least one vacuum chamber. In some embodiments, dividing walls couple the outer wall to the inner wall and separate a first vacuum chamber from a second vacuum chamber.

In some embodiments, medicine storage systems include a first chamber at least partially surrounded by the first vacuum chamber system; a removable medicine container located inside the first chamber; and a proximal portion of the medicine storage system. The proximal portion can comprise an opening to the first chamber. The opening can be covered by a removable lid. The medicine storage system can be configured such that removing the lid enables a user to remove the medicine container from the first chamber.

In several embodiments, the medicine storage system comprises a phase change system that includes a second chamber having a first phase change material and a third chamber having a second phase change material. The phase change system can be at least partially surrounded by the first vacuum chamber system such that the first vacuum chamber system is configured to insulated the phase change system from an environment that is external to the medicine storage system. The first phase change material can have a first melting temperature greater than 40 degrees Fahrenheit and less than 74 degrees Fahrenheit, and the second phase change material can have a second melting temperature greater than 74 degrees Fahrenheit and less than 100 degrees Fahrenheit.

In some embodiments, a medicine storage system comprises a liner located in the first chamber. The liner can surround at least a majority of the removable medicine container. The liner can be made from a first material. The first chamber can be made from a second material that is at least two times harder than the first material as measured on the Brinell scale.

In several embodiments, a medicine storage system comprises a first seal located between the lid and the opening to the first chamber (e.g., such that the first seal is configured to block fluid from entering the first chamber to keep the medicine container dry). The first seal can be configured to reduce heat transfer from an internal portion of the medicine storage system to an area outside the medicine storage system.

In some embodiments, the lid is coupled to the proximal portion of the medicine storage system by screw threads. The first seal can be compressed by inserting a portion of the lid into the opening such that the first seal is compressed between the portion of the lid and a radially inward protrusion of the opening.

In several embodiments, the medicine storage system comprises a second seal located between the lid and the opening. The second seal can be a radial seal that is radially compressed between the opening and the lid. A medicine storage system can further comprise an air gap between the first seal and the second seal such that (1) the radial seal is configured to fluidly isolate the air gap from a proximal portion of the opening and (2) the first seal is configured to fluidly isolate the air gap from at least one of the first chamber and a distal portion of the opening. The second seal can be located proximally relative to the first seal. The first and second seals can be located distally relative to the screw threads.

In some embodiments, the lid comprises a groove that faces radially outward. At least one of the first and second seals can comprise a portion located in the groove. The groove can be configured to help retain at least one seal.

In several embodiments, a third seal is located between a proximal end of the opening and a distally facing surface of the lid. The third seal can be compressed between the proximal end and the distally facing surface. The third seal can be located proximally relative to the first and second seals. The first, second, and third seals can be molded from rubber materials.

In some embodiments, the lid comprises a second vacuum chamber. The second vacuum chamber can be fluidly isolated from the first vacuum chamber system such that screwing the lid onto the proximal portion of the medicine storage system rotates the second vacuum chamber relative to the first vacuum chamber system. The lid can comprise a metal wall having a port that is welded closed. The port can be used to remove a gas from the second vacuum chamber. Then, the port can be welded closed. The second vacuum chamber can be located within the metal wall. The lid can further comprise insulation that surrounds at least a majority of the second vacuum chamber. The second vacuum chamber can be spherical, cylindrical, or any suitable shape.

In several embodiments, the second chamber and the third chamber are located radially outward from the first chamber relative to a first central axis of the first chamber. The third chamber can be located radially outward from the second chamber (e.g., relative to the first central axis). The second chamber can be located radially outward from the third chamber (e.g., relative to the first central axis).

In some embodiments, the medicine storage system comprising a recommended storage temperature. For example, a manufacturer of the medicine storage system can recommend a temperature range at which to store the medicine storage system. In some cases, this recommended storage temperature can be "room temperature" and/or a temperature range within plus or minus 20 degrees of 74 degrees Fahrenheit. The manufacturer can include this recommended storage temperature in a location in which customers will see the recommended storage temperature. The recommended storage temperature can be located on the medicine storage system (e.g., printed on the storage system). The recommended storage temperature can be located on packaging of the medicine storage system (e.g., a box in which a storage system is shipped or placed on a retail shelf). The recommended storage temperature can be located on instructions included with the medicine storage system (e.g., an instruction sheet or instruction booklet that explains how to use the storage system). The recommended storage temperature can be located on a website and/or in an instructional video.

In several embodiments, the first, second, and third chambers (of the medicine storage system) are concentric. The removable medicine container can be an injection device having epinephrine (e.g., an EpiPen). The recommended storage temperature can be greater than the first melting temperature and less than the second melting temperature such that the medicine storage system is configured such that when the medicine storage system is stored for one week in an environment having the recommended storage temperature, the first phase change material is liquid and the second phase change material is solid.

In some embodiments, the first chamber extends from the proximal portion towards a distal portion of the medicine storage system such that the first chamber is at least as long as a majority of a length between a proximal end of the medicine storage system and a distal end of the medicine storage system.

In several embodiments, the first chamber comprises a first central axis, the second chamber comprises a second central axis, the third chamber comprises a third central axis, and the second and third central axes are within 15 degrees of being parallel to the first central axis of the first chamber.

In some embodiments, the vacuum chamber has a smaller outer diameter in the proximal portion of the medicine storage system than in the distal portion of the medicine storage system. The vacuum chamber can extend farther proximally than the second and third chambers such that at least a portion of the opening is surrounded by the vacuum chamber but is not surrounded by the second and third chambers.

In several embodiments, a first portion of the lid is located radially inward relative to a portion of the vacuum chamber, and a second portion of the lid is located radially outward relative to the portion of the vacuum chamber.

In some embodiments, a proximal portion of the second chamber tapers radially inward and a proximal portion of the third chamber tapers inward to enable the vacuum chamber to have the smaller outer diameter in the proximal portion of the medicine storage system than in the distal portion of the medicine storage system.

In several embodiments, the medicine storage system comprises a radially inward protrusion located between the opening and the first chamber. The lid can comprise a seal compressed between a portion of the lid and the radially inward protrusion (to block fluid from entering the first chamber to keep the medicine container dry).

In some embodiments, at least a majority of the opening and at least a majority of the first chamber are isodiametric.

In several embodiments, at least a majority of the opening has diameters that are 10 percent to 65 percent larger than diameters of at least a majority of the first chamber.

In some embodiments, the first chamber comprises a first central axis, the second chamber comprises a second central axis, the third chamber comprises a third central axis, and the second and third central axes are within 15 degrees of being parallel to the first central axis.

BRIEF DESCRIPTION OF THE DRAWINGS

These and other features, aspects, and advantages are described below with reference to the drawings, which are intended to illustrate but not to limit the invention. In the drawings, like reference characters denote corresponding features consistently throughout similar embodiments.

FIG. 18 illustrates a perspective view of a phase change system, according to some embodiments.

FIG. 19 illustrates a perspective view of a container without a lid, according to some embodiments.

FIG. 43 illustrates a side view of a tubular retention member, according to some embodiments.

FIG. 44 illustrates a top view of a tubular retention member, according to some embodiments.

FIG. 45 illustrates a perspective view of a tubular retention member, according to some embodiments.

FIGS. 46-48 illustrate various views of PCM chambers made from a highly-flexible, multi-layer barrier film sheet having blister-style bags filled with PCM and hermetically sealed to prevent leakage or intrusion, according to some embodiments.

FIG. 49 illustrates a perspective view of a phase change system that has a radially offset cavity to hold medicine, according to some embodiments.

FIG. 50 illustrates a top view of the phase change system shown in FIG. 49, according to some embodiments.

FIGS. 67 and 68 illustrate side views of a medicine storage system, according to some embodiments.

FIG. 69 illustrates a cross-sectional view taken along line 69-69 from FIG. 68, according to some embodiments.

FIG. 71 illustrates a side view of a tube, according to some embodiments.

FIG. 72 illustrates a cross-sectional view taken along line 72-72 from FIG. 71, according to some embodiments.

FIG. 73 illustrates an enlarged view of the area indicated by circle M in FIG. 72, according to some embodiments.

FIG. 74 illustrates a perspective view of a spring assembly, according to some embodiments.

FIG. 76 illustrates a side view of a lid, according to some embodiments.

FIG. 77 illustrates an enlarged view of the area indicated by circle R in FIG. 78, according to some embodiments.

FIG. 78 illustrates a cross-sectional view taken along line 78-78 from FIG. 76, according to some embodiments.

FIG. 81 illustrates a side view of a medicine storage system, according to some embodiments.

FIG. 82 illustrates an enlarged view of the area indicated by circle AA in FIG. 83, according to some embodiments.

FIG. 83 illustrates a cross-sectional view taken along line 83-83 from FIG. 81, according to some embodiments.

DETAILED DESCRIPTION

Figure 1:
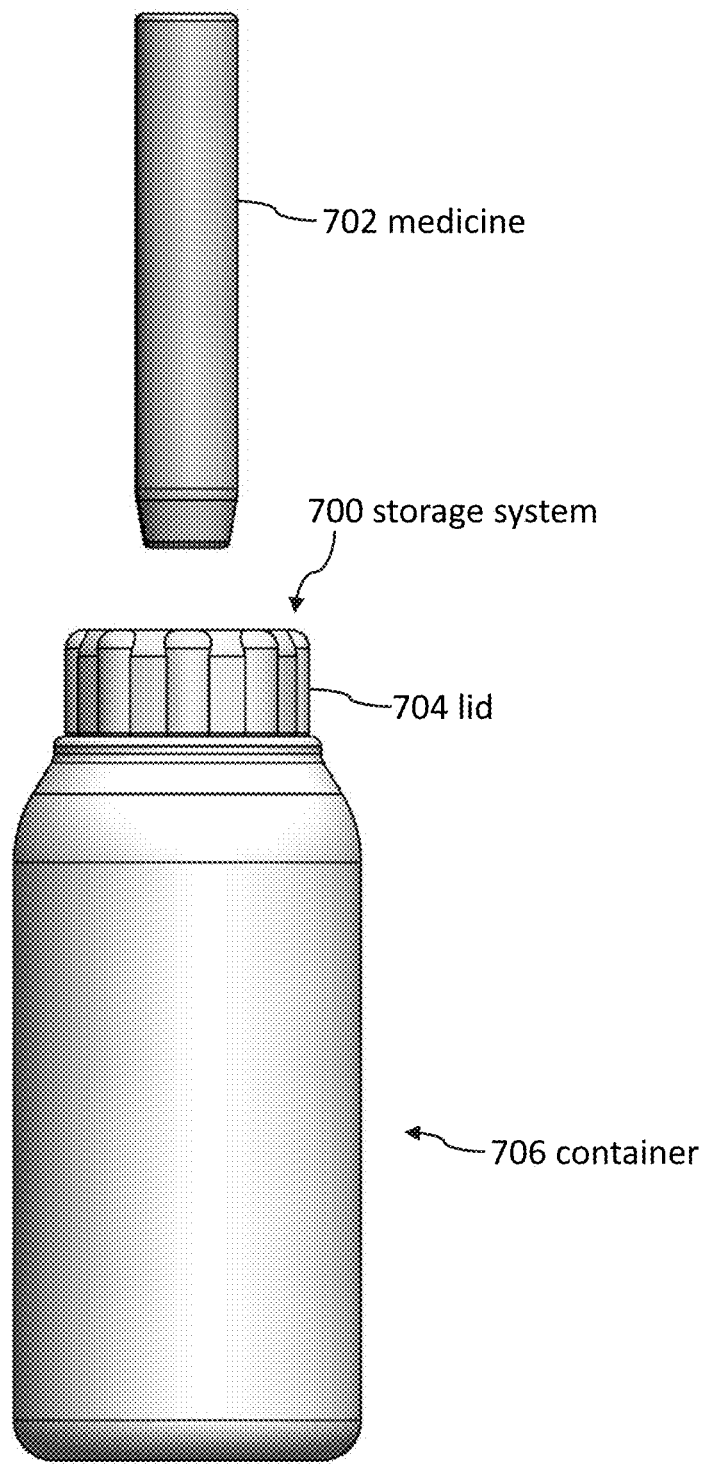
FIG. 1 illustrates a side view of a medicine storage system, according to some embodiments.

Although certain embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein. The features of each embodiment can be combined with the other embodiments.

People can damage their medicines by taking them outside in hot or cold weather. On the other hand, some people need to carry their medicines with them wherever they go (even if the weather is extremely hot or cold). Specially constructed storage systems can protect medicines from damage due to hot and cold weather without requiring bulky structures or expensive components that consume electricity to regulate temperature.

Any of the embodiments illustrated herein and/or incorporated by reference can include a storage system comprising a phase change system; a first container configured to hold at least a portion of the phase change system; and a first chamber located within the first container and configured to hold a medicine. As explained herein, phase change systems can comprise a first phase change material and/or a second phase change material. The first phase change material can have a first melting temperature greater than 40 degrees Fahrenheit and less than 74 degrees Fahrenheit. The second phase change material can have a second melting temperature greater than 74 degrees Fahrenheit and less than 100 degrees Fahrenheit. Thus, the phase change system can protect the medicine from temperatures above and below room temperature.

Refrigeration systems typically are large, expensive, fragile, and use electricity to regulate temperature. In contrast, phase change systems can be configured to protect medicine from a first external temperature less than a minimum recommended storage temperature and from a second external temperature greater than a maximum recommended storage temperature by utilizing phase changes to regulate a temperature of the medicine. Because phase change systems do not require electronics and pumps, they are very robust and can be built for a small fraction of the cost of refrigeration systems. Imagine a child who needs an epinephrine injector having to carry even a small refrigerator wherever she goes to prevent hot temperatures from ruining her potentially life-saving epinephrine.

In stark contrast, the child could easily carry a medicine storage system that relies on the phase change systems described herein, which can even be designed to protect against both hot and cold temperatures to eliminate the need for the child to have to guess which temperature protection components she will need for a trip. For example, if the child goes camping, she may need to protect her medicine against both hot afternoon temperatures and cold nighttime temperatures.

Containers can come in many different shapes and sizes. Some containers are vacuum flasks. Vacuum flasks can prevent high heat transfer rates to enable minimizing the amount of phase change material necessary to adequately protect a medicine. Thus, the system can be smaller than would be the case without a vacuum flask.

On the other hand, vacuum flasks often have rigid outer walls, which can make carrying them uncomfortable. Some containers are compliant bags with flexible walls. Compliant bags can be very comfortable to carry. Their flexible outer walls can facilitate fitting them into backpacks and purses (by enabling them to conform to various shapes).

FIG. 1 illustrates a side view of a storage system 700. FIG. 1 shows a medicine 702 (e.g., an EpiPen). A lid 704 can be removed (e.g., unscrewed) from the container 706 to facilitate placing the medicine 702 include the storage system 700.

FIG. 1 illustrates one shape of the medicine 702, but the embodiments described herein and/or incorporated by reference can be adapted to fit medicines of many different shapes and sizes. For example, U.S. Nonprovisional patent application Ser. No. 14/849,884, which is incorporated by reference herein, includes many storage systems such as storage systems 10, 11, 12, 200, 200*a*, 200*b*, 200*c*, 200*d*, 200*e*, 200*f*, 200*g*, 200*h*, 200*i*, 300, 400, 500. Many different types of storage systems are described herein such as storage systems 700, 700*a*, 700*b*, 700*d*, 700*e*, 700*f*, 700*h*, 700*i*, 700*k*, 700*m*. These storage systems and additional storage systems can be adapted to fit medicines of many different shapes and sizes.

In some embodiments, the medicine 702 is in a shape that is rectangular like a credit card, but is thicker than a credit card (e.g., 2 millimeters to 15 millimeters thick). The storage systems can be adapted to fit these rectangular shapes. In some embodiments, the medicine 702 is a generally cylindrical bottle and/or the shape of an inhaler.

Figure 2:
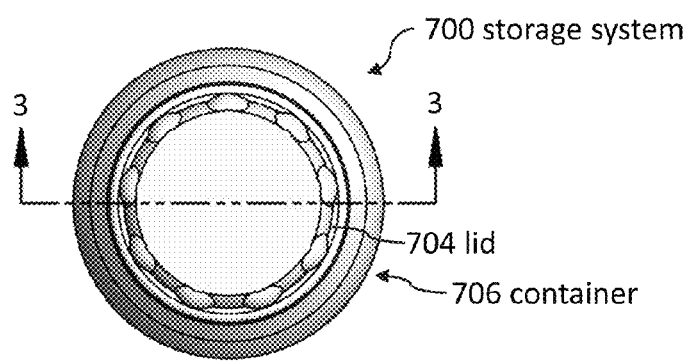
FIG. 2 illustrates a top view of a medicine storage system, according to some embodiments.
Figure 3:
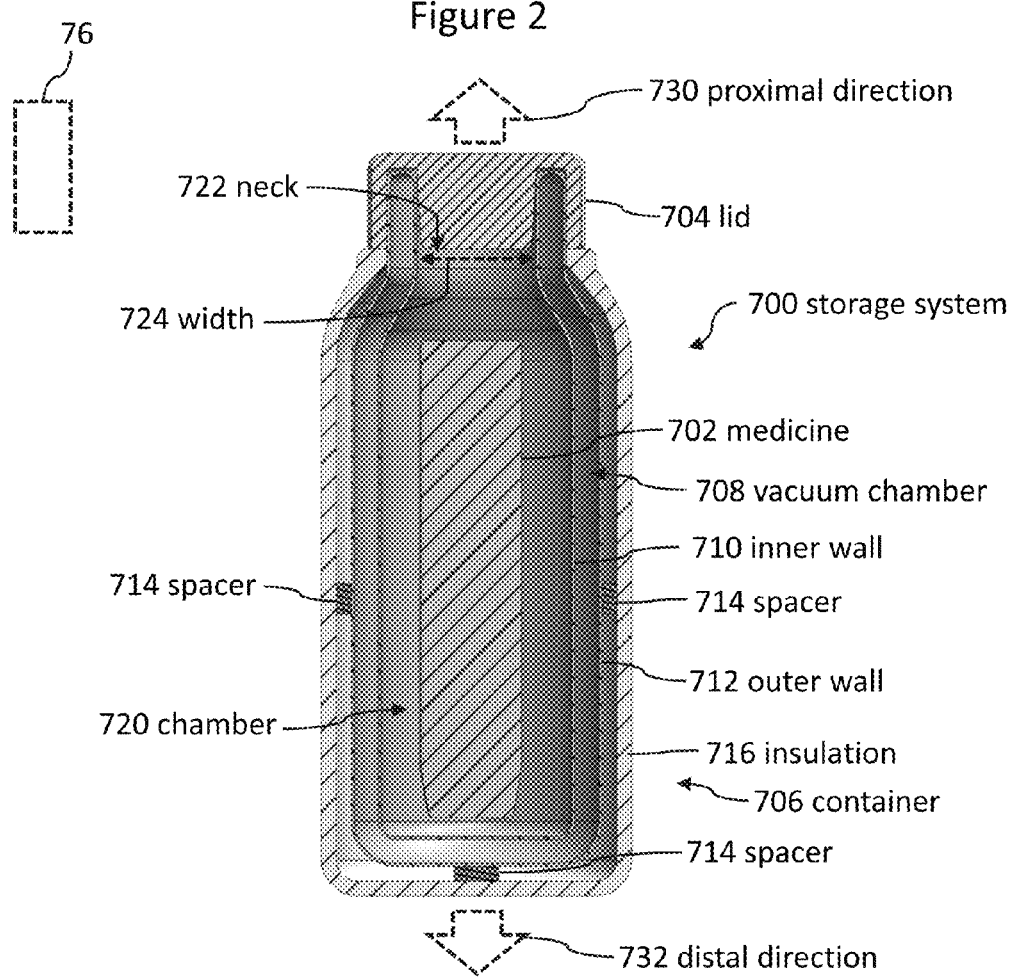
FIG. 3 illustrates a cross-sectional view of a medicine storage system along line 3-3 from FIG. 2, according to some embodiments.

FIG. 2 illustrates a top view of the storage system 700. FIG. 3 illustrates a cross-sectional view of the storage system 700 along line 3-3 from FIG. 2. The storage system 700 can include a vacuum chamber 708 formed by an inner wall 710 and an outer wall 712 (such that the vacuum chamber 708 is located between the walls 710, 712). The inner wall 710 and the outer wall 712 can be cylindrical or any other suitable shape.

The vacuum chamber 708 can at least partially surround a chamber 720 that holds the medicine 702. As illustrated in FIG. 3, an opening in the chamber 720 is plugged by the lid 704.

Insulating spacers 714 can couple an outer wall 712 of the vacuum chamber 708 to an outer insulated layer 716, which can be rigid or flexible. Some embodiments do not include the inner wall 710, the outer wall 712, and the vacuum chamber 708 (e.g., to facilitate making a storage system that is more flexible).

Some embodiments use portions (e.g., the insulation 716) that are made using rotational molding to create hollow parts. The hollow portions can be filled with insulation (e.g., injected with foam insulation). Portions (e.g., exterior walls) can be made from polyethylene.

Some embodiments use containers that are blow-molded. These blow-molded containers can form PCM chambers, which can hold phase change materials. The phase change materials can have any of the melting temperatures described herein or any other suitable melting temperature.

Some containers have one, two, three, five, ten, or any other suitable number of PCM chambers.

Many embodiments of phase change systems can be added to the storage system 700. In several embodiments, the phase change systems are added such that they are located inside the container 706, inside the outer insulated layer 716, and/or inside the vacuum chamber 708.

One challenge of inserting a phase change system is that the width 724 of the neck 722 leading into the chamber 720 can be narrower than a distal portion of the chamber 720. As a result, some phase change systems cannot fit through the neck 722. The phase change system embodiments described herein use unique structures and assembly techniques to enable them to fit through the neck 722. As a result, the systems are highly space efficient and enable cost-effective high-volume manufacturing.

Figure 57:
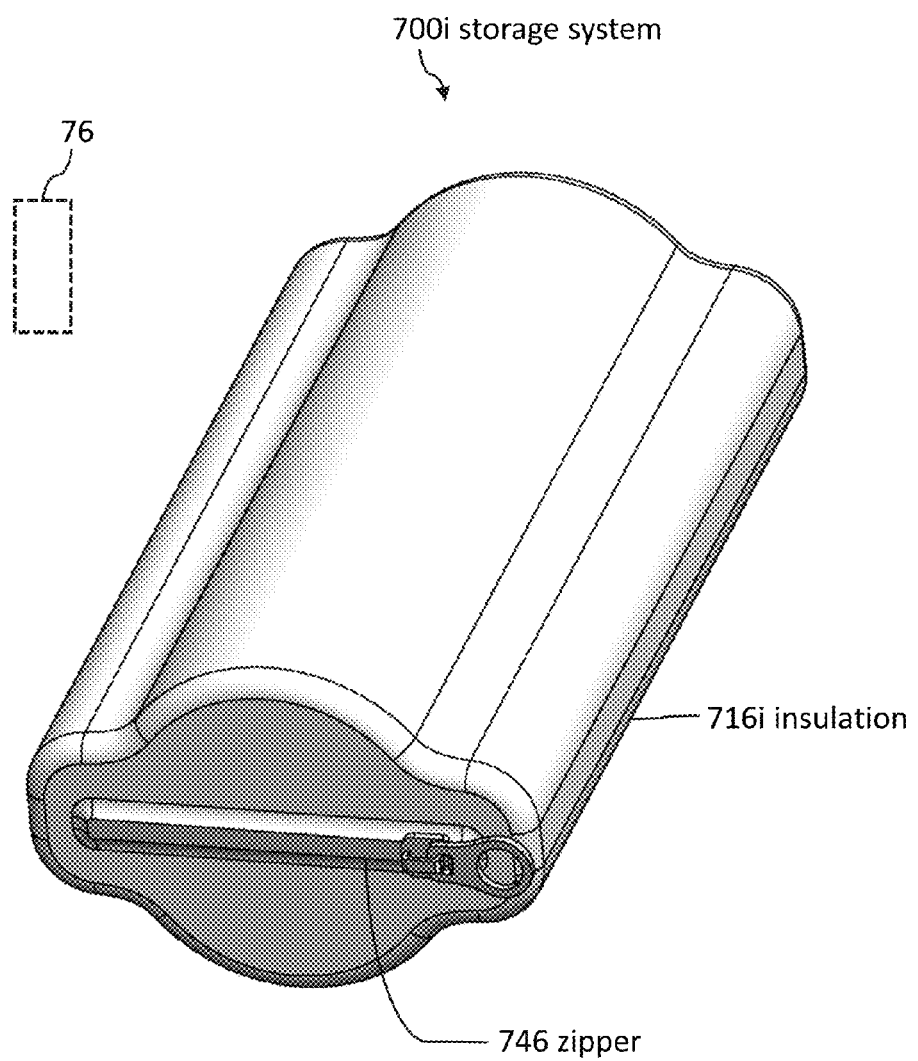
FIG. 57 illustrates a perspective view of a medicine storage system having a flexible outer housing, according to some embodiments.

The phase change systems described herein can be added to the storage system 700 shown in FIG. 3 and to the storage system 700i shown in FIG. 57. The phase change systems described herein can comprise a first phase change material and/or a second phase change material. The first phase change material can have a first melting temperature greater than 40 degrees Fahrenheit and less than 74 degrees Fahrenheit. The second phase change material can have a second melting temperature greater than 74 degrees Fahrenheit and less than 100 degrees Fahrenheit. Thus, the phase change system can protect the medicine from temperatures above and below room temperature.

The phase change systems described herein can comprise a first phase change material having a first melting temperature greater than 40 degrees Fahrenheit and less than 74 degrees Fahrenheit; a second phase change material having a second melting temperature greater than the first melting temperature and less than 74 degrees Fahrenheit; a third phase change material having a third melting temperature greater than 74 degrees Fahrenheit and less than 100 degrees Fahrenheit; and/or a fourth phase change material having a fourth melting temperature greater than the third melting temperature and less than 100 degrees Fahrenheit.

Figure 4:
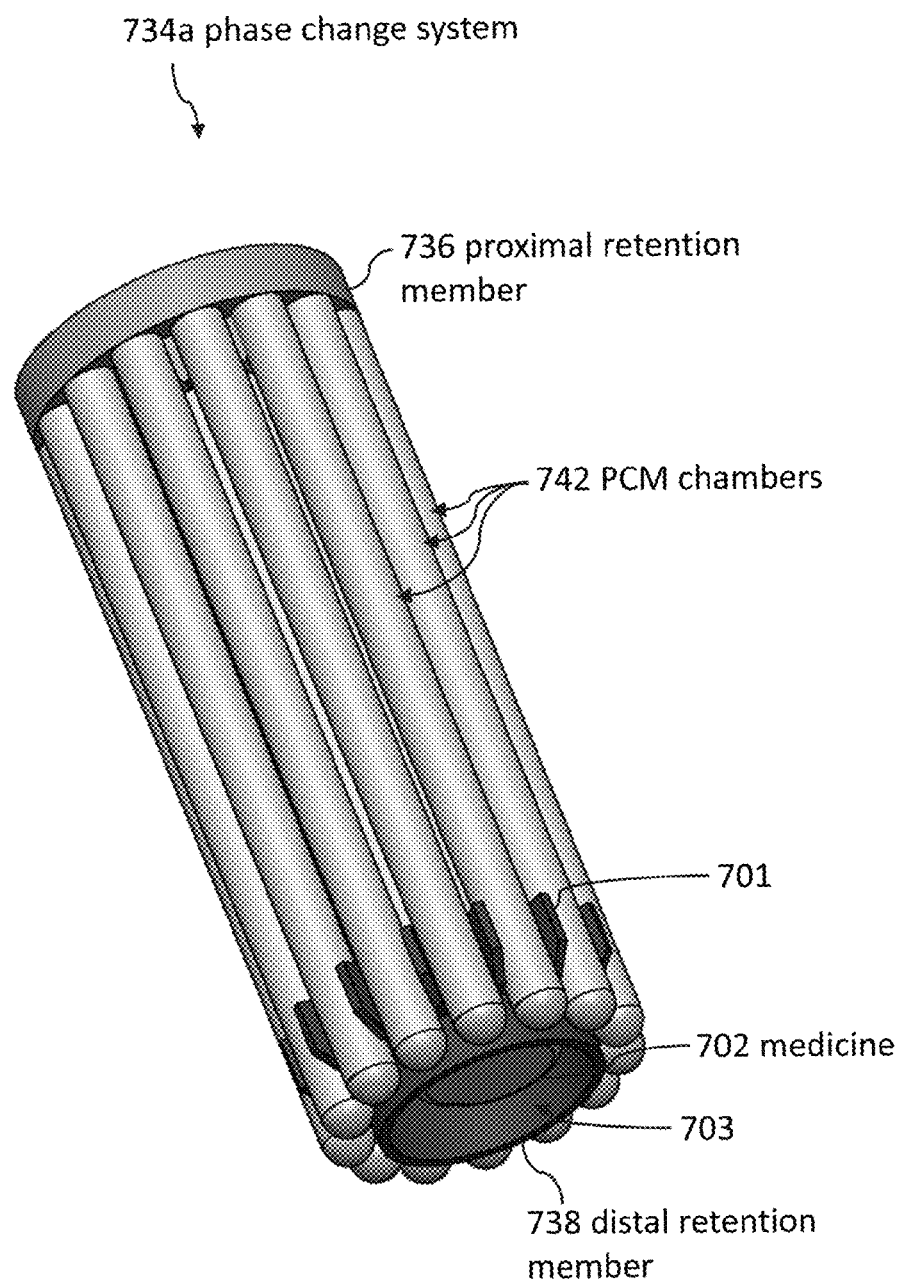
FIG. 4 illustrates a perspective view of a phase change system, according to some embodiments.

FIG. 4 illustrates a perspective view of a phase change system 734a configured to hold any combination of the phase change materials described herein. The phase change system 734a includes a proximal retention member 736 and a distal retention member 738 that secure phase change material ("PCM") chambers 742 around a perimeter of a chamber 740 configured to hold the medicine 702.

Each PCM chamber 742 can be filled with any of the phase change materials described herein (or incorporated by reference) and can be sealed to prevent leaking. The PCM chambers 742 can be hollow molded plastic tubes filled with PCM and then sealed.

The PCM chambers 742 can be hollow metal tubes filled with PCM and then hermetically sealed by a lid. The PCM chambers 742 can be made from aluminum, tin, steel, or any other suitable metal. The lid can be coupled to the tube using the same processes used to couple a lid to an aluminum soda can. The lid can be coupled to the tube by an "open top can sealer" sold by House of Cans, Inc. The can sealer can be manual or electric.

The lid can include protrusions to strengthen the lid. For example, the lid does not need to be flat, but instead can include ridges, bumps, and protrusions to strengthen the lid. Strengthening the lid can help make the PCM chamber 742 strong enough to tolerate the expansion and contraction typical of freezing and thawing PCMs.

The PCM chambers 742 can be formed by computer numerical control ("CNC") machining with wall thicknesses between 0.3 millimeters and 1.5 millimeters.

The PCM chambers 742 can be formed using processes typically used to form aluminum soda cans. Example processes include blanking, deep drawing, wall-ironing, end forming, trimming, washing, outside coating (e.g., to protect against corrosion), printing, drying, internal coating (e.g., to protect the metal and/or to protect the PCM from contamination), necking, flanging, end coating, testing for holes, and testing for internal defects. The PCM chambers 742 can be made from aluminum and then coated to guard against corrosion.

In some embodiments, the PCM chambers 742 have a diameter of at least 8 millimeters, at least 12 millimeters, less than 22 millimeters, and/or less than 30 millimeters. In some embodiments, the PCM chambers 742 have a length of at least 40 millimeters, at least 80 millimeters, less than 170 millimeters, and/or less than 185 millimeters.

The distal retention member 738 can be molded from compliant rubber that enables the distal retention member 738 to deform to enable a person to insert each PCM chamber.

Figure 5:
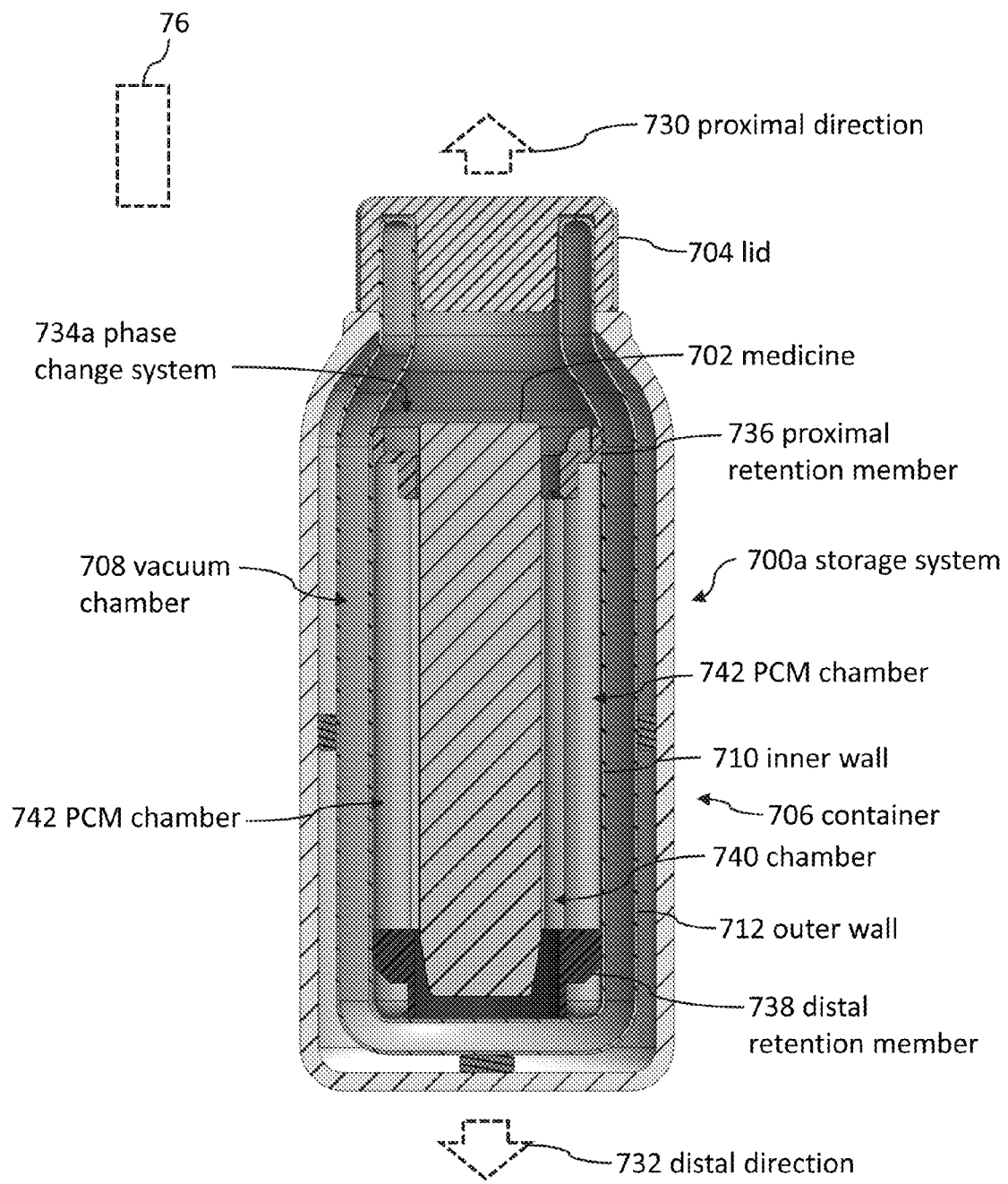
FIG. 5 illustrates the same cross section as FIG. 3 except that a phase change system is shown, according to some embodiments.
Figure 6:
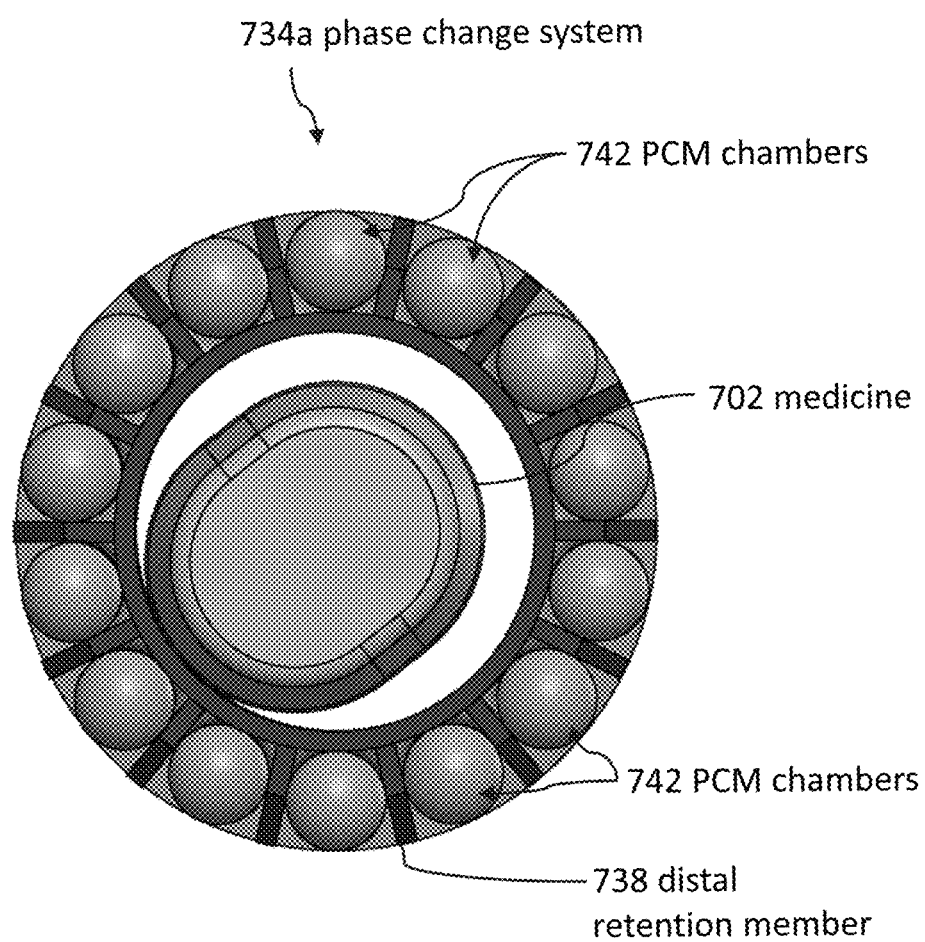
FIG. 6 illustrates a bottom view of a medicine at least partially surrounded by a phase change system, according to some embodiments.
Figure 7:
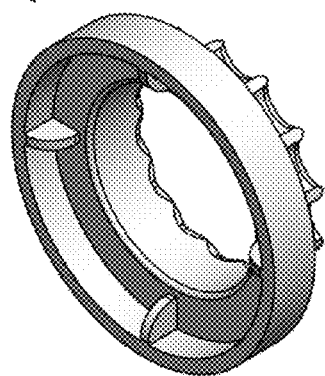
FIG. 7 illustrates a perspective view of a proximal retention member, according to some embodiments.
Figure 8:
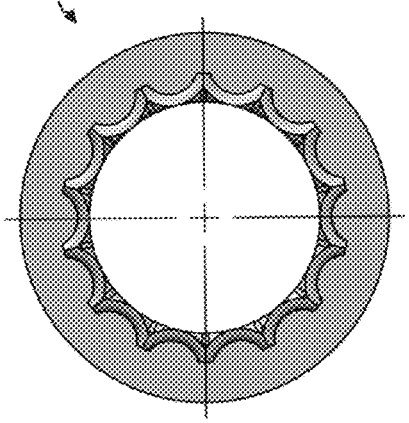
FIG. 8 illustrates a bottom view of a proximal retention member, according to some embodiments.
Figure 9:
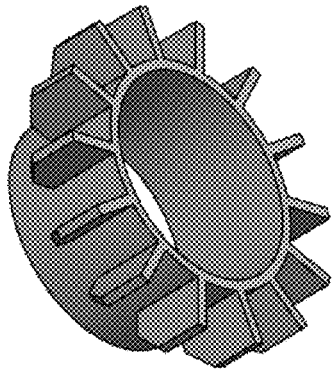
FIGS. 9 and 10 illustrate perspective views of a distal retention member, according to some embodiments.
Figure 10:
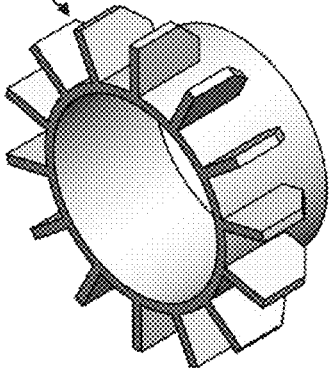

FIG. 5 illustrates the same cross section as FIG. 3 except that the phase change system 734a is shown. The storage system 700a can be assembled by inserting the distal retention member 738, inserting each PCM chamber 724 (e.g., one at a time), and then securing the proximal ends of the PCM chambers 724 by pressing the proximal retention member 736 through the neck 722 (labeled in FIG. 3). The proximal retention member 736 can be molded from flexible rubber to enable the proximal retention member to deform elastically to a small enough shape to fit through the neck 722. Then, once the proximal retention member 736 has moved distally past the neck 722, the proximal retention member 736 can spring back to essentially its original shape.

Phase change materials can be held in many different types of containers. Some embodiments use molded plastic containers to hold phase change materials. A phase change material can be poured into a container (e.g., while the phase change material is in a liquid state). The container can be sealed with a plastic lid that is coupled to the opening of the container.

Some embodiments use film pouches to hold phase change materials. The pouches can be hermetically sealed to prevent leakage.

The surface area of the container can be increased by molding fins, valleys, detents, concave features, convex features, etc. into the walls of the container. Increasing the surface area of the container's walls can increase the rate of heat transfer to and from the phase change material inside the container, which can reduce temperature differences between the medicine and the phase change material.

Vesl, LLC, which has an office in Melbourne, Fla., makes the following containers to hold a wide variety of phase change materials: BlockVesl (a stackable container with domed walls to increase heat transfer), MacroVesl (a blow-molded sphere having many chambers that hold phase change materials), MicroVesl (a spherical container having a multi-layer polymer structure), PackVesl (a highly flexible pouch made from multiple layered film and hermetically sealed to prevent leakage or intrusion), TubeVesl (a tube sealed with a lid), CanVesl (a metal cylinder), and MatVesl (a multi-layer barrier film sheet having blisters filled with PCM).

Phase Change Energy Solutions, which has an office in Asheboro, N.C., also makes containers that hold phase change material. Microtek Laboratories, Inc., having an office in Dayton, Ohio, also makes containers that hold phase change material.

Figure 11:
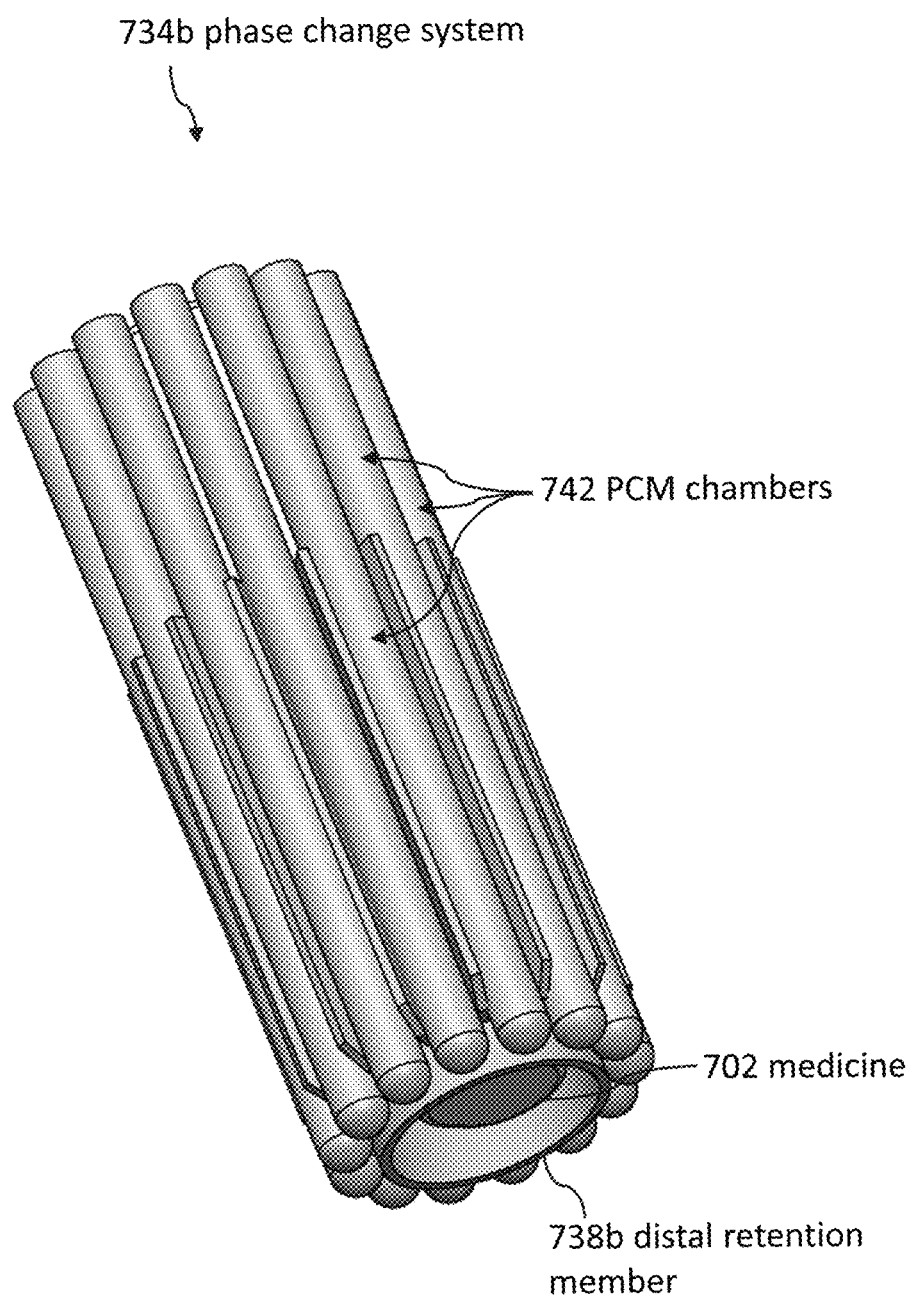
FIG. 11 illustrates a perspective view of a phase change system having PCM chambers in tubular containers that extend from a distal portion of the medicine storage system to a proximal portion of the medicine storage system, according to some embodiments.
Figure 12:
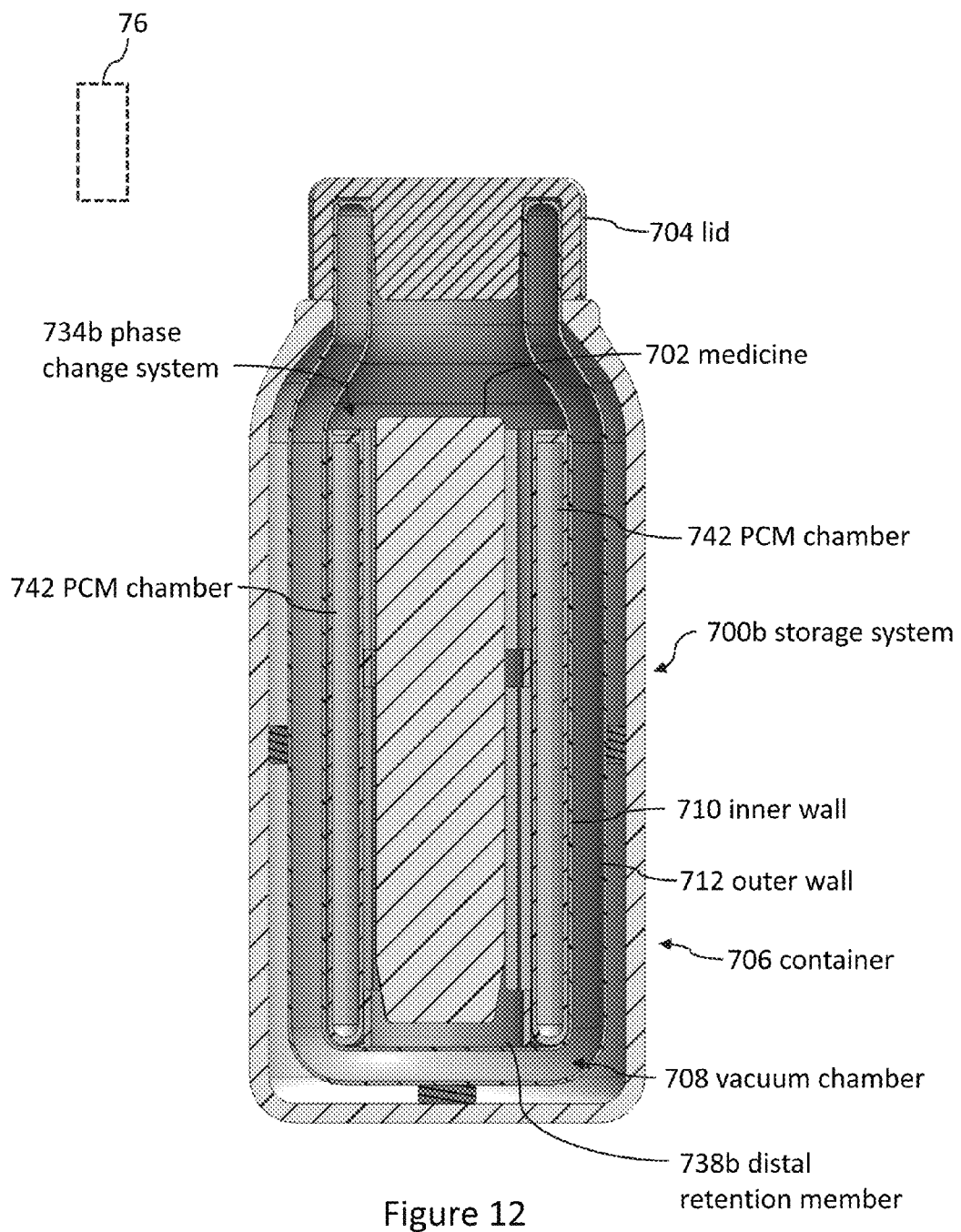
FIG. 12 illustrates the same cross section as FIG. 3 except that a phase change system is shown, according to some embodiments.

FIG. 11 illustrates a perspective view of a phase change system 734b having PCM chambers 742 in tubular containers that extend from a distal portion of the storage system 700b to a proximal portion of the storage system 700b (as shown in FIG. 12).

As used herein, "extends" means to continue in a specified direction or over a specified distance, but unless stated otherwise, typically does not mean to become longer.

The PCM chambers can alternate between a first PCM and a second PCM around the perimeter of the distal retention member 738b. For example, a first PCM chamber 742 can include a first phase change material, a second PCM chamber 742 that is adjacent to the first PCM chamber 742 can include a second phase change material with a higher melting temperature than the first phase change material, and a third PCM chamber 742 that is adjacent to the second PCM chamber 742 can include the first phase change material.

Figure 13:
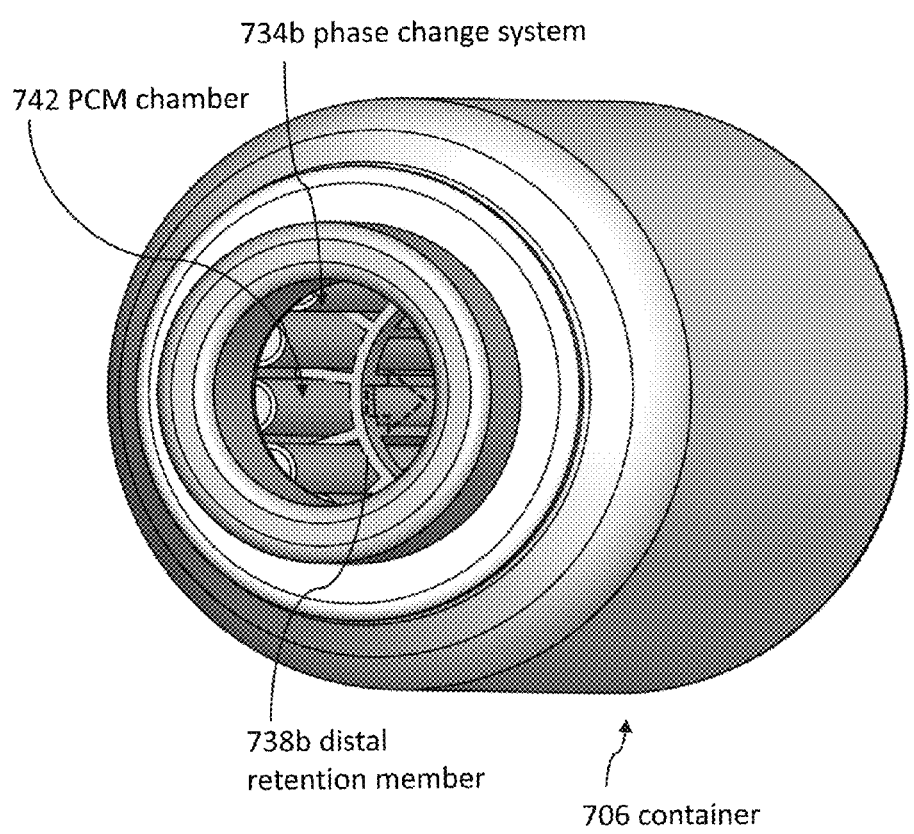
FIG. 13 illustrates a perspective view of a container without a lid, according to some embodiments.

FIG. 12 illustrates the same cross section as FIG. 3 except that the phase change system 734b is shown. FIG. 13 illustrates a perspective view of the container 706 without the lid 704 (shown in FIG. 1). The distal retention member 738b can be molded from a flexible material (such as a rubber with a hardness of 60 to 95 shore A). An inner wall (e.g., a portion of an inner hoop) can flex radially inward as shown by the arrow in FIG. 13. This elastic deformation can enable inserting a PCM chamber container through a narrow neck.

Figure 14:
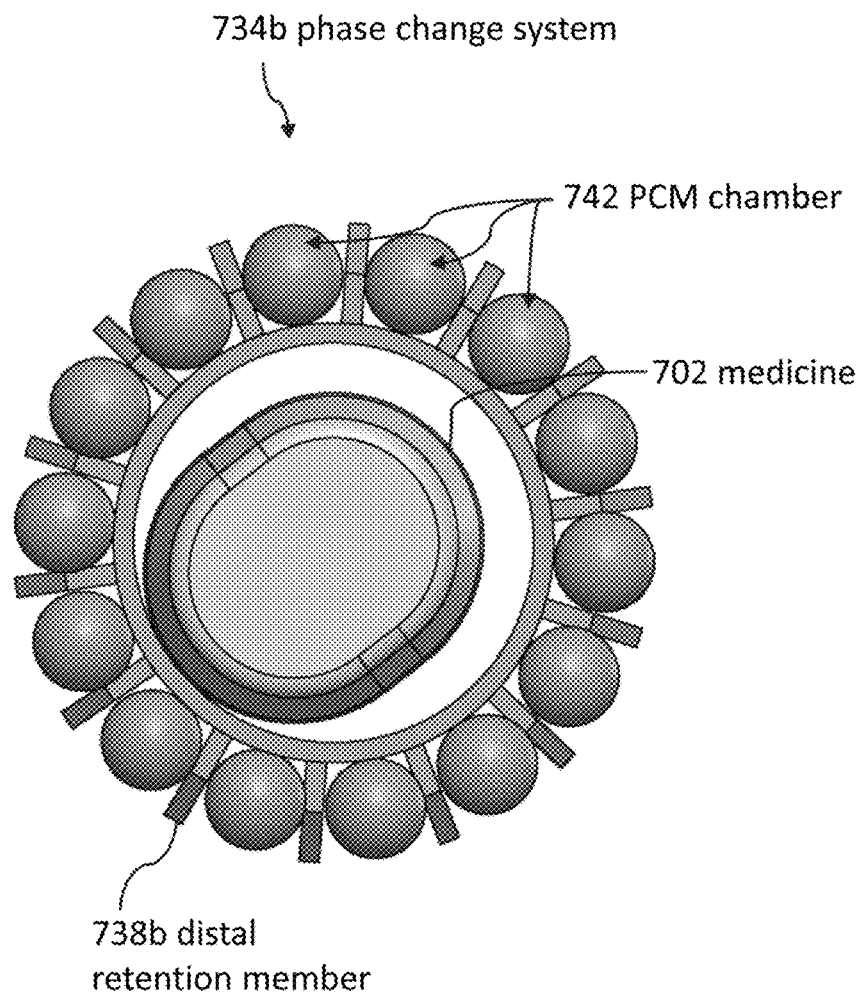
FIG. 14 illustrates a bottom view of a medicine and a phase change system, according to some embodiments.
Figures 15, 16, 17:
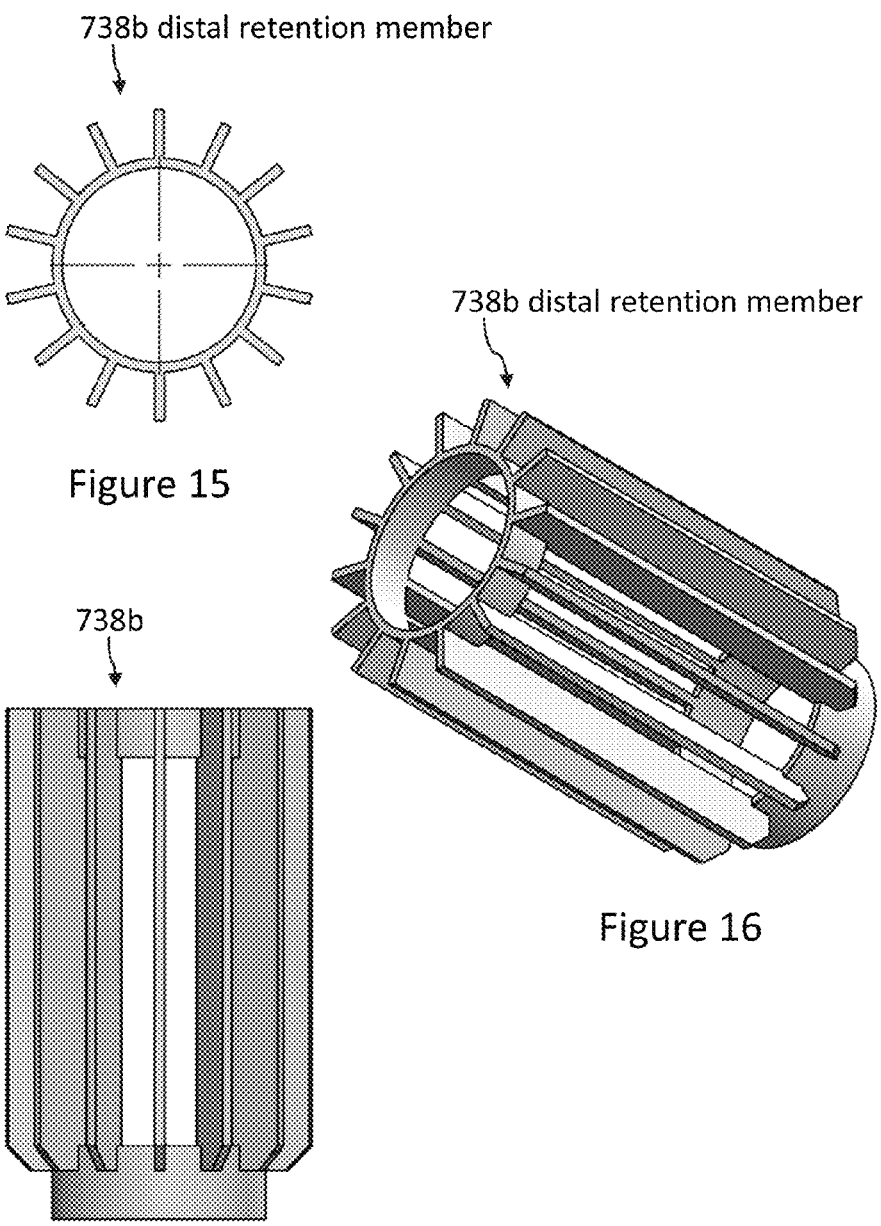
FIG. 15 illustrates a top view of a distal retention member, according to some embodiments.
FIG. 16 illustrates a perspective view of a distal retention member, according to some embodiments.
FIG. 17 illustrates a side view of a distal retention member, according to some embodiments.
Figure 20:
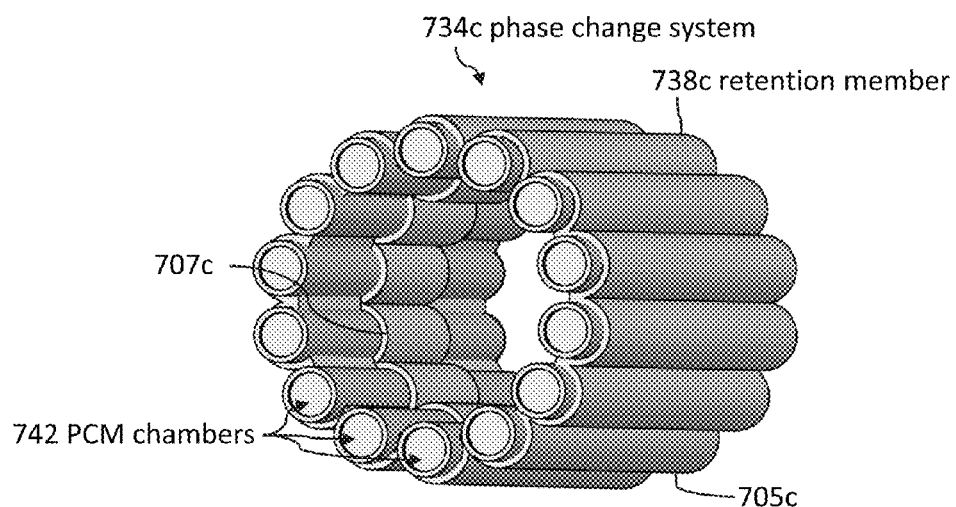
FIG. 20 illustrates a perspective view of a phase change system, according to some embodiments.
Figure 21:
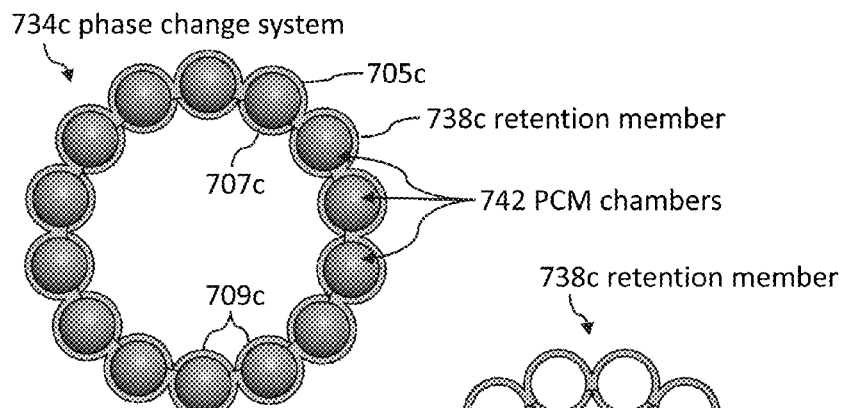
FIG. 21 illustrates a bottom view of a phase change system, according to some embodiments.
Figure 22:
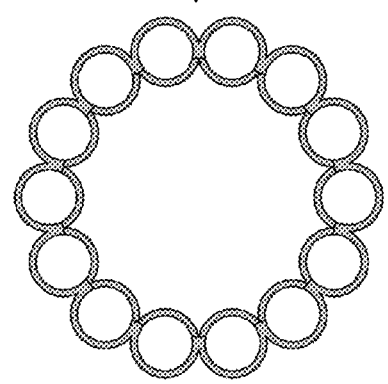
FIG. 22 illustrates a bottom view of a retention member, according to some embodiments.

FIG. 14 illustrates a bottom view of the phase change system 734b. FIGS. 15-17 illustrate various views of the distal retention member 738b shown in FIG. 11.

Figure 79:
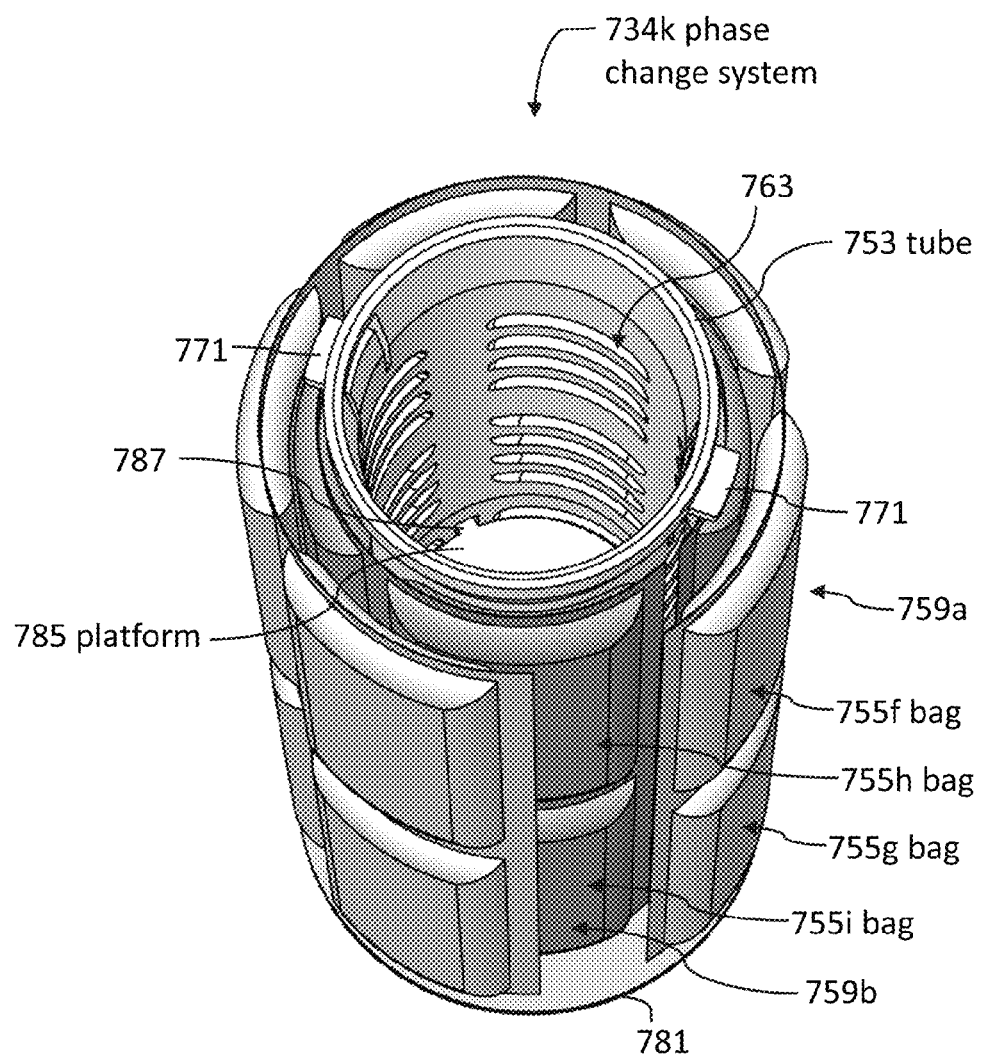
FIG. 79 illustrates a perspective view of a phase change system, according to some embodiments.

As shown in FIGS. 4-79, in some embodiments, a medicine storage system comprises an insulated container having an opening; a first lid configured to cover the opening; a phase change system located inside the insulated container; a medicine storage area located inside the insulated container; and a first retention member located inside the insulated container and configured to prevent the phase change system from blocking access to the medicine storage area. The storage system can be configured to provide access for inserting a medicine through the opening and into the medicine storage area.

As shown in FIGS. 4-6, 11-14, 18-21, 31-37, and 49-54, in several embodiments, the phase change system comprises a first tube having a first phase change material and a second tube having a second phase change material. The first phase change material can have a first melting temperature greater than 40 degrees Fahrenheit and less than 74 degrees Fahrenheit. The second phase change material can have a second melting temperature greater than 74 degrees Fahrenheit and less than 100 degrees Fahrenheit.

The PCM chambers 742, 742e, 742h in FIGS. 4-6, 11-14, 18-21, 31-37, 49, 50, and 52-54 are located inside hollow metal tubes at least partially filled with PCM and sealed with a lid. The metal tubes can be extruded and/or machined tubes. The tubes can have any suitable shape. The tubes can have circular cross sections, crescent cross sections, and/or triangular cross sections. In some embodiments, the tube shape varies along a central axis of the tube such that a first cross section at one distance from a distal end of the tube has a different shape than a second cross section at another distance from the distal end.

Referring mainly to FIG. 5, but also to FIGS. 4, 6, 11-14, 18-21, 31-37, and 49-54, the insulated container comprises a proximal portion and a distal portion. The distal portion is located farther from the opening (covered by the lid 704 in FIG. 5) than the proximal portion. The first retention member (e.g., 738, 738b, 738c, 738e, 738h) can be located inside the insulated container 706 in the distal portion. The first retention member can comprise a protrusion (e.g., 701) between the first tube and the second tube.

In some embodiments, the storage system comprises a second retention member (e.g., 736) located inside the insulated container and configured to prevent the phase change system from blocking access to the medicine storage area. The insulated container can comprise a central axis. The second retention member can be located inside the insulated container in the proximal portion. The first and second retention members can hold the first and second tubes within 30 degrees of parallel to the central axis (e.g., as shown in FIG. 5).

In several embodiments, the insulated container comprises a central axis. The storage system can have a plurality of tubes comprising the first tube and the second tube. The plurality of tubes can be spaced around an outer perimeter of the medicine storage area such that the plurality of tubes are located radially outward, relative to the central axis, from the medicine storage area (e.g., as shown in FIGS. 4-6, 11, 12, 14, 18-21, and 31-33).

In some embodiments, the first retention member secures the plurality of tubes radially outward from the medicine storage area and radially inward from an inner wall of a vacuum chamber that insulates the insulated container (e.g., as shown in FIGS. 4-6, 11, 12, 14, 18-21, and 31-33). The first retention member can comprise a cavity. The central axis of the insulated container can pass through the cavity. The cavity can comprise a portion of the medicine storage area (e.g., as shown in FIGS. 4-6, 11, 12, 14, 18-21, and 31-33). The first tube can be oriented within 30 degrees of parallel to the central axis. The second tube can be oriented within 30 degrees of parallel to the first tube. In some embodiments, the tubes are oriented parallel to the central axis (e.g., as shown in FIGS. 4-6, 11, 12, 14, 18-21, and 31-33).

In several embodiments, the first retention member comprises a protrusion oriented radially outward relative to the central axis. The protrusion can be located between the first tube and the second tube.

Referring now to FIGS. 20, 21, 50, and 52, in some embodiments, the first retention member 738h comprises a first wall 705c, 705h located between the inner wall 710 and the first tube (e.g., 742h). The first retention member 738h can comprise a second wall 707c, 707h located between the first tube and the medicine storage area (e.g., 750).

In several embodiments, the first retention member comprises a first hoop 709c and a second hoop 709c. The first tube can be located at least partially in the first hoop. The second tube can be located at least partially in the second hoop.

Referring now to FIGS. 4-56 and 69-79, in some embodiments, retention members (e.g., 736, 738, 738b, 738c, 738d, 738e, 738f, 738h, 753, 781) can deform to fit through a narrow opening of the insulated container. Once inside the insulated container, the retention members can spring back to a larger shape (than could fit through the opening without deformation). The first retention member can comprise a maximum diameter measured radially outward relative to the central axis. The opening can comprise a minimum diameter measured radially outward relative to the central axis. The maximum diameter of the first retention member can be larger than the minimum diameter of the opening.

The first retention member can be configured to change shape in a reversible manner to reduce the maximum diameter to enable inserting the first retention member through the opening. The first retention member can be configured to return to a shape having the maximum diameter after the first retention member has passed through the opening.

In several embodiments, the first tube comprises a first cylindrical portion at least partially filled with the first phase change material, and the second tube comprises a second cylindrical portion at least partially filled with the second phase change material. The first tube can be oriented parallel to the central axis, and the second tube can be oriented parallel to the central axis.

Referring now to FIGS. 31-37 and 49-54, in some embodiments, the first tube comprises outer dimensions characterized by a thickness and a width. The first tube has a maximum thickness measured in a direction radially outward from the central axis of the insulated container. The first tube comprises a maximum width measured perpendicular to the maximum thickness and perpendicular to the central axis. In several embodiments, the maximum width is at least two times larger than the maximum thickness.

Referring now to FIGS. 31-37, the first tube can be a portion of a wedge shape (e.g., with rounded edges). This shape can help fit several tubes around a perimeter of a circle or oval shaped medicine storage area.

The tube can include a lid configured to cover an opening to the tube. The lid can be laser welded to the tube. The lid can be coupled to the tube using processes used to attach lids to aluminum soda cans and/or processes used to attach lids to "tin cans" (which can be made from steel, aluminum, tin, or any other suitable metal).

Figure 31:
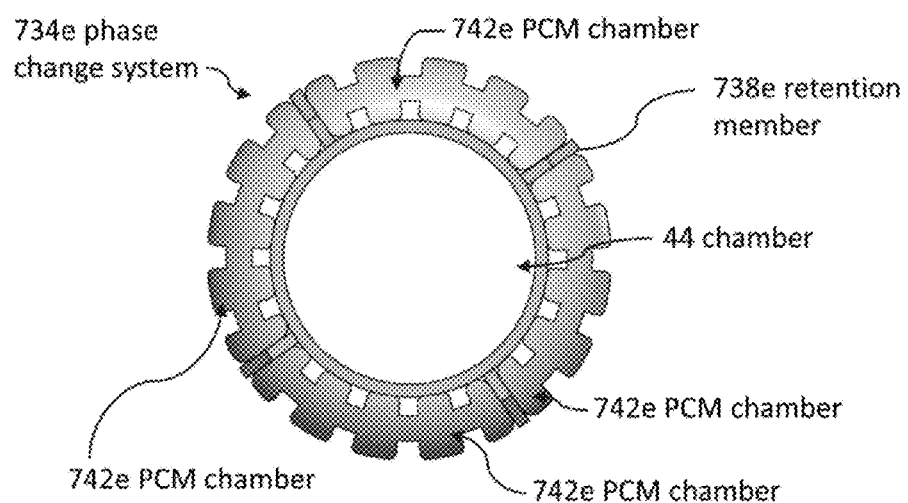
FIG. 31 illustrates a bottom view of a phase change system that includes a retention member that has radially outward protrusions that separate containers having PCM chambers, according to some embodiments.

In some embodiments, the first tube comprises at least one of fins, valleys, and detents (e.g., as shown in FIG. 31) configured increase a surface area of the first tube to promote heat transfer. The first retention member can comprise ventilation channels configured to enable airflow between the medicine storage area and the phase change system.

Referring now to FIGS. 49-54, in several embodiments, the insulated container comprises a first central axis, the first tube comprises a second central axis, the second tube comprises a third central axis, and the medicine comprises a fourth central axis. The first retention member can orient the second, third, and fourth central axes within 30 degrees of parallel to the first central axis of the insulated container (e.g., as shown in FIG. 49-52). The second, third, and fourth central axes can be located radially outward relative to the first central axis of the insulated container (e.g., as shown in FIG. 50 where the retention member 738h is concentric with the central axis of the insulated container shown in FIGS. 51 and 52).

Figure 52:
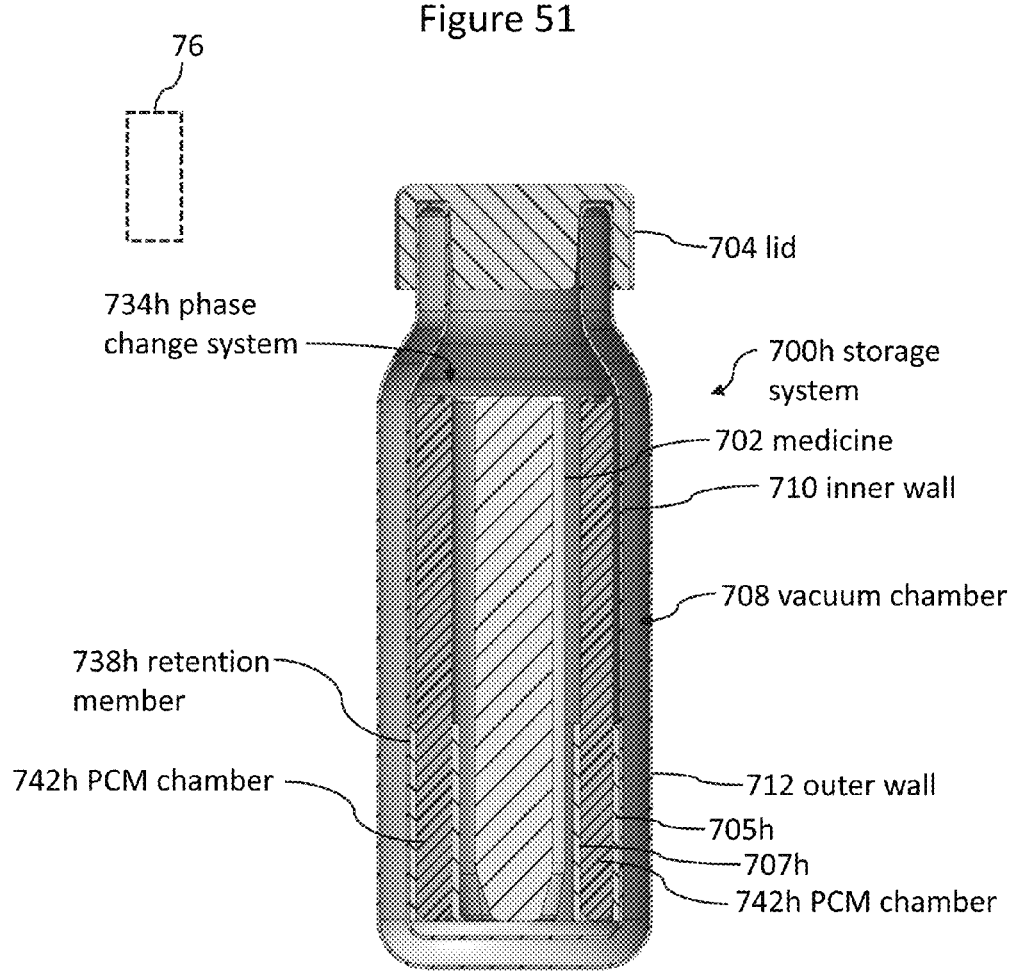
FIG. 52 illustrates a cross-sectional view taken along line 52-52 in FIG. 51, according to some embodiments.

In some embodiments, the first tube comprises a cross section that is perpendicular to the second central axis. As shown in FIG. 52, the cross section can have three outermost points 711 that form a triangle. Walls 713 of the first tube that connect the three outermost points 711 can be at least one of straight and curved. As shown in FIG. 52, the tubes are a portion of a crescent shape. The tubes have a cross section that is a portion of a crescent shape.

Figure 23:
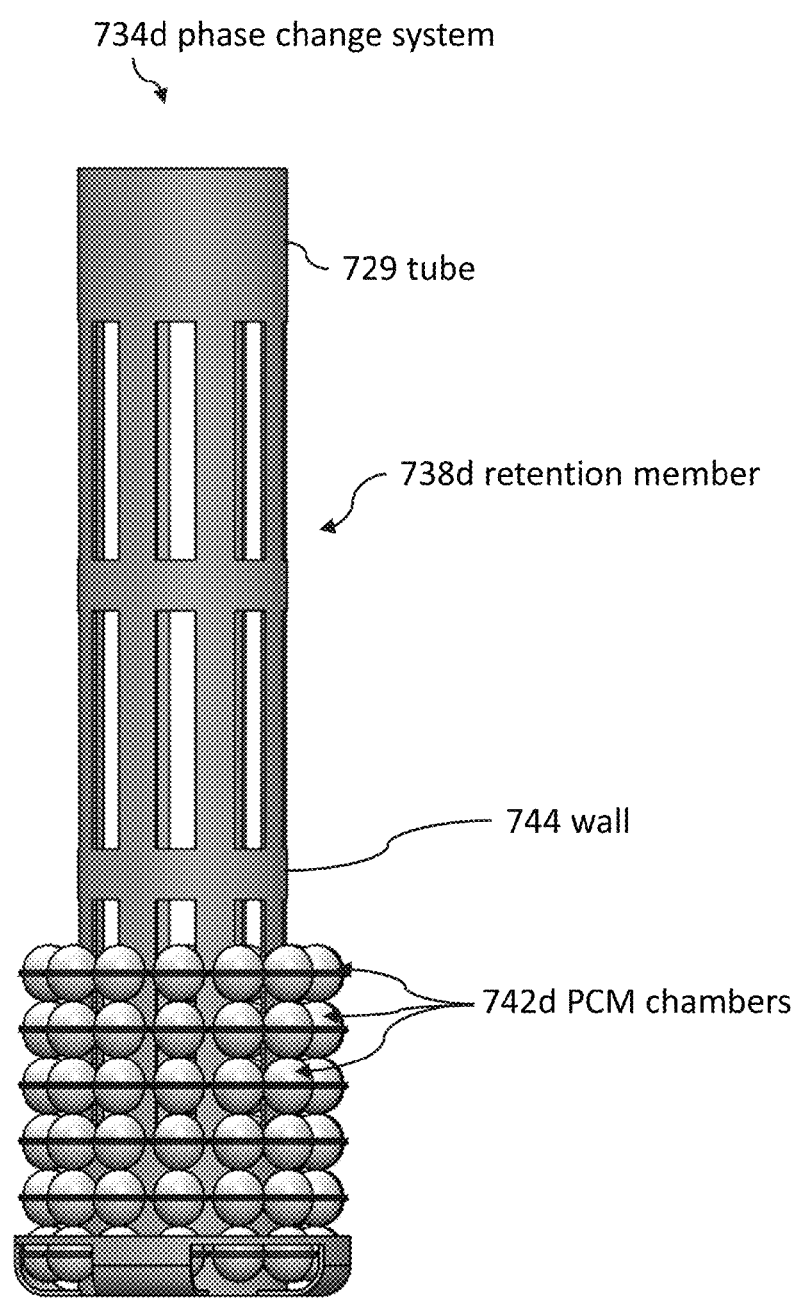
FIG. 23 illustrates a side view of a phase change system that includes a retention member and dome-shaped PCM chambers, according to some embodiments.

FIG. 23 illustrates a side view of a phase change system 734d that includes a retention member 738d (which includes a tube 729) and dome-shaped PCM chambers 742d. In some embodiments, the PCM-chambers 742d are MicroVesls (a spherical container having a multi-layer polymer structure) made by Vesl, LLC. The dome-shaped PCM chambers 742d can include fins, ridges, detents, and/or valleys configured to increase the surface area of the PCM chambers 742d to promote rapid heat transfer from the PCMs to the medicine.

Figure 24:
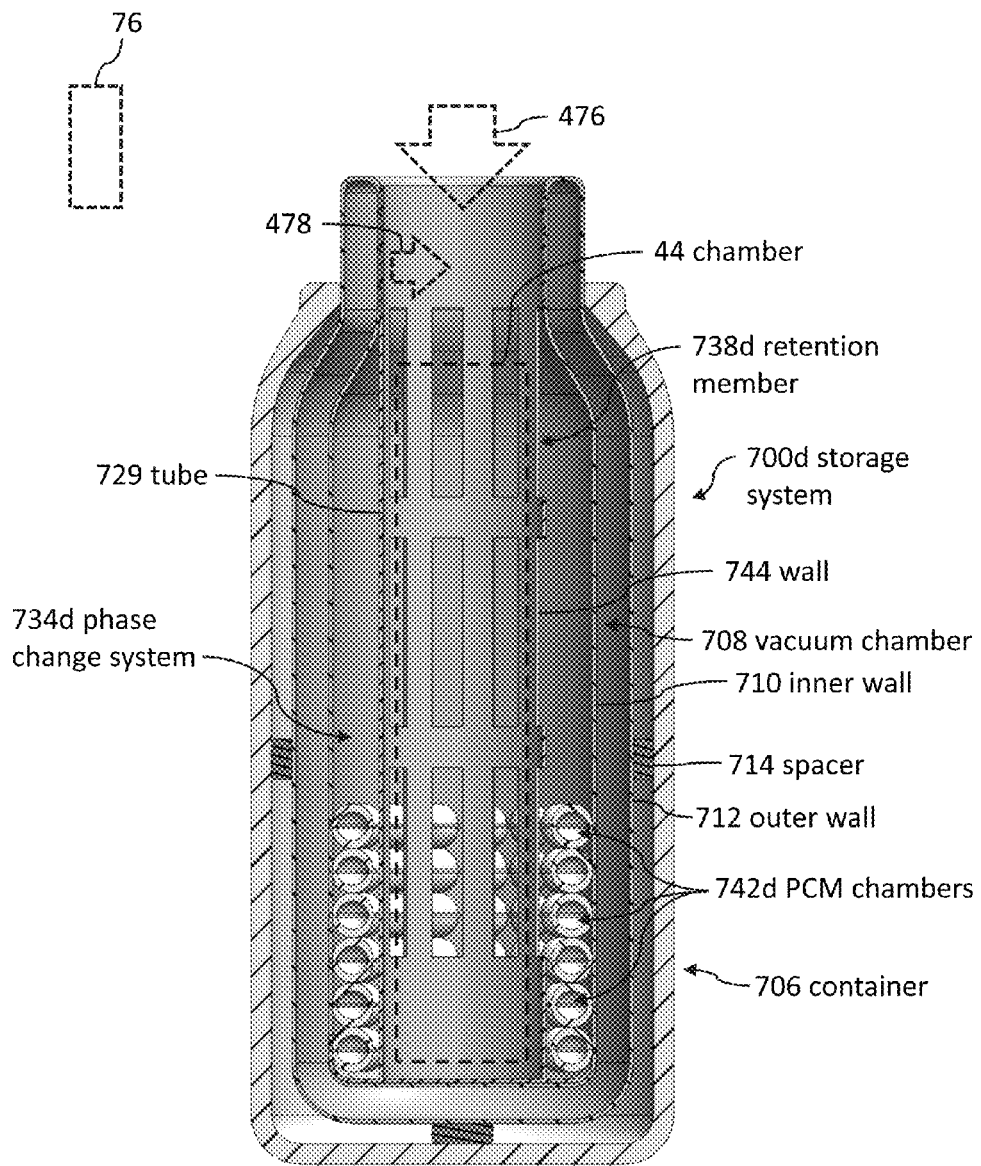
FIG. 24 illustrates the same cross section as FIG. 3 except that a phase change system is shown, according to some embodiments.

FIG. 24 illustrates the same cross section as FIG. 3 except that the phase change system 734d is shown. The dome-shaped PCM chambers 742d are located (e.g., captured) between a wall 744 of the retention member 738d and the inner wall 710 of the vacuum chamber 708. Many embodiments include more PCM chambers 742d than are shown in FIG. 24. (Not all of the PCM chambers 742d are labeled in the figures.) An inner portion of the retention member 738d is a chamber 44 to hold the medicine 702 (shown in FIG. 1).

The retention member 738d can be more flexible than the containers that form the PCM chambers 742d such that a proximal portion of the retention member 738d in the neck area of the storage system 700d can elastically deform radially inward (as shown by arrow 478). When the proximal portion of the retention member 738d is deformed radially inward, the PCM chambers 742d can be inserted in the area between the wall 744 (of the retention member 738d) and the vacuum chamber 708. The PCM chambers 742d can be free to move relative to each other (e.g., "rattle around").

Figure 25:
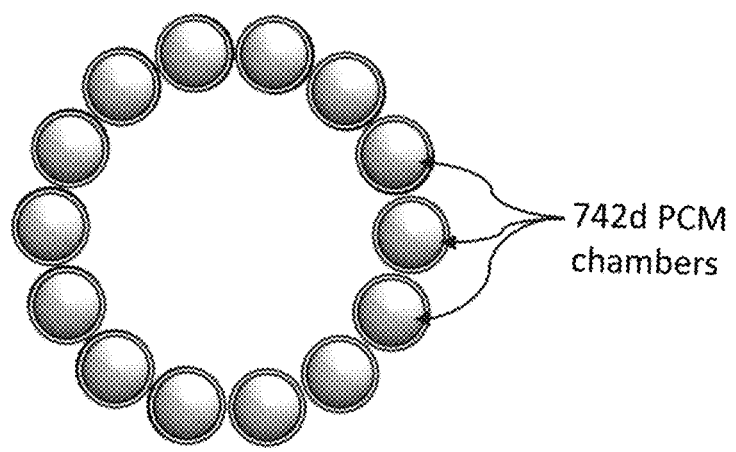
FIG. 25 illustrates a top view of dome-shaped PCM chambers, according to some embodiments.
Figure 26:
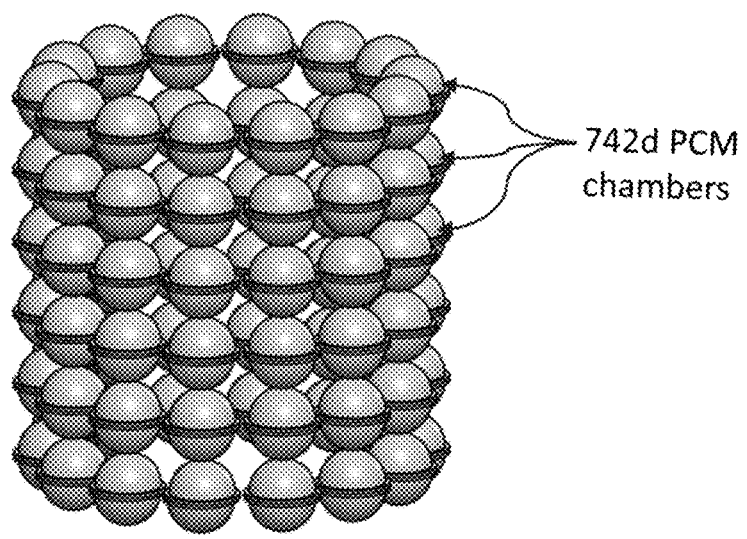
FIG. 26 illustrates a perspective view of many PCM chambers, according to some embodiments.
Figure 27:
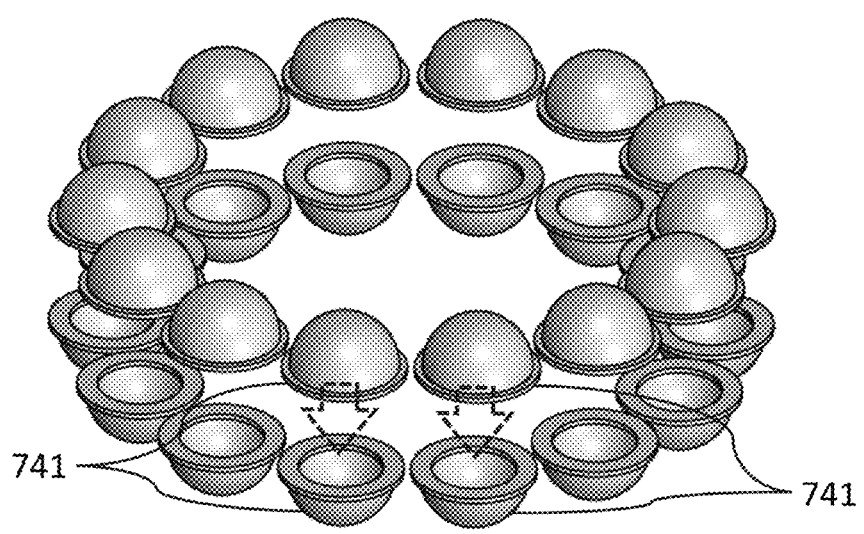
FIG. 27 illustrates dome-shaped PCM chambers prior to each half of each PCM chamber being coupled together, according to some embodiments.

FIG. 25 illustrates a top view of dome-shaped PCM chambers 742d. FIG. 26 illustrates a perspective view of many PCM chambers 742d. FIG. 27 illustrates the dome-shaped PCM chambers 742d prior to each half 741 of each PCM chamber 742d being coupled together (as indicated by the arrows in FIG. 27). Each PCM chamber 742d can be filled with PCM. Then, the two sides of the PCM chamber 742d can be coupled together (e.g., via a heating process).

Figure 28:
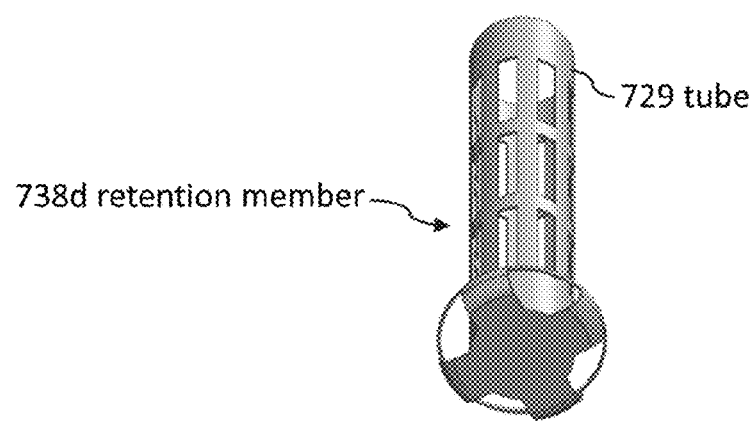
FIGS. 28-30 illustrate various perspective views of a retention member having a tube, according to some embodiments.
Figure 29:
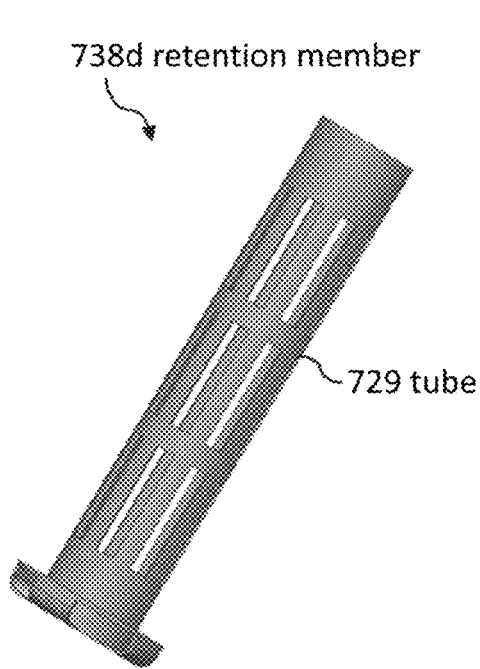
Figure 30:
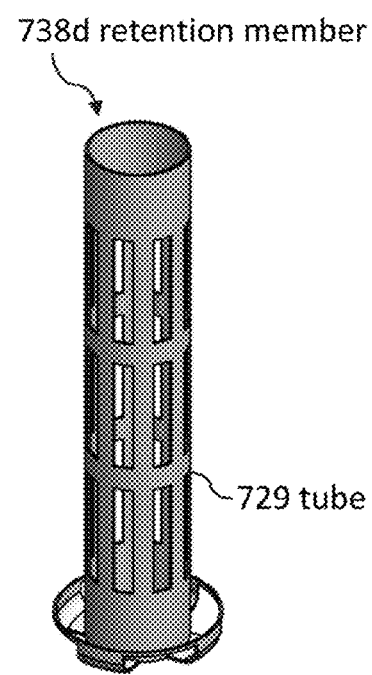

FIGS. 28-30 illustrate various perspective views of the retention member 738d. A distal portion of the retention member 738d can be wider than the neck's width 724 (shown in FIG. 3), but can be flexible to enable elastic deformation. This elastic deformation permits the distal portion of the retention member 738d to move through the neck 722 (shown in FIG. 3) and then spring radially outward to a width that is wider than the width 724 of the neck 722.

Referring now to FIGS. 23-30, in several embodiments, a medicine storage system 700d comprises an insulated container 706 having an opening; a first lid 704, 704k (shown in FIGS. 3 and 67) configured to cover the opening; a phase change system 734d located inside the insulated container; a medicine storage area (e.g., 44) located inside the insulated container; and a first retention member 738d located inside the insulated container 706 and configured to prevent the phase change system 734d from blocking access to the medicine storage area. For example, if the PCM chambers 742d fall into the medicine storage area, the PCM chambers 742d can block a user from inserting the medicine into the medicine storage area (which can be a cavity inside the tube 729). As shown in FIG. 24, the storage system 700d can be configured to provide access for inserting a medicine through the opening and into the medicine storage area.

The spheres shown in FIG. 25 are containers that form PCM chambers 742d. The phase change system 734d (shown in FIGS. 23 and 24) comprises a first container having a first phase change material and a second container having a second phase change material. The first and second containers can be spherical, cylindrical, or any other suitable shape. The first phase change material can have a first melting temperature greater than 40 degrees Fahrenheit and less than 74 degrees Fahrenheit. The second phase change material can have a second melting temperature greater than 74 degrees Fahrenheit and less than 100 degrees Fahrenheit.

In some embodiments, the first retention member comprises a tube 729 located inside the insulated container 706 such that the tube 729 is in fluid communication with the opening. The storage system 700d can be configured to enable inserting the medicine through the opening and into the tube 729. The tube 729 can extend from a distal portion of the insulated container 706 to a proximal portion of the insulated container 706. The first and second containers can be located between an inner wall 710 of the insulated container and an outer wall of the tube 729.

In several embodiments, the storage system further comprises a plurality of containers at least partially filled with at least one of the first phase change material and the second phase change material. As shown in FIGS. 23, 24, and 26, the plurality of containers are not coupled to each other such that the plurality of containers are movable within an area between the inner wall 710 of the insulated container and the outer wall of the tube 729.

FIG. 31 illustrates a bottom view of a phase change system 734e that includes a retention member 738e that has radially outward protrusions that separate containers having PCM chambers 742e. The containers having PCM chambers 742e can include fins, valleys, detents, and other features to increase the surface area of the PCM chambers 742e (to promote heat transfer).

Figure 33:
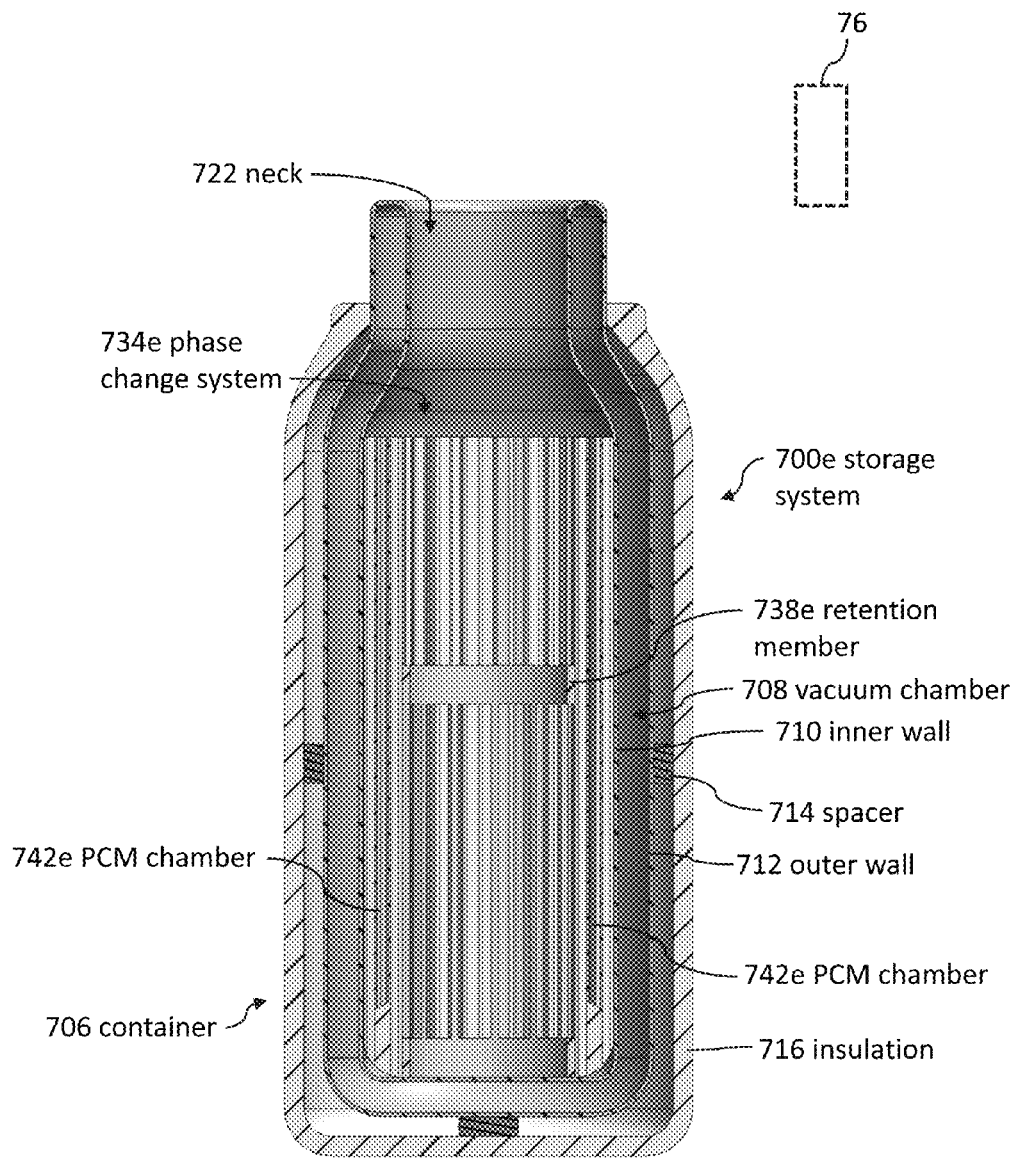
FIG. 33 illustrates the same cross section as FIG. 3 except that a phase change system is shown and the lid is hidden, according to some embodiments.

The retention member 738e can be more flexible than the containers having PCM chambers 742e to enable the retention member 738e to deform during insertion of the containers having PCM chambers 742e through the neck 722 and into an interior portion of the storage system 700e (shown in FIG. 33). In some embodiments, the containers having PCM chambers 742e are flexible to enable the PCM chambers 742e to deform during insertion of the containers having PCM chambers 742e through the neck 722 and into an interior portion of the storage system 700e.

Figure 32:
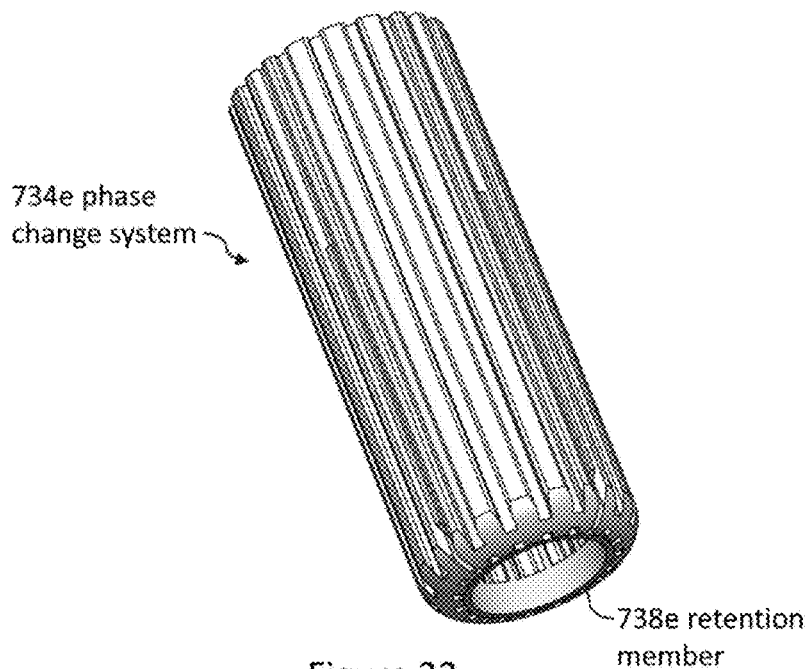
FIG. 32 illustrates a perspective view of a phase change system, according to some embodiments.

FIG. 32 illustrates a perspective view of the phase change system 734e. FIG. 33 illustrates the same cross section as FIG. 3 except that the phase change system 734e is shown and the lid 704 is hidden. The embodiment shown in FIG. 33 can use the lid 704k shown in FIGS. 66, 69, 70, and 75-78.

Figure 34:
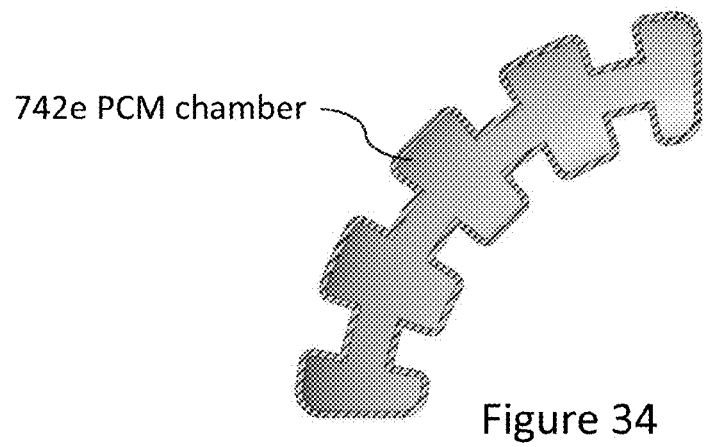
FIG. 34 illustrates a cross-sectional view taken along line 34-34 from FIG. 35, according to some embodiments.
Figure 35:
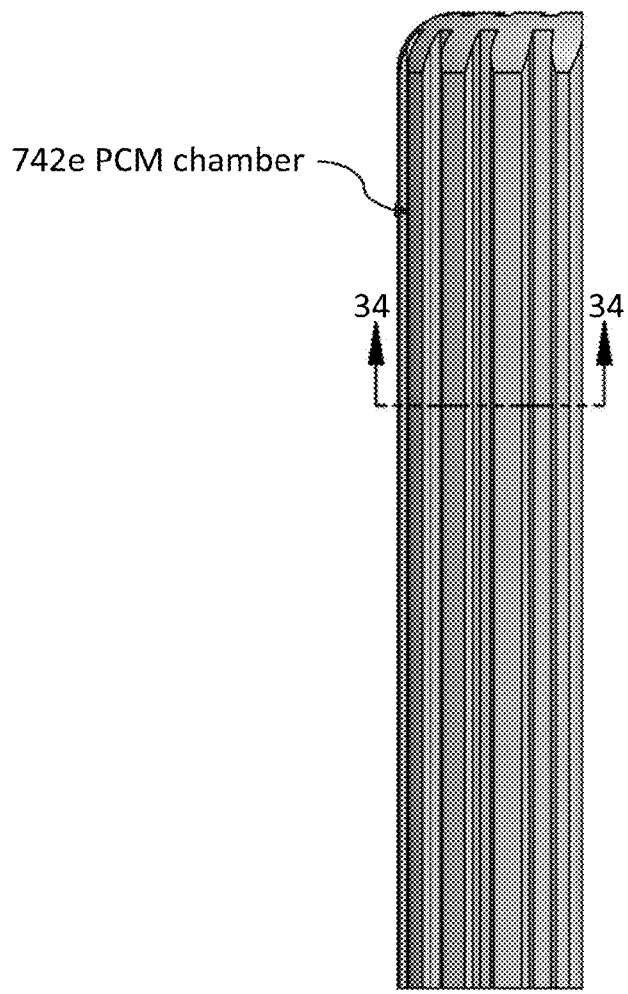
FIG. 35 illustrates a side view of a container having a PCM chamber, according to some embodiments.
Figure 36:
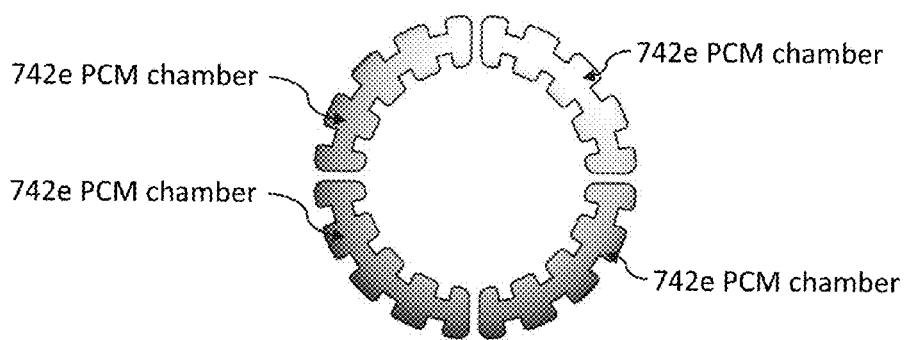
FIG. 36 illustrates a bottom view of four containers, according to some embodiments.
Figure 37:
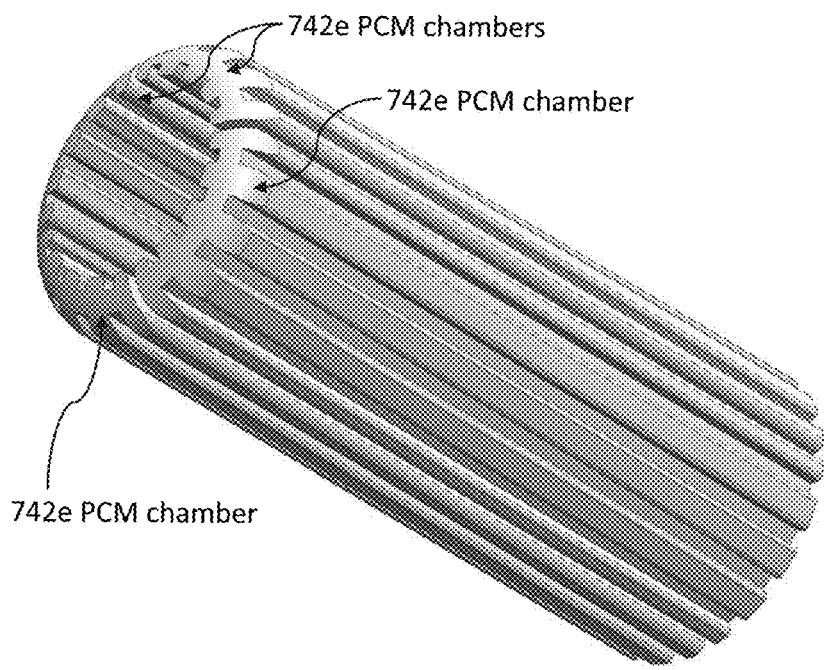
FIG. 37 illustrates a perspective view of containers shown in FIG. 36, according to some embodiments.
Figure 38:
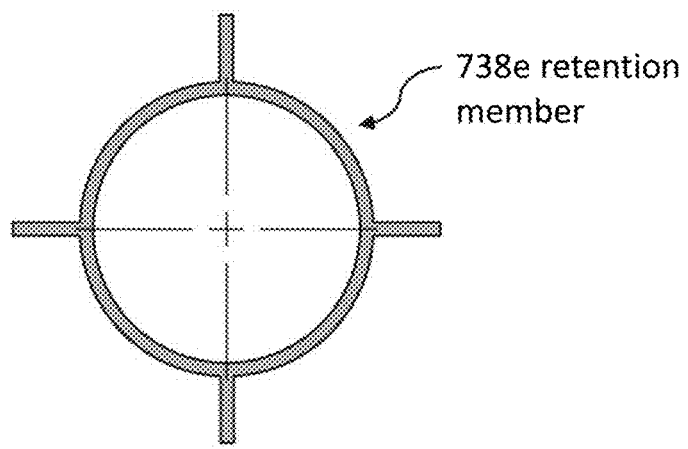
FIG. 38 illustrates a top view of a retention member, according to some embodiments.
Figure 39:
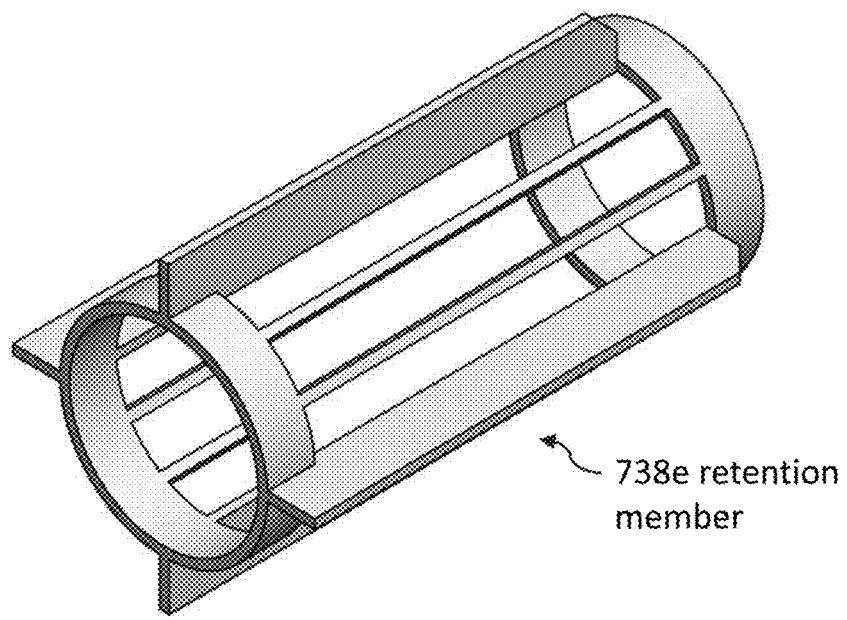
FIG. 39 illustrates a perspective view of a retention member, according to some embodiments.

FIG. 34 illustrates a cross-sectional view taken along line 34-34 from FIG. 35. FIG. 34 shows that the surface area is increased by the surface features of the container having the PCM chamber 742e. FIG. 35 illustrates a side view of the container having the PCM chamber 742e. FIG. 36 illustrates a bottom view of four containers. Each container has at least one PCM chamber 742e. FIG. 37 illustrates a perspective view of the containers shown in FIG. 36. FIG. 38 illustrates a top view of the retention member 738e shown in FIGS. 31-33. FIG. 39 illustrates a perspective view of the retention member 738e.

Figure 40:
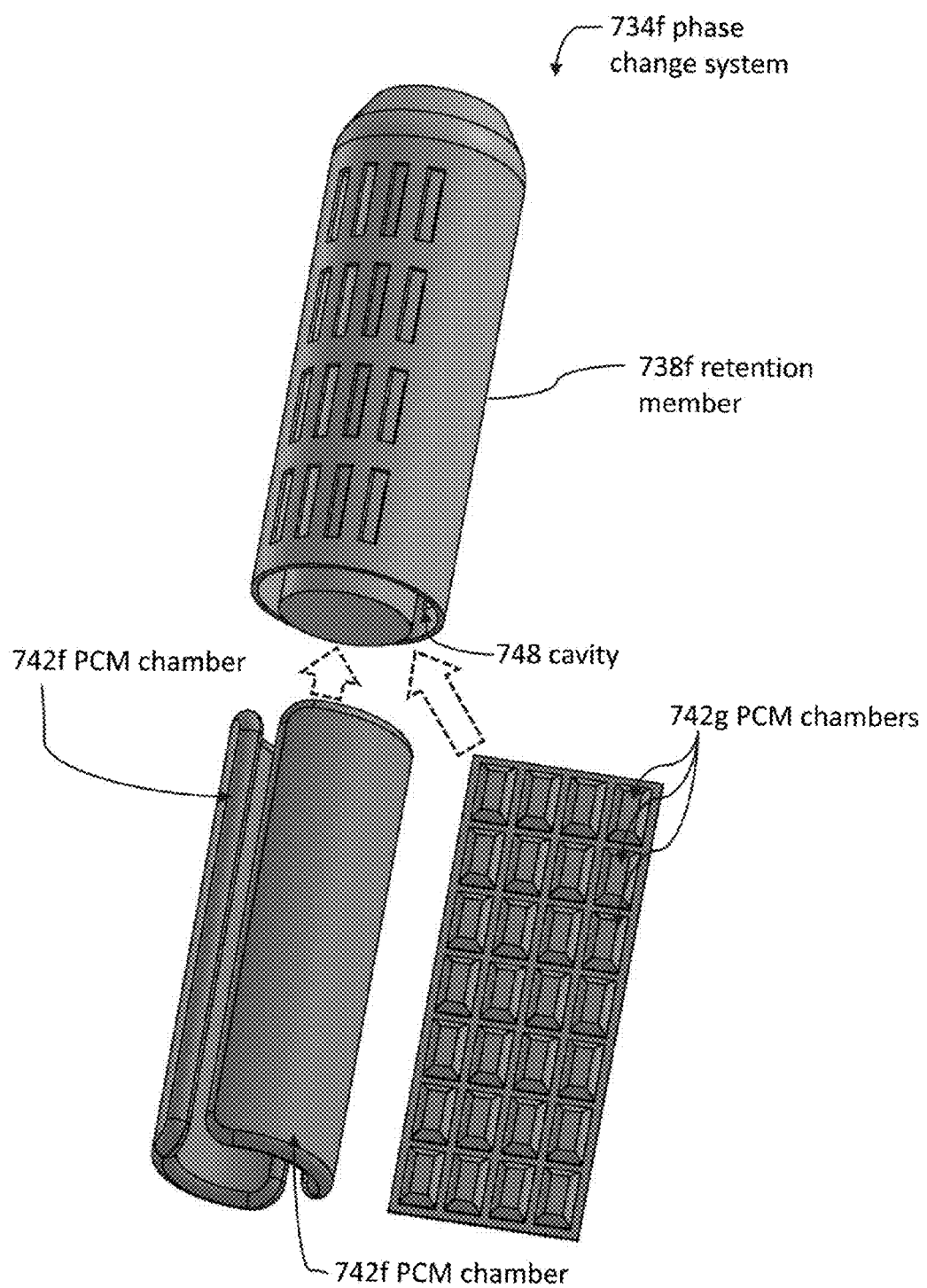
FIG. 40 illustrates a perspective view of a phase change system that includes a tubular retention member that has holes to promote airflow and heat transfer from an area having the medicine to an area having the PCM chambers, according to some embodiments.
Figure 41:
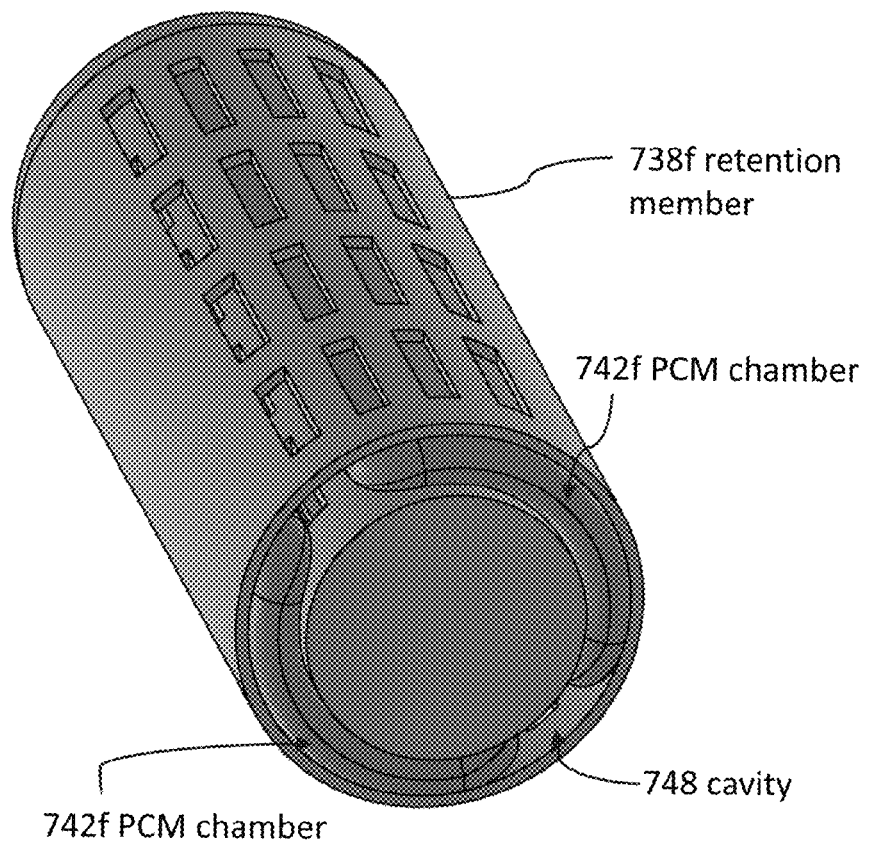
FIG. 41 illustrates a perspective view of a bag filled with PCM and inserted into a cavity of a retention member, according to some embodiments.
Figure 42:
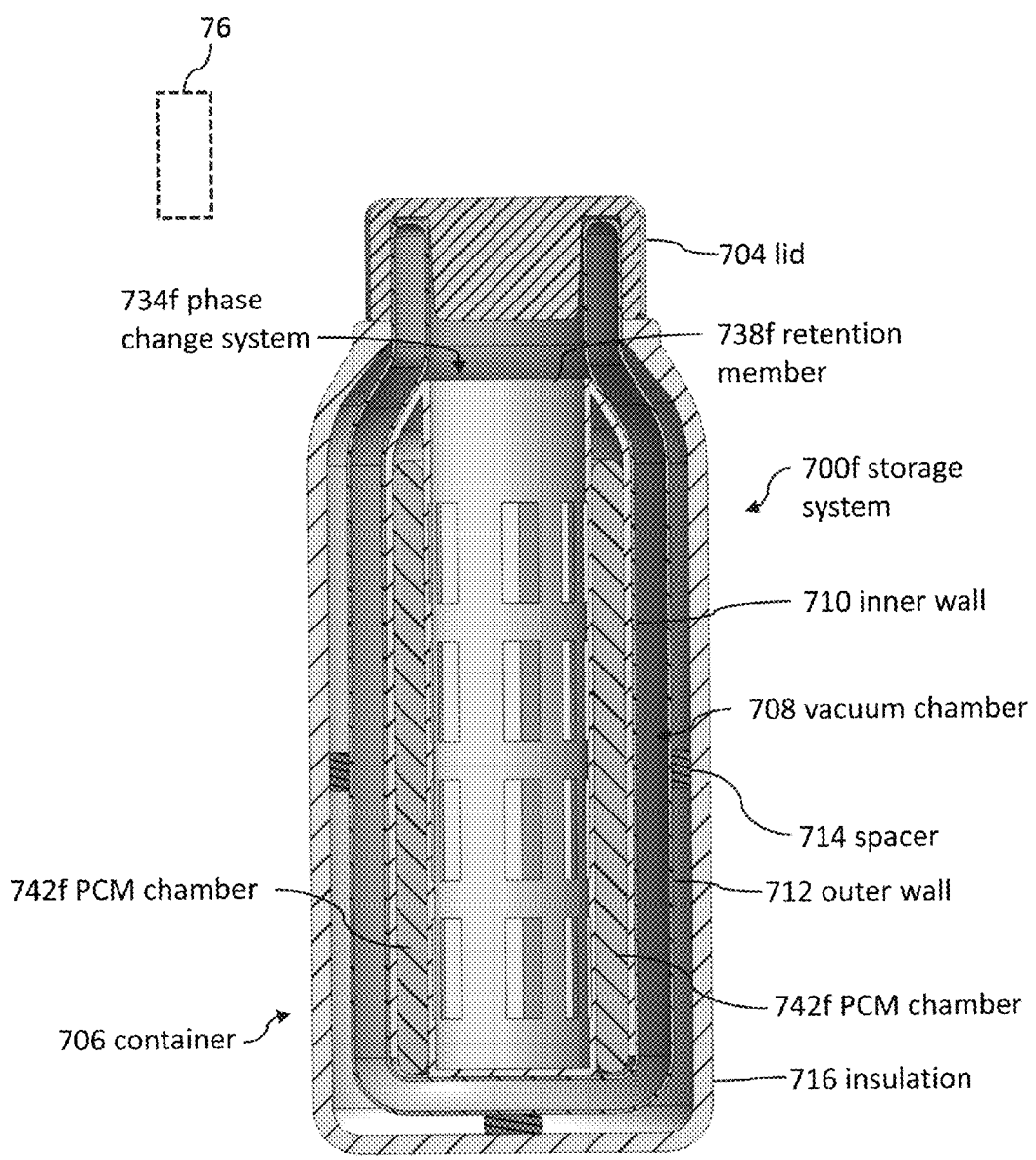
FIG. 42 illustrates the same cross section as FIG. 3 except that a phase change system is shown, according to some embodiments.

FIG. 40 illustrates a perspective view of a phase change system 734f that includes a retention member 738f that has holes to promote airflow and heat transfer from an area having the medicine 702 (shown in FIG. 3) to an area having the PCM chambers 742f and/or the PCM chambers 742g. The PCM chambers 742f and/or the PCM chambers 742g can fit inside a cavity 748 of the retention member 738f (e.g., as shown in FIGS. 41 and 42).

The PCM chamber 742f can be a highly flexible pouch made from multiple layered film, filled with PCM, and hermetically sealed to prevent leakage or intrusion (e.g., a PackVesl made by Vesl, LLC). The PCM chamber 742g can be a highly-flexible, multi-layer barrier film sheet having blisters filled with PCM and hermetically sealed to prevent leakage or intrusion (e.g., a MatVesl made by Vesl, LLC).

The PCM chamber 742g can be any suitable dimension. In some embodiments, each pouch (e.g., each PCM chamber 742g) can have a width of at least 15 millimeters and/or less than 45 millimeters. In some embodiments, each pouch (e.g., each PCM chamber 742g) can have a length of at least 30 millimeters, less than 80 millimeters, and/or less than 200 millimeters.

The PCM chamber 742f can be much larger than the PCM chamber 742g. In some embodiments, the PCM chamber 742f has a width of at least 40 millimeters and/or less than 150 millimeters. In several embodiments, the PCM chamber 742f has a length of at least 80 millimeters and/or less than 200 millimeters.

FIG. 41 illustrates a perspective view of a pouch filled with PCM inserted into a cavity 748 of the retention member 738f. The PCM chambers 742f, 742g shown in FIG. 40 can be inserted into the cavity 748 as shown in FIG. 41.

FIG. 42 illustrates the same cross section as FIG. 3 except that the phase change system 734f is shown. FIGS. 43-45 illustrate various views of the retention member 738f. FIGS. 46-48 illustrate various views of PCM chambers 742g made from a highly-flexible, multi-layer barrier film sheet having blisters filled with PCM and hermetically sealed to prevent leakage or intrusion (e.g., a MatVesl made by Vesl, LLC).

Referring now to FIG. 47, some of the chambers 742g can be filled with a first PCM and some of the chambers 742g can be filled with a second PCM that has a different melting temperature than the melting temperature of the first PCM. In several embodiments, some of the chambers 742g are filled with PureTemp 18 (having a melting temperature of approximately 18 degrees Celsius) and some of the chambers 742g are filled with PureTemp 28 (having a melting temperature of approximately 28 degrees Celsius). Thus, one flexible sheet can contain pouches having two different types of PCMs that are fluidly isolated from each other but are mechanically coupled.

At least one of the PCMs can be colored (e.g., via a dye) to help people visually differentiate one PCM type having a first color from another PCM type having a second color. Thus, factory workers can see what type of PCM is located in a chamber 742g of a clear pouch.

Referring now to FIG. 40, several embodiments include a first flexible sheet with PCM chambers 742g (e.g., having a first PCM type) and include a second flexible sheet with PCM chambers 742g (e.g., having a second PCM type). Both flexible sheets can be held in place by a retention member 738f such that the flexible sheets are located at least partially between the retention member 738f and an inner wall 710 of a vacuum flask (e.g., as shown in FIG. 42).

FIG. 49 illustrates a perspective view of a phase change system 734h that has an offset hole to hold the medicine 702. FIG. 50 illustrates a top view of the phase change system 734h shown in FIG. 49. The hole (e.g., a cavity 750) in which at least a portion of the medicine is located is radially offset from a center of the storage system 700h shown in FIG. 52.

Figure 51:
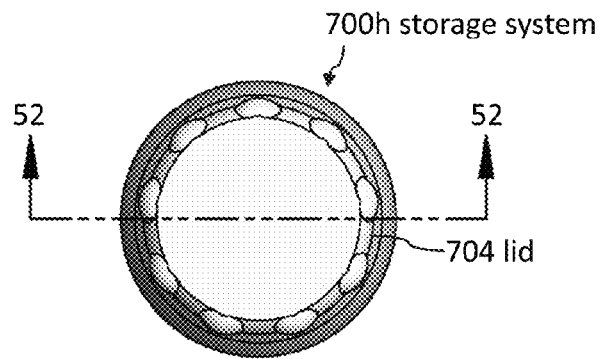
FIG. 51 illustrates a top view of a medicine storage system, according to some embodiments.

FIG. 51 illustrates a top view of the storage system 700h. FIG. 52 illustrates a cross-sectional view taken along line 52-52 in FIG. 51.

Figures 53, 54:
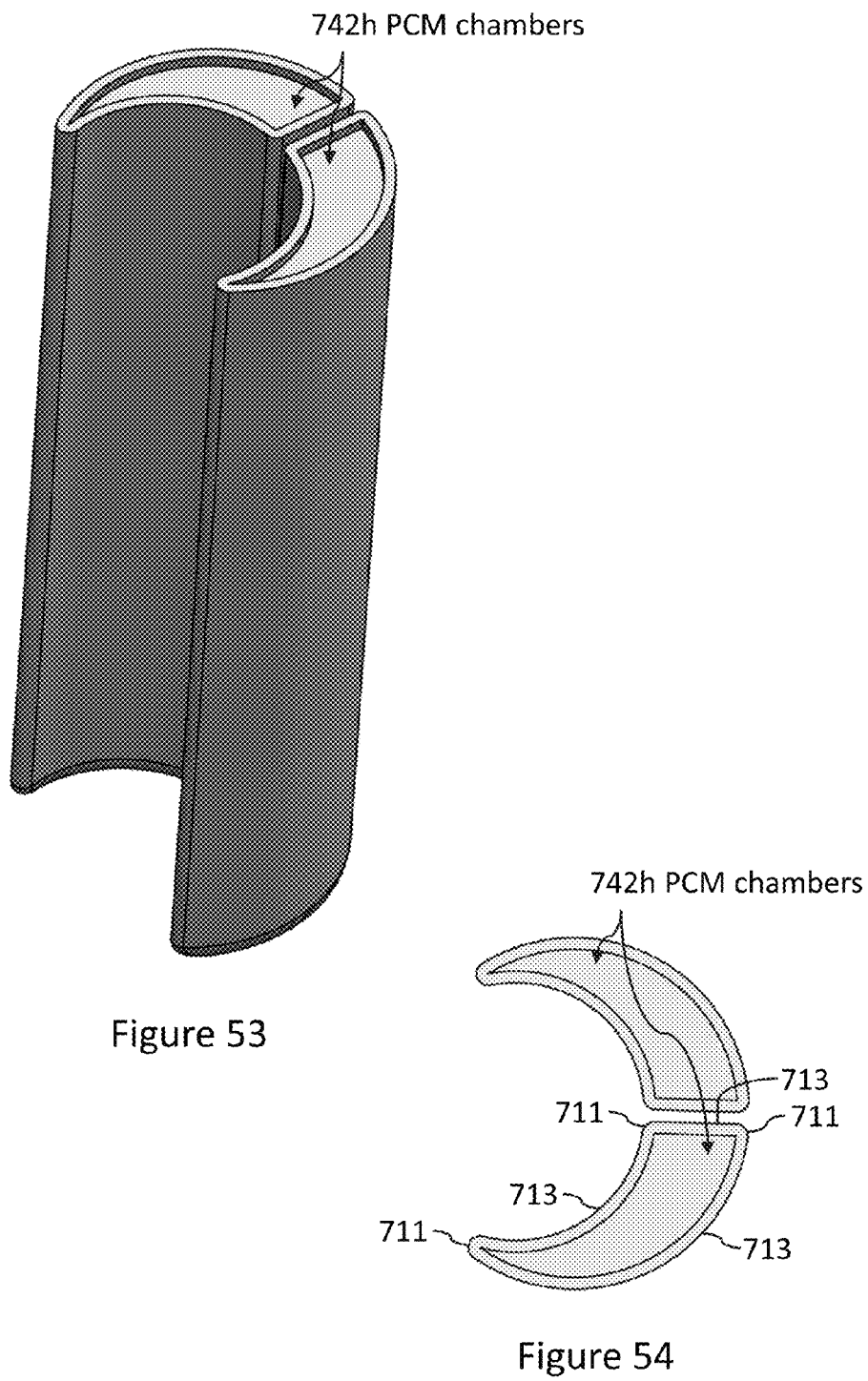
FIG. 53 illustrates a perspective view of two containers, according to some embodiments.
FIG. 54 illustrates a top view of PCM containers, according to some embodiments.
Figure 55:
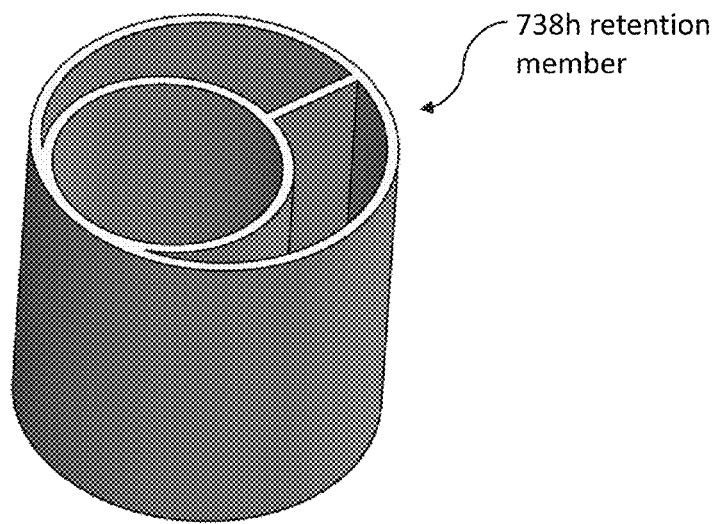
FIG. 55 illustrates a perspective view of a retention member, according to some embodiments.
Figure 56:
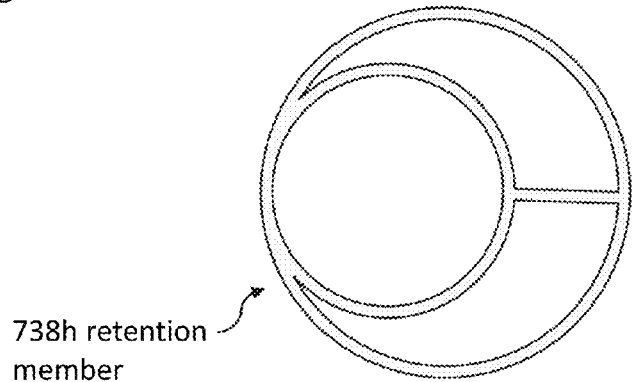
FIG. 56 illustrates a top view of a retention member, according to some embodiments.

FIG. 53 illustrates a perspective view of two containers. Each container includes a PCM chamber 742h. The PCM chambers 742h can have PCMs with the same melting temperature or different melting temperatures. FIG. 54 illustrates a top view of the containers shown in FIG. 53. FIG. 55 illustrates a perspective view of the retention member 738h shown in FIG. 49. FIG. 56 illustrates a top view of the retention member 738h shown in FIG. 49.

Any of the embodiments described herein can include a rigid outer housing or a flexible outer housing. In some cases, people prefer a flexible outer housing. In some cases, people prefer a rigid outer housing.

FIG. 57 illustrates a perspective view of a storage system 700*i* having a flexible outer housing, which can be made from fabric, rubber, neoprene, urethane, vinyl, nylon, and/or polyester. In some embodiments, the outer housing is thermoplastic polyurethane coated nylon with radio frequency welded seams. The storage system 700*i* can also include ethylene vinyl acetate foam.

Figure 58:
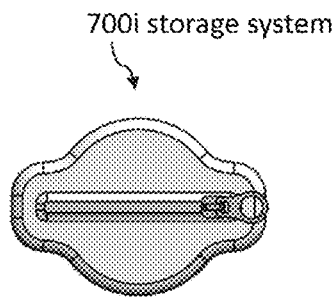
FIG. 58 illustrates a top view of a medicine storage system, according to some embodiments.
Figure 59:
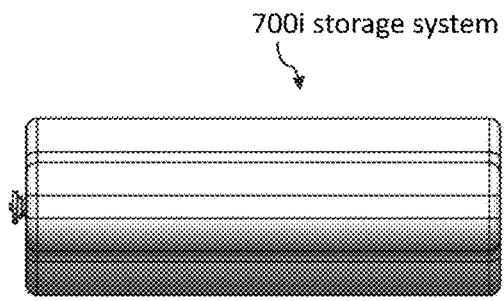
FIG. 59 illustrates a side view of a medicine storage system, according to some embodiments.
Figure 60:
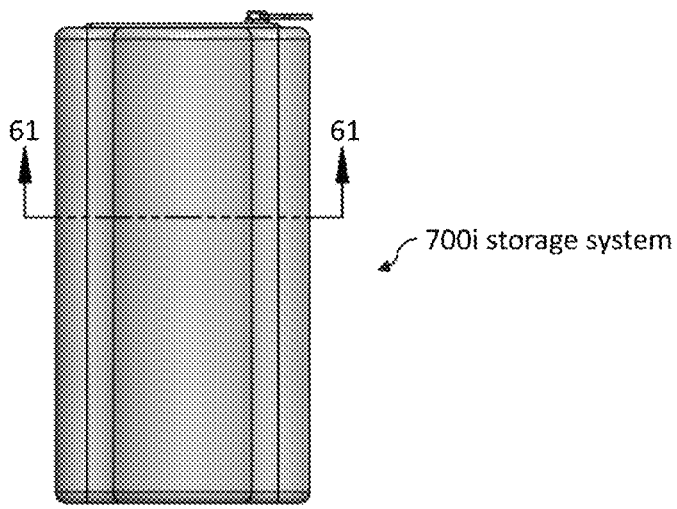
FIG. 60 illustrates a front view of a medicine storage system, according to some embodiments.

The storage system 700*i* includes a waterproof zipper 746. Opening the zipper 746 provides access to the medicine chamber 44*i* shown in FIG. 61. FIG. 58 illustrates a top view of the storage system 700*i*. FIG. 59 illustrates a side view of the storage system 700*i*. FIG. 60 illustrates a front view of the storage system 700*i*.

Figure 61:
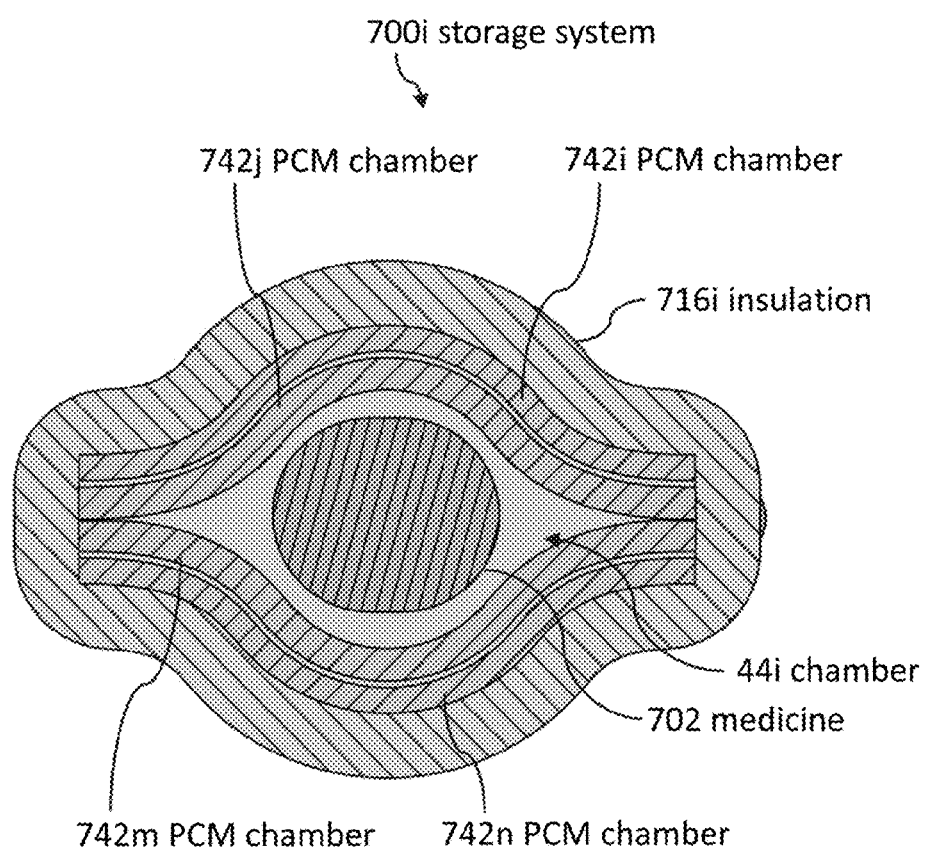
FIG. 61 illustrates a cross-sectional view taken along line 61-61 shown in FIG. 60, according to some embodiments.

FIG. 61 illustrates a cross-sectional view taken along line 61-61 shown in FIG. 60. Embodiments of the storage system 700*i* can include a first PCM on a first side of the medicine 702 and a second PCM on a second side of the medicine 702. The embodiment shown in FIG. 61 includes PCM in PCM chambers 742*j*, 742*m*, which can have lower melting temperatures than PCM in PCM chambers 742*i*, 742*n*. PCM in PCM chambers 742*j*, 742*m* can have melting temperatures greater than 40 degrees Fahrenheit and less than 74 degrees Fahrenheit. PCM in PCM chambers 742*i*, 742*n* can have melting temperatures greater than 74 degrees Fahrenheit and less than 100 degrees Fahrenheit.

PCM in PCM chambers 742*i*, 742*n* can be located radially outward from PCM in PCM chambers 742*j*, 742*m* such that, at 74 degrees Fahrenheit (e.g., room temperature), the PCM at least partially surrounding the chamber 44*i* having the medicine 702 is liquid and the PCM located radially outward from the liquid PCM is frozen. In some cases, this configuration is advantageous because the medicine 702 and/or the user's fingers are protected from frozen PCM (which is hard) by liquid PCM (which is comfortably compliant).

Figure 62:
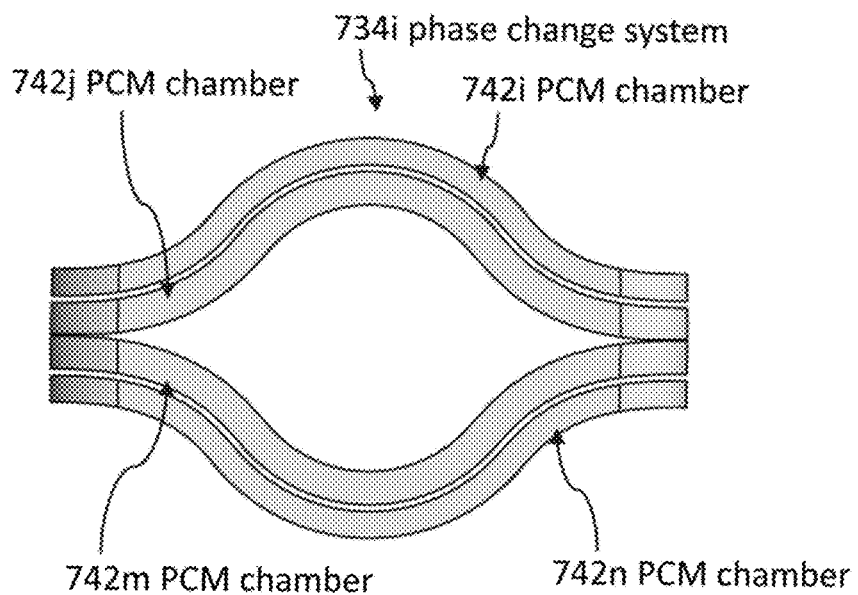
FIG. 62 illustrates a top view of PCM chambers, which can be located in pouches, according to some embodiments.
Figure 63:
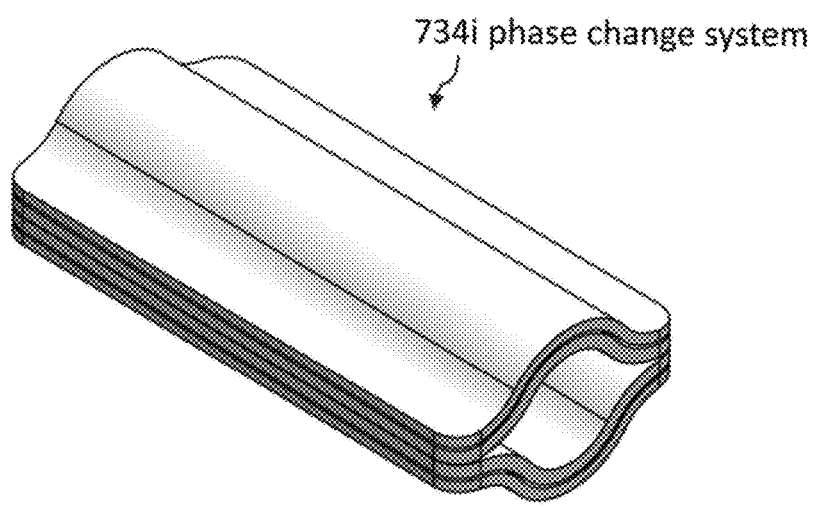
FIG. 63 illustrates a perspective view of a phase change system, according to some embodiments.

FIG. 62 illustrates a top view of the PCM chambers 742*i*, 742*n*, 742*j*, 742*m*, which can be located in pouches. The pouches can be made from multiple layered film, filled with PCM, and hermetically sealed to prevent leakage or intrusion (e.g., a PackVesl made by Vesl, LLC). The PCM chambers 742*i*, 742*n*, 742*j*, 742*m* can be formed by a highly-flexible, multi-layer barrier film sheet having blisters filled with PCM and hermetically sealed to prevent leakage or intrusion (e.g., a MatVesl made by Vesl, LLC). FIG. 63 illustrates a perspective view of the phase change system 734*i*.

Figure 64:
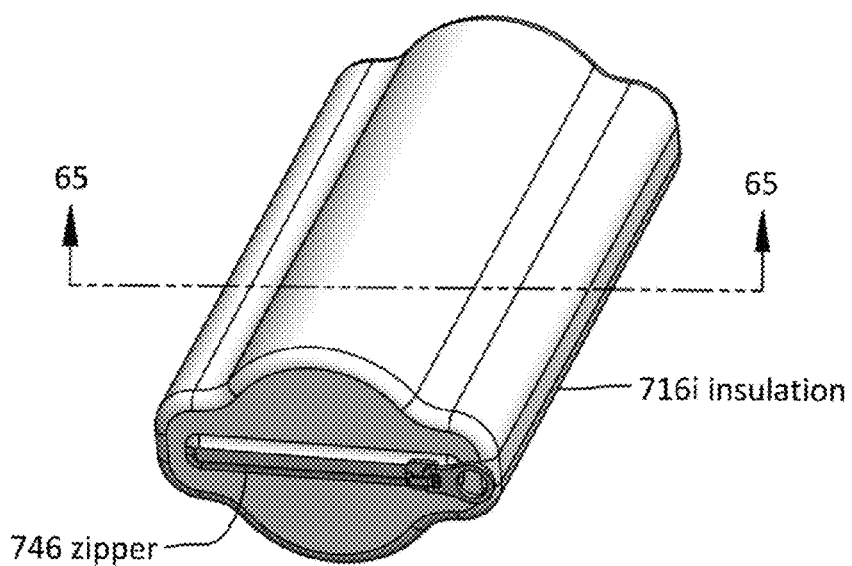
FIG. 64 illustrates a perspective view of insulation and a zipper, according to some embodiments.
Figure 65:
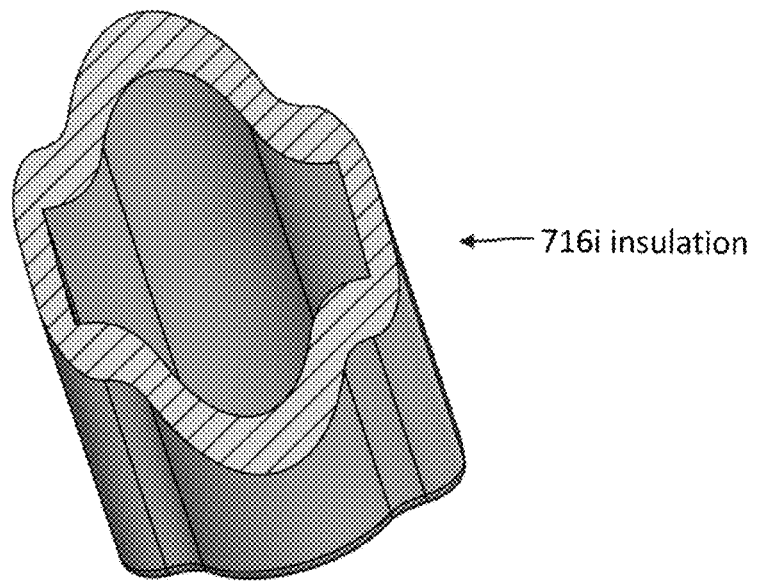
FIG. 65 illustrates a cross-sectional view taken along line 65-65 from FIG. 64, according to some embodiments.

FIG. 64 illustrates a perspective view of the insulation 716*i* and the zipper 746. FIG. 65 illustrates a cross-sectional view taken along line 65-65 from FIG. 64.

FIGS. 66-79 illustrate various embodiments that can be combined with any features, elements, structures, assemblies, chemistries, steps, methods, and innovations described in the contexts of other embodiments described herein and/or incorporated by reference herein.

A container 706*k* can be insulated by a vacuum chamber, insulation, and/or by any other suitable insulation. A lid 704*k* can cover an opening of the container 706*k*. The lid 704*k* can include features configured to enable a user to apply an unscrewing torque that is greater than the a screwing torque to increase the likelihood that a user will be able to unscrew the lid 704*k* from the container 706*k*. The lid 704*k* can include unique sealing and insulation structures to reduce the heat transfer permitted by the lid 704*k*.

The container 706*k* can also include a narrow neck area to reduce the area that is not insulated by the container 706*k* (e.g., not insulated by a vacuum chamber). The narrow neck can greatly improve the overall thermal performance of the storage system 700*k*. The flexible nature of various components inside the container 706*k* can enable the components to be inserted through the narrow neck and then expand into place once inside an interior of the container 706*k*. The interior can have a larger diameter than the neck.

Figure 70:
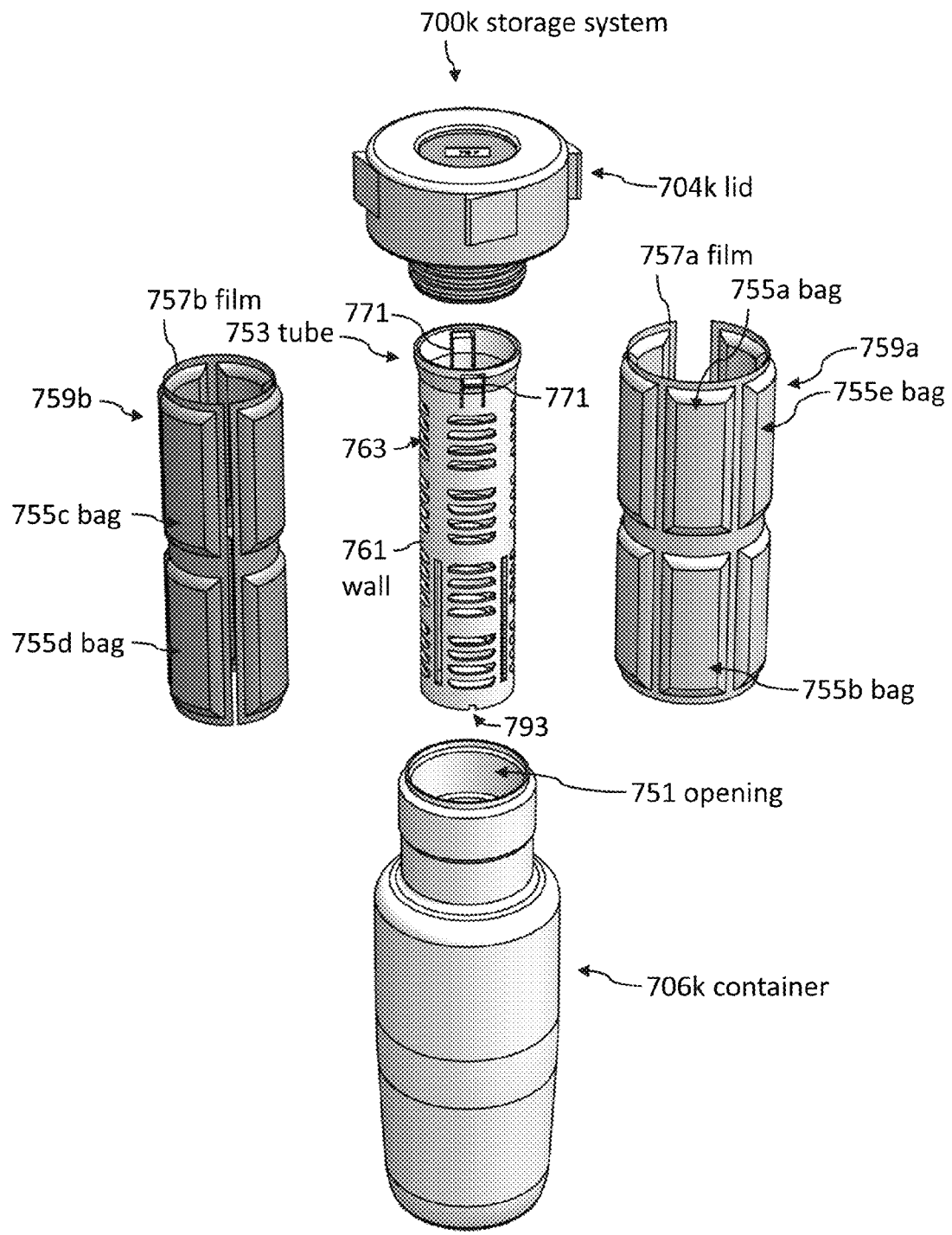
FIG. 70 illustrates a perspective view of a medicine storage system in a disassembled state, according to some embodiments.

FIG. 68 illustrates a side view of the storage system 700*k*. FIG. 69 illustrates a cross-sectional view taken along line 69-69 in FIG. 68. FIG. 70 illustrates a perspective view of the storage system 700*k* in a disassembled configuration.

Referring now to FIGS. 69 and 70, the storage system 700*k* comprises an insulated container 706*k* having an opening 751. A lid 704*k* is configured to cover the opening 751.

Referring now to FIG. 69, the storage system 700*k* also comprises a phase change system 734*k* and a tube 753. The tube 753 can be rigid or flexible. The tube 753 can be molded from plastic.

The phase change system 734*k* is located inside the insulated container 706*k*. The tube 753 is located inside the insulated container 706*k* such that the tube 753 is in fluid communication with the opening 751 (shown in FIG. 70) to enable inserting a medicine 702 through the opening 751 and into the tube 753.

Many different types of insulated containers can be used. The insulated container 706*k* can be a vacuum flask having stainless steel walls and a vacuum chamber 708*k* located between the stainless steel walls (e.g., between the inner wall 710*k* and the outer wall 712*k*). The insulated container 706*k* can be a rigid shell surrounded by foam insulation. The insulated container 706*k* can be a compliant bag made from fabric and insulated with any suitable insulation material.

FIG. 70 illustrates flexible bags 755*a-e*, which can be at least partially filled with any of the phase change materials described herein and/or incorporated by reference. In some embodiments, some of these flexible bags 755*a-e* are filled with a first phase change material that has a first melting temperature greater than 40 degrees Fahrenheit and less than 74 degrees Fahrenheit; and the rest of the flexible bags 755*a-e* are filled with a second phase change material that has a second melting temperature greater than 74 degrees Fahrenheit and less than 100 degrees Fahrenheit. (Not all of the flexible bags are labeled to increase the clarity of the figures.)

In some embodiments, a flexible bag 755*a* is filled with a first phase change material that has a first melting temperature greater than 40 degrees Fahrenheit and less than 74 degrees Fahrenheit, and flexible bags 755*b*, 755*e* are filled with a second phase change material that has a second melting temperature greater than 74 degrees Fahrenheit and less than 100 degrees Fahrenheit. In this embodiment, flexible bags 755*a*, 755*b*, 755*e* are mechanically coupled to each other, but fluidly isolate the first phase change material from the second phase change material.

In some embodiments, flexible bags 755*a*, 755*b*, 755*e* are filled with a first phase change material that has a first melting temperature greater than 40 degrees Fahrenheit and less than 74 degrees Fahrenheit, and flexible bags 755*c*, 755*d* are filled with a second phase change material that has a second melting temperature greater than 74 degrees Fahrenheit and less than 100 degrees Fahrenheit.

In some embodiments, flexible bags 755*c*, 755*d* are filled with a first phase change material that has a first melting temperature greater than 40 degrees Fahrenheit and less than 74 degrees Fahrenheit, and flexible bags 755*a*, 755*b*, 755*e* are filled with a second phase change material that has a second melting temperature greater than 74 degrees Fahrenheit and less than 100 degrees Fahrenheit.

The flexible bags 755a, 755b, 755e (or 755c, 755d) can be made from one piece of film 757a (or 757b) that has multiple chambers at least partially filled with PCM. Each bag 755a-e has a PCM chamber. Each chamber can hold a different type of phase change material. In some embodiments, twelve chambers hold a first PCM and ten chambers hold a second type of PCM. The flexible bags can be made from multiple layers of film. The separate chambers can be made by sealing portions of the film together. The film can be a sheet of any waterproof material.

The film 757a, which forms the bags (e.g., 755a, 755b, 755e) can create a PCM blanket 759a that is flexible and rollable. The blanket 759a has PCM chambers and very thin sections of film that do not include PCM. The film sheets can enable the first blanket 759a to be rolled (e.g., moved from a flat orientation to a rolled orientation) to facilitate inserting the blanket 759a into a narrow opening 751. Once the blanket 759a has passed through the narrow opening 751, the blanket 759 can expand (e.g., at least partially unroll) to enable inserting the tube 753 into a middle portion of the container 706k such that the blanket 759a at least partially wraps around the tube 753.

The film 757b, which forms the bags (e.g., 755c, 755d) can create a PCM blanket 759b that is flexible and rollable. The blanket 759b has PCM chambers and very thin sections of film that do not include PCM. After the first blanket 759a is inserted into the container 706k, the second blanket 759b can be inserted into the container 706k (e.g., prior to inserting the tube 753 into the container 706k). The second blanket 759b can be located at least partially between the tube 753 and the first blanket 759a such that the second PCM blanket 759b at least partially wraps around the tube 753 and such that the first PCM blanket 759a at least partially wraps around the second PCM blanket 759b and at least partially wraps around the tube 753.

In some embodiments, the phase change system 706k comprises a first flexible bag 755a having a first phase change material and a second flexible bag 755c having a second phase change material. The first phase change material can have a first melting temperature greater than 40 degrees Fahrenheit and less than 74 degrees Fahrenheit. The second phase change material can have a second melting temperature greater than 74 degrees Fahrenheit and less than 100 degrees Fahrenheit.

In some embodiments, the phase change system is configured to protect the medicine 702 (shown in FIG. 69) from a first external temperature less than a minimum recommended storage temperature and from a second external temperature greater than a maximum recommended storage temperature by utilizing phase changes to regulate a temperature of the medicine 702.

Referring now to FIG. 69, the medicine 702 can be any type of medicine. In some embodiments, the medicine 702 is an injection device having epinephrine. The injection device can be located in the tube 753.

In several embodiments, the first flexible bag 755a and the second flexible bag 755c are located inside the insulated container 706k and are located outside the tube 753 such that the first flexible bag 755a and the second flexible bag 755c are located between an inner wall 710k of the insulated container 706k and an outer wall 761 of the tube 753.

Referring now to FIGS. 71 and 72, the outer wall 761 of the tube 753 comprises many ventilation channels 763. To increase the clarity of the figures, not all of the ventilation channels are labeled.

The ventilation channels 763 are configured to enable airflow between an area 765 inside the tube 753 and the phase change system 734k (labeled in FIG. 69). The area 765 inside the tube 753 can be where the medicine 702 is stored inside the system 700k (shown in FIG. 69).

The outer wall 761 of the tube 753 can comprise a second ventilation channel 763 located on an opposite side of the tube 753 relative to a first ventilation channel 763. The tube 753 can include many ventilation channels 763 that are oriented radially outward (e.g., relative to a central axis 767 of the tube 753). The ventilation channels 763 can have diverse shapes (e.g., round, square, rectangle). As shown in FIG. 69, the ventilation channels 763 can be configured to facilitate heat transfer between the medicine 702 and the phase change system 734k.

Referring now to FIGS. 69 and 70, the bags 755a-e can be flexible such that they are configured to conform to fit in an area between the tube 753 and an interior wall 710k of the insulated container 706k. In some embodiments, the bags 755a-e are "highly flexible" such that when drained of PCM, a first end of each bag can be bent 180 degrees relative to an opposite end of the bag without causing any damage to the bag. Conformable bags 755a-e can be helpful during the assembly through the narrow opening 751.

In some embodiments, a first flexible bag comprises at least two fluidly isolated chambers (e.g., 755a, 755b, 755e) having a first phase change material. The second flexible bag can comprise at least two fluidly isolated chambers (e.g., 755c, 755d) having a second phase change material.

As shown in FIG. 69, the first flexible bag (e.g., 755a, 755b) can be wrapped at least partially around the tube 753. The second flexible bag (e.g., 755c, 755d) can be wrapped at least partially around the tube 753. A first PCM blanket 759a (shown in FIG. 70) is wrapped around a second PCM blanket 759b (shown in FIG. 70) in the configuration shown in FIG. 69. In several embodiments, the first flexible bag (e.g., 755a, 755b) is wrapped at least partially around the second flexible bag. In some embodiments, the second flexible bag (e.g., 755c, 755d) is wrapped at least partially around the first flexible bag (e.g., 755a, 755b).

The insulated container 706k is insulated by a vacuum chamber 708k. The vacuum flask can comprise an inner wall 710k and an outer wall 712k with a gas pressure between the inner wall and the outer wall that is less than atmospheric pressure (to create a "vacuum chamber"). In some embodiments, the pressure between the inner wall 710k and the outer wall 712k can be less than 60% of atmospheric pressure, less than 40% of atmospheric pressure, and/or less than 20% of atmospheric pressure. The atmospheric pressure can be measured at sea level.

The insulated container 706k can use other types of insulation methods in addition to or instead of using a vacuum chamber 708k. The other types of insulation described herein and/or incorporated by reference can be used to insulate the container 706k.

As shown in FIG. 69, the phase change system 734k is wrapped around the tube 753, the insulated container 706k comprises a first central axis 769, the tube comprises a second central axis 767 (shown in FIG. 72) that is within 15 degrees of being aligned with the first central axis 769, and the tube 753 extends from an upper half (i.e., a proximal half) of the insulated container 706k to a lower half (i.e., a distal half) of the insulated container 706k. (The upper half is located closer to the lid 704k than the lower half.)

As used herein, "extends" means to continue in a specified direction or over a specified distance, but unless stated otherwise, typically does not mean to become longer.

In some embodiments, the first central axis 769 is aligned with the second central axis 767 (shown in FIG. 72). In some embodiments, the tube extends along a portion of the first central axis 769 such that the tube is radially centered relative to the container 706k.

The tube 753 is held inside the insulated container 706k. At least one flex arm 771 is configured to hold the tube 753 inside the insulated container 706k. The flex arms 771 protrude farther radially outward (relative to a central axis 769) than a narrowest section 773 of an interior of the insulated container 706k such that the flex arms 771 are configured to flex radially inward (relative to a central axis 769) in response to inserting the tube 753 into the insulated container 706k and the flex arms 771 are configured to contact a narrowing section 775 of the interior to hold the tube 753 inside the insulated container 706k.

An arrow in FIG. 73 illustrates a radially inward direction in which the flex arm 771 bends in response to contacting the narrowest section 773 (in the neck of the container 706k) as the tube 753 is inserted through the opening 751 and into the final position of the tube 753 (as shown in FIG. 69). Flexing radially inward enables the arm 771 to move past the narrowest section 773.

The flex arm 771 comprises a cantilever beam 777. The cantilever beam 777 can be oriented within 20 degrees of parallel to a central axis 767 (and/or a central axis 769). These orientations are helpful to enable the cantilever beam 777 to flex in response to inserting the tube 753 into the container 706k.

Referring now to FIGS. 69, 70, and 73, the cantilever beam 777 (of the flex arm 771) is oriented within 80 degrees of a direction oriented (1) along a central axis 767 of the tube 753 and (2) towards the opening 751 such that pulling the tube 753 towards the opening 751 increases a resistance of the flex arm 771 to the pulling. This "engaging" structure can help prevent inadvertent removal of the tube 753 from the insulated container 706k. The tube 753 and the flex arms 771 can be molded plastic (e.g., as a single piece or as separate pieces that are coupled together).

The tube 753 comprises flex arms 771 having a cantilever beam 777 and a portion 779 to engage an interior of the insulated container 706k to hold the tube 753 inside the insulated container 706k (e.g., in the narrowing section 775 of the interior). The portion 779 is oriented towards a narrowing portion 775 of an interior of the insulated container 706k. For example, the interior of the container 706k can be the widest in a region that holds the phase change system 734k. The interior of the container 706k can be narrower in the opening 751 than in the region that holds the phase change system 734k. A narrowing portion 775 is typically necessary to transition from the wider portion to the narrow portion of the interior of the container 706k. Engaging this narrowing portion can be particularly helpful in preventing the tube 753 from falling out of the insulated container 706k.

In some embodiments, the tube 753 is coupled to a bracket 781 that holds the tube 753 inside the insulated container 706k. Bracket embodiments can have diverse shapes and sizes. In some embodiments, the bracket 781 is rigidly coupled to an interior of the insulated container 706k. In some embodiments, the bracket 781 has a hole in which a portion of the tube 753 is placed (e.g., to hold the tube in a center of the insulated container such that the hole of the bracket 781 is aligned with the central axis 769 of the container 706k).

In several embodiments, a maximum width of the opening 751 is measured from a central axis 769 of the insulated container 706k in a direction perpendicular to the central axis 769. The tube 753 can be coupled to a bracket 781 having an outermost edge located farther from the central axis 769 than the maximum width of the opening 751 such that the bracket 781 holds the tube 753 inside the insulated container 706k. In other words, the outermost edge of the bracket 781 can stick out so far that it cannot fit through the opening 751. (The bracket 781 can flex to enable inserting the bracket 781 into the insulated container 706k.)

In several embodiments, a spring 783 facilitates removing the medicine 702 from the insulated container 706k (e.g., by pushing the medicine 702 towards the opening 751 of the insulated container 706k to help a user grasp a proximal portion of the medicine 702).

The spring 783 is located in the insulated container 706k. The spring 783 is configured to push the medicine 702 towards the opening 751. A proximal platform 785 can be located inside the tube 753 such that the spring 783 pushes the proximal platform 785 towards the opening 751 to push the medicine 702 at least partially out of the opening 751 so a user can pull the medicine 702 out of the storage system 700k.

FIGS. 72 and 74 illustrates the spring system, which has a spring 783, a proximal platform 785, and a bracket 789. The spring 783 is configured to push the proximal platform 785 away from the bracket 789. The bracket 789 has radially outward protrusions 791 that interlock with notches 793 (shown in FIG. 70) in the tube 753.

The bracket 789 and the platform 785 comprise protrusions 797 and/or indentations 795 to receive an end of the spring 783 to secure the spring 783. The protrusions 797 and indentations 795 are cylindrical.

Referring now to FIGS. 71 and 74, the platform 785 comprises radially outward protrusions 787 that are located in guides (e.g., vertical slots) 801 of the tube 753. The protrusions 787 and guides 801 help prevent the platform 785 from rotating relative to the tube 753.

Referring now to FIGS. 75-78, in several embodiments, systems include a rotational release mechanism 803 to guard against overtightening, which could result in difficulty removing the lid 704k of the storage system 700k. The lid 704k (and its rotational release mechanism 803) can be used with any of the containers described herein and/or incorporated by reference.

The insulated container 706k and/or the lid 704k can comprise a rotational release mechanism 803 configured such that the lid 704k is rotatable relative to the insulated container 706k in a first rotational direction 813 that tightens the lid 704k to the insulated container 706k (via an applied torque) and in a second rotational direction 815 that loosens the lid 704k from the insulated container 706k (via an applied torque). The lid 704k can comprise a first portion 807 and a second portion 809. The first portion 807 can comprise threads 811 that couple the lid to the insulated container 706k.

The second portion 809 of the lid 704k is configured to rotate in the first rotational direction 813 relative to the first portion 807 of the lid 704k in response to a first applied torque that exceeds a release threshold (e.g., a torque). The second portion 809 of the lid 704k can be configured to resist rotation in the second rotational direction 815 relative to the first portion 807 in a presence of a second applied torque that is at least thirty percent larger than a magnitude of the release threshold.

In several embodiments, the rotational release mechanism 803 comprises an interface 816 between the first portion 807 and the second portion 809. The interface 816 can have teeth 817 slanted such that rotating the second portion 809 relative to the first portion 807 of the lid 704k in the first rotational direction 813 requires a lower torque than rotating the second portion 809 relative to the first portion 807 of the lid 704k in the second rotational direction 815.

The second portion 809 of the lid 704k can have protrusions 819 that protrude radially inward relative to a central axis 818 of the lid 704k. The interface 816 can be configured such that rotating the second portion 809 relative to the first portion 807 causes a protrusion 819 to collide with the tooth 817.

The tooth 817 has a peak 822. The peak of the tooth is the "highest" point of the tooth 817. When a tooth protrudes radially outward, the peak is the point of the tooth that is the farthest radially outward. When a tooth protrudes radially inward, the peak is the point of the tooth that is the farthest radially inward. When a tooth protrudes upward, the peak is the point of the tooth that is the farthest upward. When a tooth protrudes downward, the peak is the point of the tooth that is the farthest downward.

The tooth 817 comprises a first side 820 and a second side 821. The first side 820 is separated from the second side 821 by the peak 822. When the lid 704k is screwed into the container 706k, the protrusion 819 collides with the first side 820 of the tooth 817. When the lid 704k is unscrewed from the container 706k, the protrusion 819 collides with the second side 821 of the tooth 817. The tooth 817 is slanted such that the first side 820 is more gradual than the second side 821. In other words, the second side 821 is more abrupt than the first side 820. As a result, the torque required to rotate the second portion 809 (of the lid 704k) relative to the first portion 807 (of the lid 704k) is less when the lid 704k is unscrewed from the container 706k than when the lid 704k is screwed into the container 706k (as measured when the first portion 807 does not rotate).

Figure 75:
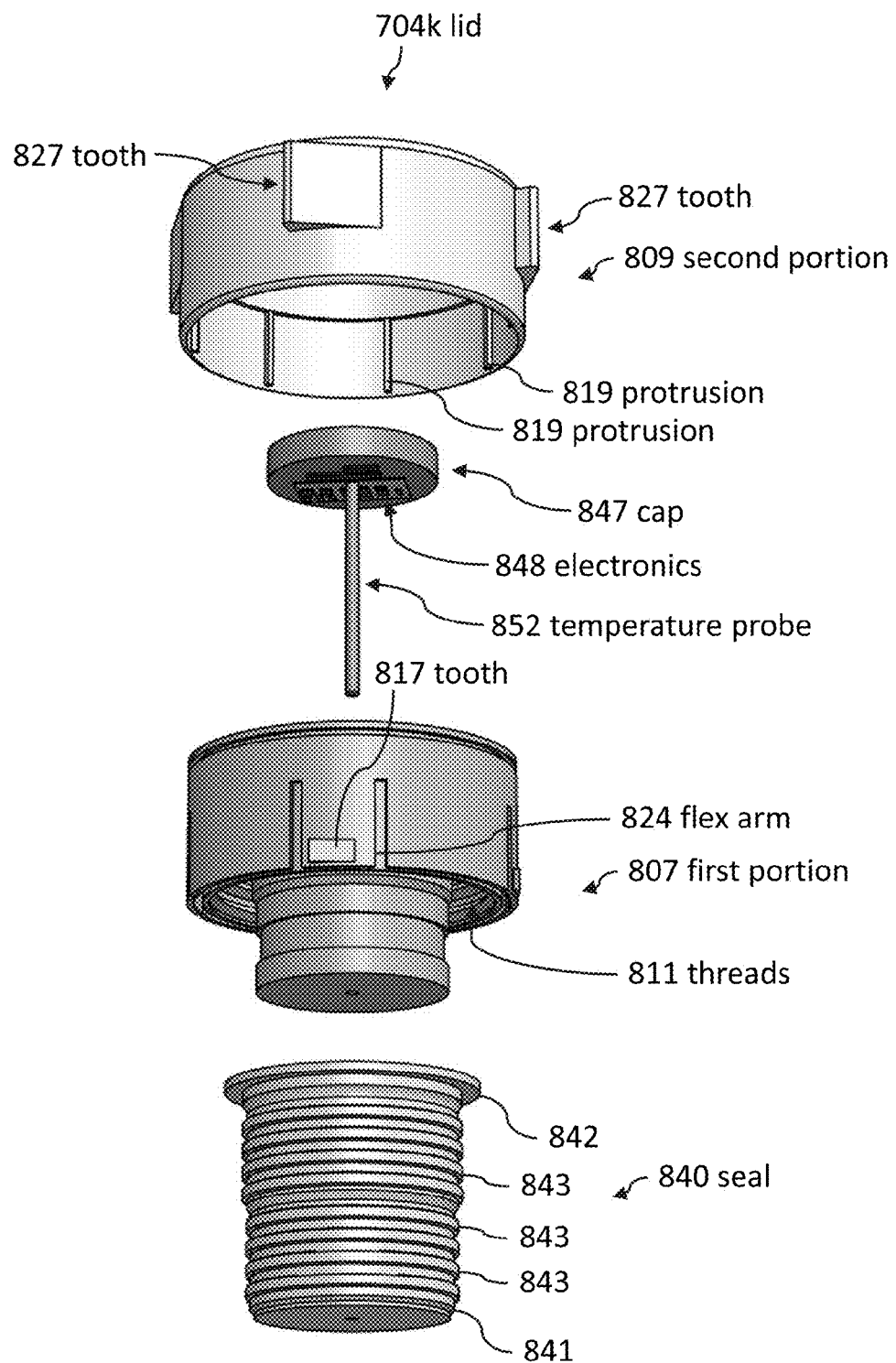
FIG. 75 illustrates a perspective, exploded view of a lid, according to some embodiments.

As shown in FIG. 75, the tooth 817 is located on a flex arm 824 configured to bend radially inward to enable the protrusion 819 to move past the tooth 817. As shown in FIG. 77, a gap 825 enables the tooth 817 to flex radially inward.

FIG. 78 illustrates teeth 827 that protrude radially outward and are slanted such that they provide greater grip when unscrewing the lid 704k than when screwing the lid 704k into the container 706k. The teeth 827 protrude radially outward from an outer perimeter of the lid 704k.

Each tooth 827 comprises a first side 828, a second side 829, and a peak 830. The first side 828 is separated from the second side 829 by the peak 830. The tooth 827 is slanted such that the first side 828 is more gradual than the second side 829. In other words, the second side 829 is more abrupt than the first side 828.

In some embodiments, on the first side 828, the tooth 827 is tangent to an outer perimeter of the lid 704k. In some embodiments, the first side 828 is defined by a point 857 where the tooth 827 joints the outer perimeter 859 of the lid 704k. (The outer perimeter 859 of the lid 704k can be cylindrical and/or have a circular cross section that is perpendicular to a central axis of the lid 704k.)

A first measurement line can measured between the point 857 and the peak 830 of the tooth 827. A second measurement line can be measured between a central axis of the lid 704k and the point 857. In several embodiments, a first angle between the first measurement line and the second measurement line is less than 135 degrees; less than 120 degrees; and/or greater than 89 degrees.

In some embodiments, the second side 829 is defined by a point 861 where the tooth 827 joints the outer perimeter 859 of the lid 704k. A third measurement line can measured between the point 861 and the peak 830 of the tooth 827. A fourth measurement line can be measured between a central axis of the lid 704k and the point 857. In several embodiments, a second angle between the third measurement line and the fourth measurement line is greater than 135 degrees; greater than 150 degrees; and/or equal to 180 degrees such that the third measurement line and the fourth measurement line are parallel to each other.

In several embodiments, the first measurement line is at least 30 percent longer and/or at least 50 percent longer than the third measurement line such that a first average slope of the first side 828 is less than a second average slope of the second side 829.

In several embodiments, a first coefficient of friction of the first side 828 is less than a second coefficient of friction of the second side 829 such that the second side 829 is configured to provide stronger gripping traction than the first side 828.

FIG. 79 illustrates a perspective view of a phase change system 734h that has bags 755f-i at least partially filled with PCM. Flex arms 771 protrude radially outward to help secure the tube 753 in the container (not shown).

Referring now to FIGS. 69, 70, and 79, a storage system 700k can comprise an insulated container 706k having an opening 751; a lid 704k configured to cover the opening 751; a phase change system 734k located inside the insulated container 706k; and a tube 753 located inside the insulated container 706k such that the tube 753 is in fluid communication with the opening 751 (to enable inserting a medicine 702 through the opening 751 and into the tube 753). The phase change system 734h can comprise a first bag 755a having a first phase change material. The first phase change material can have a first melting temperature greater than 40 degrees Fahrenheit and less than 74 degrees Fahrenheit. The insulated container 706k can be a vacuum flask such that the insulated container 706k is insulated by a vacuum chamber 708k. The first bag 755a can be located inside the insulated container 706k and outside the tube 753 such that the first bag 755a is located between an inner wall 710k of the insulated container 706k and an outer wall 761 of the tube. The tube 753 can extend from an upper half of the insulated container 706k to a lower half of the insulated container 706k such that the storage system 700k is configured to enable a user to remove the lid 704k, insert the medicine 702 through the opening 751 and into the tube 753, replace the lid 704k, and protect the medicine 702 from temperatures below 40 degrees Fahrenheit.

In several embodiments, a storage system 700k comprises an insulated container 706k having an opening 751; a lid 704k configured to cover the opening 751; a phase change system 734k located inside the insulated container 706k; and a tube 753 located inside the insulated container 706k such that the tube 753 is in fluid communication with the opening 751 (to enable inserting a medicine 702 through the opening 751 and into the tube 753). The phase change system 734k can comprise a first bag 755a having a first phase change material. The first phase change material can have a first melting temperature greater than 74 degrees Fahrenheit and less than 100 degrees Fahrenheit. The insulated container 706k can be insulated by a vacuum chamber 708k. The first bag 755a can be located inside the insulated container 706k and outside the tube 753 such that the first bag 755a is located between an inner wall 710k of the vacuum chamber 708k and an outer wall 761 of the tube 753. The tube 753 can extend from an upper half of the insulated container 706k to a lower half of the insulated container 706k such that the storage system 700k is configured to enable a user to remove the lid 704*k*, insert the medicine 702 through the opening 751 and into the tube 753, replace the lid 704*k*, and protect the medicine 702 from temperatures above 100 degrees Fahrenheit.

In some embodiments, an interior of the insulated container 706*k* comprises a first cylindrical section 833 and a second cylindrical section 835 that is closer to the opening 751 than the first cylindrical section 833. The second cylindrical section 835 can have a second diameter that is smaller than a first diameter of the first cylindrical section 833. The first cylindrical section 833 can have a first length measured along a central axis 769 of the insulated container 706*k*. The second cylindrical section 835 can have a second length measured along the central axis 769 of the insulated container 706*k*. The first length can be at least twice as long as the second length.

Referring now to FIGS. 69-72, in several embodiments, the tube 753 comprises a third cylindrical section 837 having a third diameter and a third length. The third length is measured along a central axis 767 of the tube 753. The tube 753 can comprise a fourth cylindrical section 839 having a fourth diameter and a fourth length. The fourth length is measured along the central axis 767 of the tube 753. The fourth cylindrical section 839 can couple the third cylindrical section 837 to the opening 751 of the insulated container 706*k*. The fourth diameter can be larger than the third diameter. The third length can be at least twice as long as the fourth length.

In some embodiments, threads 811 of the storage system 700*k* couple the insulated container 706*k* to the lid 704*k*. At least one of the second cylindrical section 835 and a portion of the insulated container 706*k* located radially outward from the second cylindrical section 835 can comprise threads 811 configured to couple the lid 704*k* to the insulated container 706*k*. As used herein, a section can be cylindrical even if it has threads.

FIG. 75 illustrates a perspective, exploded view of the lid 704*k*. In several embodiments, seals are configured to limit or eliminate fluid communication between an environment outside the storage system 700*k* and an interior of the storage system 700*k* where the medicine 702 is stored.

The lid 704*k* can comprise a seal 840, which can include a distal compression seal 841, a proximal compression seal 842, and at least one radial seal 843 located between the distal compression seal 841 and the proximal compression seal 843. Seals can be wiper seals, o-rings, or any other suitable type of seal. Seals can be made from silicone or any other suitable material.

The lid 704*k* can include a cap 847. The cap 847 (or any other portion of the lid 704*k* and/or the storage system 700*k*) can include electronics 848, a battery 849, and a display 850. The display 850 can show temperature information and other information related to medicine storage. The electronics 848 can include a printed circuit board 851, which can include an accelerometer configured to detect if the system is moving. A temperature probe 852 can be used to measure a temperature inside the medicine storage area of the system 700*k*. The many features described in the context of FIG. 5 of U.S. Nonprovisional patent application Ser. No. 14/849,884, including but not limited to the electronic features and the computer 76, can be combined with any of the embodiments described in the context of FIGS. 69-79. The lid 18 shown in FIG. 5 of U.S. Nonprovisional patent application Ser. No. 14/849,884 can be used with any portion of the storage system 700*k*.

In some embodiments, all features, assemblies, components, and innovations related to the lid 18 shown in FIG. 5 of U.S. Nonprovisional patent application Ser. No. 14/849,884 are combined with the features, assemblies, components, and innovations described herein in the context of lid 704*k* (shown in FIGS. 66-70 and 75-78).

An area 853 under the cap 847, around the temperature probe 852, and/or within the first portion 807 of the lid 704*k* can be filled and/or insulated with foam or any other suitable insulation. In some embodiments, this area 853 comprises a second vacuum chamber that is located inside the lid 704*k*.

In any of the embodiments described herein and/or incorporated by reference, a storage system can comprise a thermometer configured to measure a temperature of an interior area of the insulated container; a wireless communication system communicatively coupled with a remote computing device; and a first wireless communication sent from the medicine storage system to the remote computing device in response to at least one of (1) the temperature falling below a predetermined minimum temperature threshold, (2) the temperature rising above a predetermined maximum temperature threshold, (3) falling below a first predetermined amount of time until the temperature is predicted to fall below the predetermined minimum temperature threshold, and (4) falling below a second predetermined amount of time until the temperature is predicted to rise above the predetermined maximum temperature threshold. Additional details are described in the context of FIG. 5 of U.S. Nonprovisional patent application Ser. No. 14/849,884 and in other portions of U.S. Nonprovisional patent application Ser. No. 14/849,884. The electronics 847 shown in FIG. 78 include a wireless communication system. FIGS. 69 and 75 illustrate a lid having a thermometer (e.g., a temperature probe 852).

In any of the embodiments described herein and/or incorporated by reference, a storage system can comprise a thermometer configured to measure a temperature of an interior area of the insulated container; and a computing system configured to emit at least one of a visual indicator and an audio indicator in response to at least one of (1) the temperature falling below a predetermined minimum temperature threshold, (2) the temperature rising above a predetermined maximum temperature threshold, (3) falling below a first predetermined amount of time until the temperature is predicted to fall below the predetermined minimum temperature threshold, and (4) falling below a second predetermined amount of time until the temperature is predicted to rise above the predetermined maximum temperature threshold. Additional details are described in the context of FIG. 5 of U.S. Nonprovisional patent application Ser. No. 14/849,884 and in other portions of U.S. Nonprovisional patent application Ser. No. 14/849,884. The electronics 847 shown in FIG. 78 include a computing system configured to emit visual indicators and audio indicators. FIGS. 69 and 75 illustrate a lid having a thermometer (e.g., a temperature probe 852).

Figure 66:
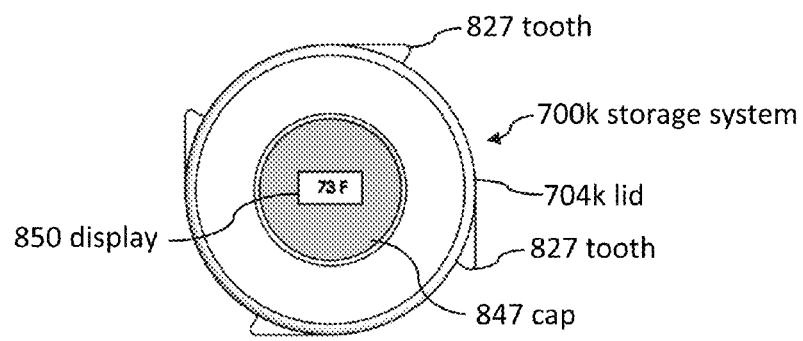
FIG. 66 illustrates a top view of a medicine storage system, according to some embodiments.

In any of the embodiments described herein and/or incorporated by reference, a storage system can have a lid configured to cover an opening of an insulated container. The lid can comprise a thermometer system configured to measure a temperature of an interior area of the insulated container. The lid can comprise a display configured to show the temperature. The lid can comprise an inward portion and an outward portion. The inward portion can be located closer to the medicine storage area than the outward portion of the lid. A portion of the thermometer system can be coupled to the inward portion of the lid such that the portion of the thermometer system is configured to sense the temperature of the interior area. The display can be located on an outward facing side of the lid such that the display is configured to show the temperature even when the lid is screwed onto the insulated container. The thermometer system and the display can be electrically coupled to a computing system configured to enable the storage system to measure the temperature and show the temperature on the display. Additional details are described in the context of FIG. 5 of U.S. Nonprovisional patent application Ser. No. 14/849,884 and in other portions of U.S. Nonprovisional patent application Ser. No. 14/849,884. The lid 704k illustrated in FIG. 76 includes a temperature probe 852 that protrudes distally from a distal end of the lid 704k. FIG. 66 illustrates that the lid 704k includes a display 850 (which shows a temperature e.g., "73 F," of an interior area of the insulated container 706k). The electronics 847 shown in FIG. 78 include a computing system that electrically couples the thermometer system 852 and the display 850 to enable the storage system 700k to measure the temperature and show the temperature on the display 850.

Any of the embodiments described herein and/or incorporated by reference can be used to protect a medicine from a first external temperature less than a minimum recommended storage temperature and from a second external temperature greater than a maximum recommended storage temperature by utilizing phase changes to regulate a temperature of the medicine. The manufacturer of the medicine can specify the minimum and maximum recommended storage temperatures. (The external temperature is a temperature of the environment outside of the storage system.)

The minimum and maximum recommended storage temperatures can be for a long duration of time and/or for a short duration of time. For example, the manufacturer might recommend a first minimum recommended storage temperature for long-term storage and a second minimum recommended storage temperature for short-term storage. In some cases, the first minimum recommended storage temperature is higher than the second minimum recommended storage temperature (due to the vulnerability of certain medicines to low temperatures over extended periods of time).

The manufacturer might recommend a first maximum recommended storage temperature for long-term storage and a second maximum recommended storage temperature for short-term storage. In some cases, the first maximum recommended storage temperature is lower than the second maximum recommended storage temperature (due to the vulnerability of certain medicines to high temperatures over extended periods of time).

The ability of the medicine storage system to protect against both hot and cold temperatures is highly advantageous for many reasons. For example, outdoor temperatures can often swing between temperatures that are too high for a medicine during a sunny day and then reach a temperature that is too low for the medicine during the following night.

Having both hot and cold temperature protection is also helpful because it makes the system less dependent on the user planning ahead for either hot or cold temperatures. Instead, one storage system can be used regardless of the season, time of day, or unexpected temperature swings. The result is a storage system that is more versatile, less prone to user error, and automatically adaptable to unexpected weather changes.

Figure 80:
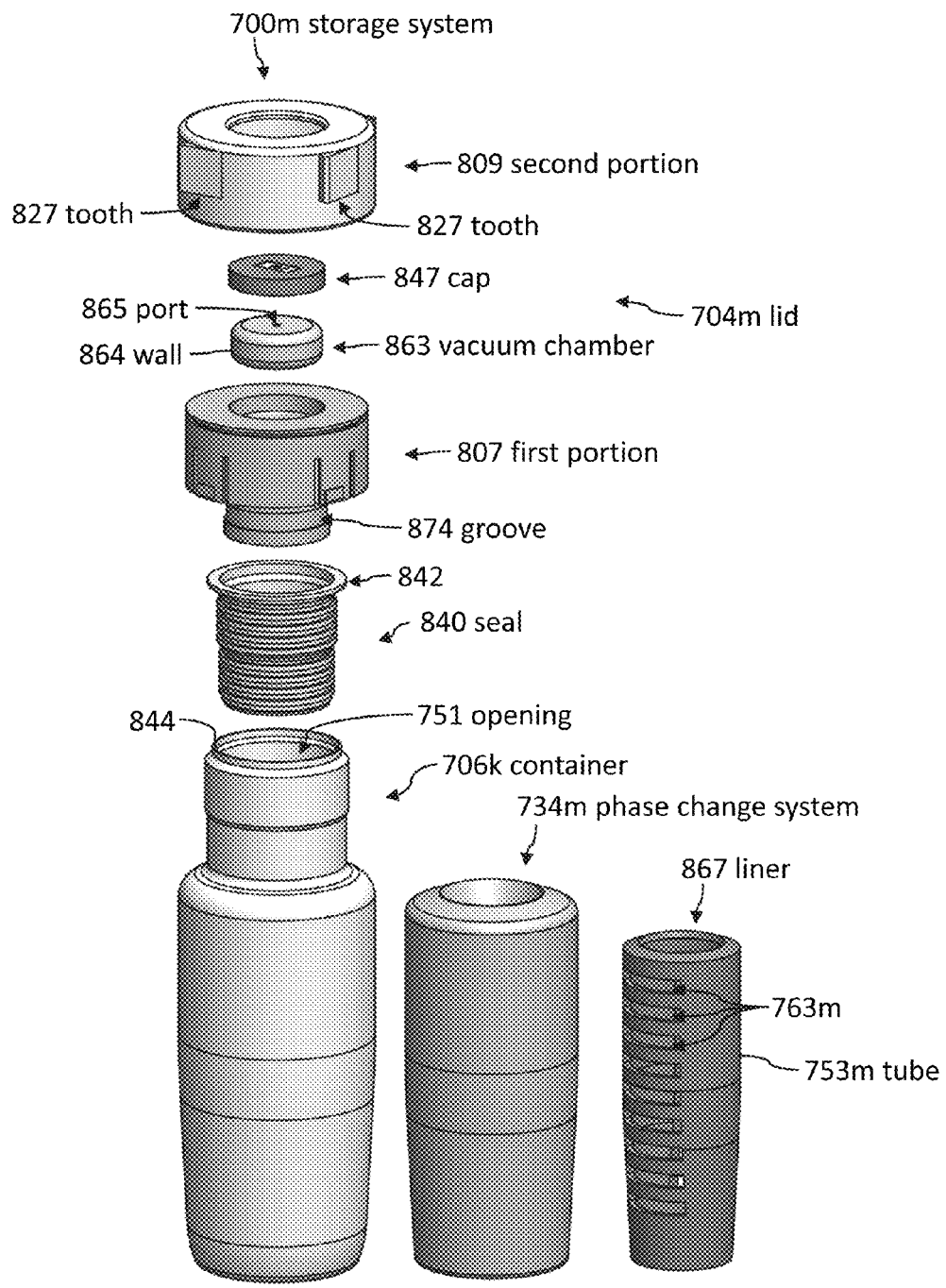
FIG. 80 illustrates a perspective view of a disassembled medicine storage system, according to some embodiments.
Figure 85:
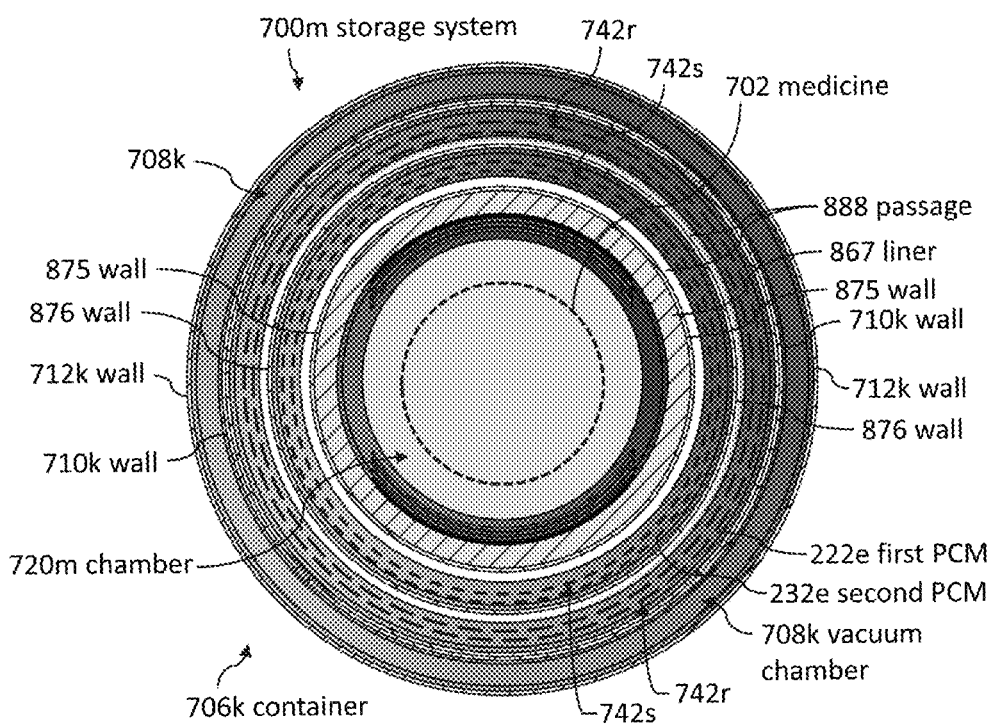
FIG. 85 illustrates a cross-sectional view taken along line 85-85 from FIG. 84, according to some embodiments.

FIG. 80 illustrates a perspective view of a disassembled medicine storage system 700m, which can include any of the features, assemblies, components, and innovations described in the context of other embodiments described herein and/or incorporated by reference. Cross-sectional views of the storage system 700m in an assembled state are shown in FIGS. 83 and 85.

The many features described in the context of FIG. 5 of U.S. Nonprovisional patent application Ser. No. 14/849,884, including but not limited to the electronic features and the computer 76, can be combined with any of the embodiments described in the context of FIGS. 80-85. The lid 18 shown in FIG. 5 of U.S. Nonprovisional patent application Ser. No. 14/849,884 can be used with any portion of the storage system 700m.

In some embodiments, all features, assemblies, components, and innovations related to the lid 18 shown in FIG. 5 of U.S. Nonprovisional patent application Ser. No. 14/849,884 are combined with the features, assemblies, components, and innovations described herein in the context of lid 704m (shown in FIGS. 80-85).

Referring now to FIG. 80, the lid 704m can include a seal 840 coupled to the first portion 807, the second portion 809 rotatably coupled to the first portion 807, the vacuum chamber 863 located within the first portion 807 and/or within the second portion 809 such that the vacuum chamber 863 is at least partially surrounded by insulation (e.g., foam insulation), and a cap 847, which can include electronics configured to communicate with a remote computing device (e.g., a smartphone) and configured to provide temperature alerts.

The phase change system 734m can fit inside the container 706k. The phase change system 734m can be manufactured along with the container 706k using processes used for making vacuum flasks except that ports typically used to extract air to form vacuum chambers can be used to fill chambers with PCMs. The ports can be welded shut to prevent the PCMs from leaking out of the phase change system 734m. The phase change system 734m can be made from stainless steel to help avoid corrosion problems.

In some embodiments, the phase change system 734m is molded from plastic and filled with PCMs. The phase change system 734m can be inserted into the container 706k (e.g., before a bottom portion of the container 706k is welded onto the rest of the container 706k).

Some embodiments include a liner 867, which can include ventilation channels 763m to help promote heat transfer within the system 700m. The liner 867 can comprise a tube 753m. The liner 867 can be molded from a soft material configured to help pad an interior portion of the phase change system 734m (e.g., especially if the phase change system 734m is made from metal) so the medicine container 702 is not damaged by hitting hard walls. The liner 867 can conform to interior walls of the phase change system 734m (e.g., as shown in FIG. 83).

Figure 84:
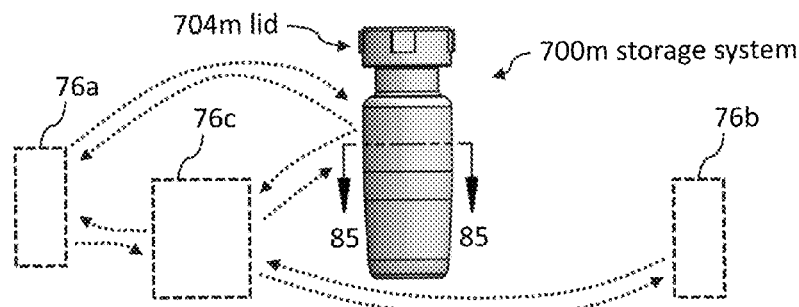
FIG. 84 illustrates a side view of a medicine storage system, according to some embodiments.

FIG. 81 illustrates a side view of a medicine storage system 700m. FIG. 82 illustrates an enlarged view of the area indicated by circle AA in FIG. 83. FIG. 83 illustrates a cross-sectional view taken along line 83-83 from FIG. 81. FIG. 84 illustrates a side view of a medicine storage system 700m.

FIG. 85 illustrates a cross-sectional view taken along line 85-85 from FIG. 84. Embodiments can include an air passage 888 between PCM chambers (e.g., within the wall 876) and/or between the medicine chamber 720m and at least one PCM chamber. The air passage 888 can be fluidly coupled with the medicine chamber 720m to provide additional PCM chamber surface area to increase heat transfer between the PCM and the medicine chamber 720m.

Referring now to FIGS. 80 and 83, the container 706k can include a vacuum chamber 708k, which provides highly effective insulation. (Some embodiments use foam insulation.) The vacuum chamber 708k is so effective at limiting heat transfer into and out of the storage system 700m that the thermally weakest portion of the system 700m is typically the lid.

Insulation areas 868 and the seal 840 help to reduce heat transfer through the lid 704m, but lids can still permit substantial heat transfer, which is especially problematic due to the sometimes slow heat transfer rates of PCMs. The vacuum chamber 863 can greatly improve the insulation properties of the lid 704m, and thereby can enable a system that reduces heat transfer rates enough such that the PCMs can release or absorb heat faster enough to maintain a suitable temperature to protect the medicine 702.

Referring now to FIGS. 80-85, medicine storage systems 700m can include an outer circular wall 712k; an inner circular wall 710k coupled to the outer circular wall 712k; and a first vacuum chamber system 708k located between the inner circular wall 710k and the outer circular wall 712k.

Figure 67:
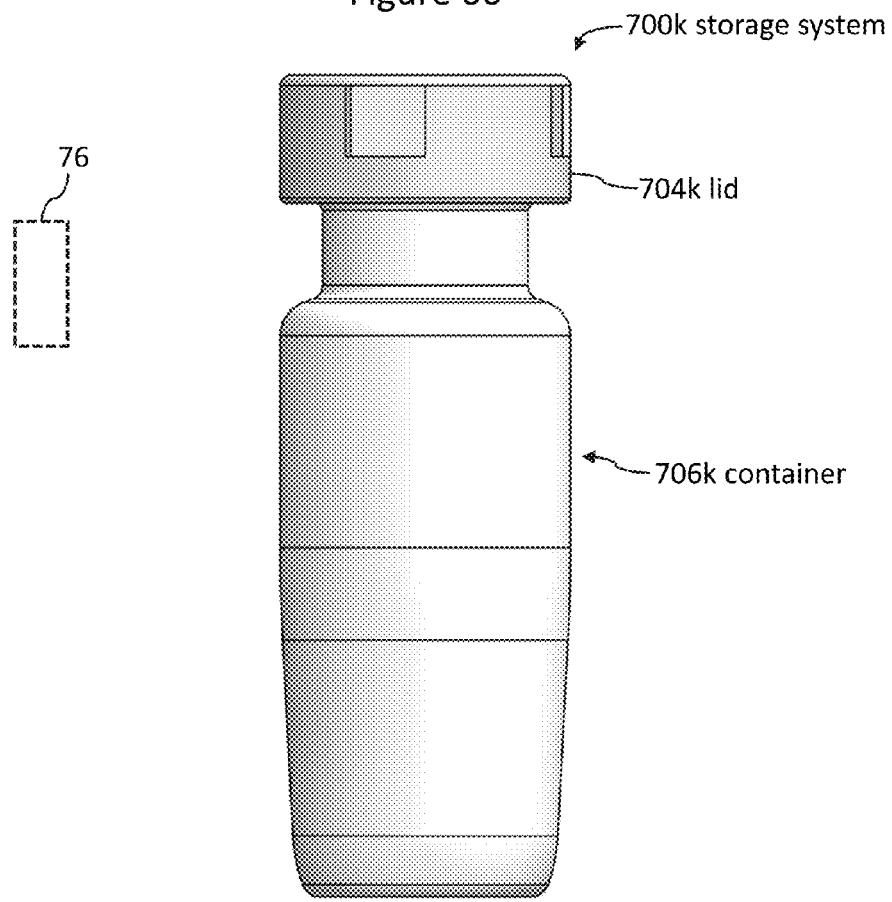

Some embodiments include outer and inner walls that are cylindrical with varying diameters (e.g., as shown in FIGS. 67, 69, and 83). In other words, taking cross sections perpendicular to a central axis of the walls would show circular shapes and/or elliptical shapes. As used herein, "circular wall" includes circular shapes and elliptical shapes. FIG. 85 shows circular walls (e.g., 710k and 712k). Circular walls are often effective at resisting forces created due to vacuum chambers (e.g., external pressures on the wall are much higher than internal forces on the wall due to the vacuum chamber, which is typically not a "perfect vacuum").

The first vacuum chamber system 708k can comprise at least one vacuum chamber. In some embodiments, dividing walls couple the outer wall 712k to the inner wall 710k and separate a first vacuum chamber from a second vacuum chamber.

In some embodiments, medicine storage systems 700m include a first chamber 720m at least partially surrounded by the first vacuum chamber system 708k; a removable medicine container 702 located inside the first chamber 720m; and a proximal portion of the medicine storage system 700m. The proximal portion can comprise an opening 751 to the first chamber 720m. The opening 751 can be covered by a removable lid 704m. The medicine storage system 700m can be configured such that removing the lid 704m enables a user to remove the medicine container 702 from the first chamber 720m.

In several embodiments, the medicine storage system 700m comprises a phase change system 734m that includes a second chamber 742r having a first phase change material 222e and a third chamber 742s having a second phase change material 232e. (In some embodiments, the second chamber 742r contains the second phase change material 232e and the third chamber 742s contains the first phase change material 222e.)

FIG. 24 of U.S. Nonprovisional patent application Ser. No. 14/616,652 illustrates a first PCM 222e in a second chamber 220e and a second PCM 232e in a third chamber 230e. U.S. Nonprovisional patent application Ser. No. 14/616,652 is incorporated by reference herein.

Referring now to FIGS. 80-85, the phase change system 734m can be at least partially surrounded by the first vacuum chamber system 708k such that the first vacuum chamber system 708k is configured to insulated the phase change system 734m from an environment that is external to the medicine storage system 700m. The first phase change material 222e can have a first melting temperature greater than 40 degrees Fahrenheit and less than 74 degrees Fahrenheit, and the second phase change material 232e can have a second melting temperature greater than 74 degrees Fahrenheit and less than 100 degrees Fahrenheit.

In some embodiments, a medicine storage system 700m comprises a liner 867 located in the first chamber 720m. The liner 867 can surround at least a majority of the removable medicine container 702. The liner 867 can be made from a first material. The first chamber 720m can be made from a second material that is at least two times harder than the first material as measured on the Brinell scale. The liner 867 can be molded from plastic, rubber, or any suitable material.

In several embodiments, a medicine storage system 700m comprises a first seal 841 located between the lid 704m and the opening 751 to the first chamber 720m (e.g., such that the first seal 841 is configured to block fluid from entering the first chamber 720m to keep the medicine container 702 dry). The first seal 841 can be configured to reduce heat transfer from an internal portion of the medicine storage system 700m to an area outside the medicine storage system 700m.

In some embodiments, the lid 704m is coupled to the proximal portion of the medicine storage system 700m by screw threads 811. The first seal 841 can be compressed by inserting a portion of the lid 704m into the opening 751 such that the first seal 841 is compressed between the portion of the lid 704m and a radially inward protrusion 871 of the opening 751 (e.g., as shown in FIG. 82).

In several embodiments, the medicine storage system 700m comprises a second seal 843 located between the lid 704m and the opening 751. The second seal 843 can be a radial seal that is radially compressed between the opening 751 and the lid 704m. A medicine storage system 700m can further comprise an air gap 873 (shown in FIG. 82) between the first seal 841 and the second seal 843 such that (1) the radial seal is configured to fluidly isolate the air gap 873 from a proximal portion of the opening 751 and (2) the first seal 841 is configured to fluidly isolate the air gap 873 from at least one of the first chamber 720m and a distal portion of the opening 751. The second seal 843 can be located proximally relative to the first seal 841. The first seal 841 and the second seal 843 can be located distally relative to the screw threads 811.

In some embodiments, the lid 704m comprises a groove 874 that faces radially outward. At least one of the first seal 841 and the second seal 843 can comprise a portion located in the groove 874. The groove 874 can be configured to help retain at least one seal (e.g., 840).

In several embodiments, a third seal 842 is located between a proximal end 844 of the opening 751 and a distally facing surface 845 of the lid 704m. The third seal 842 can be compressed between the proximal end 844 and the distally facing surface 845. The third seal 842 can be located proximally relative to the first seal 841 and the second seal 843. The first seal 841, the second seal 843, and the third seal 842 can be molded from rubber materials.

In some embodiments, the lid 704m comprises a second vacuum chamber 863. The second vacuum chamber 863 can be fluidly isolated from the first vacuum chamber system 708k such that screwing the lid 704m onto the proximal portion of the medicine storage system 700m rotates the second vacuum chamber 863 relative to the first vacuum chamber system 708k. The lid 704m can comprise a metal wall 864 having a port 865 that is welded closed. The port 865 can be used to remove a gas from the second vacuum chamber 863. Then, the port 865 can be welded closed. The second vacuum chamber 863 can be located within the metal wall 864. The lid 704m can further comprise insulation 868 that surrounds at least a majority of the second vacuum chamber 863. The second vacuum chamber 863 can be spherical, cylindrical, or any suitable shape.

In several embodiments, the second chamber 742*r* and the third chamber 742*s* are located radially outward from the first chamber 720*m* relative to a first central axis 769 of the first chamber 720*m*. The third chamber 742*s* can be located radially outward from the second chamber 742*r* (e.g., relative to the first central axis 769). The second chamber 742*r* can be located radially outward from the third chamber 742*s* (e.g., relative to the first central axis 769).

In some embodiments, the medicine storage system 700*m* comprising a recommended storage temperature. For example, a manufacturer of the medicine storage system 700*m* can recommend a temperature range at which to store the medicine storage system 700*m*. In some cases, this recommended storage temperature can be "room temperature" and/or a temperature range within plus or minus 20 degrees of 74 degrees Fahrenheit. The manufacturer can include this recommended storage temperature in a location in which customers will see the recommended storage temperature. The recommended storage temperature can be located on the medicine storage system 700*m* (e.g., printed on the storage system 700*m*). The recommended storage temperature can be located on packaging of the medicine storage system 700*m* (e.g., a box in which a storage system 700*m* is shipped and/or placed on a retail shelf). The recommended storage temperature can be located on instructions included with the medicine storage system 700*m* (e.g., an instruction sheet or instruction booklet that explains how to use the storage system 700*m*). The recommended storage temperature can be located on a website and/or in an instructional video.

In several embodiments, the first chamber 720*m*, the second chamber 742*r*, and the third chamber 742*s* (of the medicine storage system 700*m*) are concentric. The removable medicine container 702 can be an injection device having epinephrine (e.g., an EpiPen). The recommended storage temperature can be greater than the first melting temperature and less than the second melting temperature such that the medicine storage system 700*m* is configured such that when the medicine storage system 700*m* is stored for one week (or four weeks) in an environment having the recommended storage temperature, the first phase change material 222*e* is liquid and the second phase change material 232*e* is solid.

In some embodiments, the first chamber 720*m* extends from the proximal portion towards a distal portion of the medicine storage system 700*m* such that the first chamber 720*m* is at least as long as a majority of a length between a proximal end of the medicine storage system 700*m* and a distal end of the medicine storage system 700*m*. As used herein, "extends" means to continue in a specified direction or over a specified distance, but unless stated otherwise, typically does not mean to become longer.

In several embodiments, the first chamber 720*m* comprises a first central axis, the second chamber 742*r* comprises a second central axis, the third chamber 742*s* comprises a third central axis, and the second and third central axes are within 15 degrees of being parallel to the first central axis of the first chamber 720*m*. As illustrated in FIG. 83, the first, second, and third central axes are shown by axis 769.

As shown in FIG. 83, the vacuum chamber 708*k* has a smaller outer diameter in the proximal portion of the medicine storage system 700*m* than in the distal portion of the medicine storage system 700*m*. The vacuum chamber 708*k* extends farther proximally than the second chamber 742*r* and the third chamber 742*s* such that at least a portion of the opening 751 is surrounded by the vacuum chamber 708*k* but is not surrounded by the second chamber 742*r* and the third chamber 742*s*. As used herein, "extend" means to continue in a specified direction or over a specified distance, but unless stated otherwise, typically does not mean to become longer.

As shown in FIG. 83, a first portion of the lid 704*m* is located radially inward relative to a portion of the vacuum chamber 708*k*, and a second portion of the lid 704*m* is located radially outward relative to the portion of the vacuum chamber 708*k*.

As shown in FIG. 83, a proximal portion of the second chamber 742*r* tapers radially inward and a proximal portion of the third chamber 742*s* tapers inward to enable the vacuum chamber 708*k* to have the smaller outer diameter in the proximal portion of the medicine storage system 700*m* than in the distal portion of the medicine storage system 700*m*.

In several embodiments, the medicine storage system 700*m* comprises a radially inward protrusion 871 located between the opening 751 and the first chamber 720*m*. The lid 704*m* can comprise a seal 841 compressed between a portion of the lid 704*m* and the radially inward protrusion 871 (to block fluid from entering the first chamber 720*m* to keep the medicine container 702 dry).

In some embodiments, at least a majority of the opening 751 and at least a majority of the first chamber 720*m* are isodiametric.

In several embodiments, at least a majority of the opening 751 has diameters that are 10 percent to 65 percent larger than diameters of at least a majority of the first chamber 720*m*. This can be calculated using standard mathematical techniques.

In some embodiments, the first chamber 720*m* comprises a first central axis, the second chamber 742*r* comprises a second central axis, the third chamber 742*s* comprises a third central axis, and the second and third central axes are within 15 degrees of being parallel to the first central axis.

Referring now primarily to FIG. 85 (but also to FIG. 24 of U.S. Nonprovisional patent application Ser. No. 14/616, 652), at least a majority of the first chamber 720*m* is located within a first wall 875 and a second wall 876 that are located within the inner circular wall 710*k*. The first wall 875 can separate the first chamber 720*m* from a first portion of the phase change system 734*m*. The second wall 876 can separate the first chamber 720*m* from a second portion of the phase change system 734*m*. A PCM chamber can be located between the first wall 875 and the second wall 876. The first phase change material 222*e* can surround the majority of the first chamber 720*m*. The second phase change material 232*e* can surround the majority of the first chamber 720*m*.

In some embodiments, the second chamber 742*r* surrounds the majority of the first chamber 720*m* such that the first phase change material 222*e* can move 360 degrees around a first perimeter of the first chamber 720*m* when the first phase change material 222*e* is above the first melting temperature. The third chamber 742*s* can surround the majority of the first chamber 720*m* such that the second phase change material 232*e* can move 360 degrees around a second perimeter of the first chamber 720*m* when the second phase change material 232*e* is above the second melting temperature.

In several embodiments, the storage system 700*m* comprises a first wall 875 and a second wall 876 that are located within the inner circular wall 710*k*. The first wall 875 is located between the first chamber 720m (e.g., on the radially inward side of the first wall 875) and the first and second phase change materials 222e, 232e (e.g., on the radially outward side of the first wall 875). The first wall 875 surrounds at least a first portion of the first chamber 720m. The second wall 876 is located between the first phase change material 222e and the second phase change material 232e. The second wall 876 surrounds at least a second portion of the first chamber 720m. The second chamber 742r surrounds the first portion of the first chamber 720m such that the first phase change material 222e can move 360 degrees around a first perimeter of the first chamber 720m when the first phase change material 222e is above the first melting temperature, and the third chamber 742s surrounds the second portion of the first chamber 720m such that the second phase change material 232e can move 360 degrees around a second perimeter of the first chamber 720m when the second phase change material 232e is above the second melting temperature.

Referring now to FIG. 83, a fourth chamber 877 can be added to the phase change system 734m of the storage system 700m. The fourth chamber 877 can be at least partially filled with a third phase change material that has a third melting temperature. The third melting temperature can be at least one of (i) greater than 40 degrees Fahrenheit and less than the first melting temperature, and (ii) greater than the second melting temperature and less than 100 degrees Fahrenheit.

The third phase change material can be configured to provide backup protection against at least one of a first environment colder than 40 degrees Fahrenheit and a second environment hotter than 100 degrees Fahrenheit. For example, if the storage system 700m is in an environment that is colder than the melting temperature of the first phase change material, given enough time, the first phase change material will freeze. Once the first phase change material freezes (without backup protection), the storage system 700m would not have further phase changes to protect the medicine 702 from low-temperature induced damage. As a result, the medicine 702 could be damaged. In contrast, the addition of the third phase change material results in an additional phase change that provides backup protection (e.g., once all of the first phase change material is frozen).

Similarly, the system can include a fourth phase change material that has a melting temperature higher than the melting temperature of the second phase change material and lower than 100 degrees Fahrenheit. This fourth phase change material can provide backup protection in environments that are hotter than the melting temperature of the second phase change material.

Several embodiments of a storage system for injectable substances include a thermally insulating container. A substance with a high heat capacity can be located inside the insulating container. The substance can have a specific heat capacity of at least 2 Joules/gram*Kelvin and/or a volumetric heat capacity of at least 2 Joules/cm^3*Kelvin. A chamber configured to hold an injectable substance can also be located inside the insulating container. In some embodiments, the substance with a high heat capacity at least partially surrounds at least a portion of the chamber configured to hold the medicine (e.g., an injectable substance).

Storage systems can include a chamber configured to hold a medicine. This chamber can be configured to hold an injectable substance, which may be packaged in a separate storage container such as a plastic vial, a glass jar, and/or an injection device such as a syringe. Example injectable substances can be contained in products such as EpiPens, Twinjects, Adrenaclicks, Anapens, Jexts, Allerjects, Auvi-Qs, and ComboPens. Some injectable substance chambers 44 are configured to hold multiple containers of injectable substances. Some injectable substance chambers 44 are configured to hold an inhaler and/or another drug container.

As used herein, the term injectable substance can include a container that holds a liquid that users inject into their bodies. Some embodiments are similar to other embodiments described herein except the injectable substance is replaced with a container of an injectable liquid. The container can be plastic, glass, and/or a syringe.

The injectable substance (e.g., a medicine 702) can include epinephrine, adrenaline, insulin, hormones, and/or neurotransmitters. The injectable substance can include liquids or gases used to treat acute allergic reactions, to avoid anaphylactic shock, and/or to treat anaphylactic shock. The injectable substance can include liquids or gases used to treat diabetes. In some embodiments, the medicine 702 is an epinephrine auto-injector such as the EpiPen or EpiPen Jr. made by Mylan Specialty L.P. In some embodiments, the injectable substance is replaced by another pharmaceutical product or by another product that benefits from temperature stability.

The many features described in the context of FIG. 5 of U.S. Nonprovisional patent application Ser. No. 14/849,884, including but not limited to the electronic features and the computer 76, can be combined with any of the embodiments described herein or incorporated by reference herein. To reduce redundancy and to increase the clarity of other features in other figures, the features described in the context of FIG. 5 of U.S. Nonprovisional patent application Ser. No. 14/849,884 are not repeated for each figure herein. The lid 18 shown in FIG. 5 of U.S. Nonprovisional patent application Ser. No. 14/849,884 can be used with any of the storage systems described herein to combine many electrical elements with many types of storage systems.

Each embodiment described herein or incorporated by reference can include a thermometer (e.g., as described in U.S. Nonprovisional patent application Ser. No. 14/849,884), which can include a temperature probe 64a. As described in U.S. Nonprovisional patent application Ser. No. 14/849,884, at least a portion of the temperature probe 64a can be located inside the injectable substance chamber 44 (e.g., a first chamber) such that the temperature probe 64a is configured to measure, evaluate, test, and/or determine the temperature inside the injectable substance chamber 44 and/or the temperature of the injectable substance 50. The thermometer can also include a temperature display 62a, which can be located outside of the cover 48 such that the temperature display 62a is configured such that a user can read and/or determine the temperature on the display 62a without opening the lid 18. A speaker 24 can emit a sound to warn the user if a temperature inside the storage system 11 exceeds a predetermined temperature threshold or falls below a predetermined temperature threshold.

As explained in U.S. Nonprovisional patent application Ser. No. 14/849,884, a computer 76, a display 62b, and/or a speaker 24 can warn the user if a temperature, such as the temperature of the first chamber, an injectable substance, a medicine, and/or a thermal bank, deviates outside of a predetermined temperature range, which can be greater than 55 degrees Fahrenheit and/or less than 90 degrees Fahrenheit (such that the system is configured to warn the user prior to a portion of the system reaching a temperature that could harm the medicine stored by the system).

Some embodiments include an insulated container configured to maintain injectable substances at approximately room temperature. In several embodiments, the insulated container can include a chamber configured to hold an injectable substance. The chamber can be surrounded by a substance with high heat capacity. The substance with high heat capacity can be surrounded by an insulated cover.

FIG. 84 illustrates multiple remote computing devices. The storage system 700m can be communicatively coupled with a first remote computing device 76a such that the first remote computing device 76a can receive temperature information from the storage system 700m and/or separation alerts regarding the storage system 700m (e.g., the storage system 700m is located too far from the remote computing device 76a). In response to the temperature information or the separate alerts, the first remote computing device 76a can send temperature information or separation alerts to a second remote computing device 76b (which can be a remote computing device of a guardian of the user of the first remote computing device 76a). The first remote computing device 76a can communicate with the second remote computing device 76b via a remote computer system 76c (e.g., a server or a computer located remotely relative to the first remote computing device 76a and the second remote computing device 769b). Dashed arrows in FIG. 84 illustrate example communication between the storage system 700m, remote computing devices 76a, 76b, and a remote computer system 76c.

Knowing the locations of the remote computing device 76a and the storage system 700m can enable the system to know if the remote computing device 76a and the storage system 700m are so far apart that the distance between them is indicative of leaving the storage system 700m behind (e.g., as the user drives away with the remote computing device 76a but without the storage system 700m). If a signal strength (e.g., of Bluetooth communication) between the storage system 700m and the remote computing device 76a falls below a threshold, then the system can determine that the remote computing device 76a and the storage system 700m are so far apart that the distance between them is indicative of leaving the storage system 700m behind.

Methods of storing a medicine can include obtaining a storage system comprising a phase change system, a first insulated container configured to hold at least a portion of the phase change system, and a first chamber located within the first insulated container. The storage system can be any of the storage systems incorporated by reference and/or described herein. For example, U.S. Nonprovisional patent application Ser. No. 14/849,884, which is incorporated by reference herein, includes many storage systems such as storage systems 10, 11, 12, 200, 200a, 200b, 200c, 200d, 200e, 200f, 200g, 200h, 200i, 300, 400, 500. Many different types of storage systems are described herein such as storage systems 700, 700a, 700b, 700d, 700e, 700f, 700h, 700i, 700k, 700m. Other storage systems described herein and/or incorporated by reference can also be used with the methods described herein and/or incorporated by reference.

The first chamber can be configured to hold the medicine (e.g., an EpiPen, other medicines described herein and/or incorporated by reference). The phase change system can comprise a first phase change material and a second phase change material. The first phase change material can have a first melting temperature greater than 40 degrees Fahrenheit and less than 74 degrees Fahrenheit. The second phase change material can have a second melting temperature greater than 74 degrees Fahrenheit and less than 100 degrees Fahrenheit.

Methods can include placing the medicine in the first chamber; storing the storage system for a period of time in a first environment having a first temperature greater than the first melting temperature and less than the second melting temperature; and/or protecting the medicine from a first external temperature less than the first melting temperature and from a second external temperature greater than the second melting temperature by utilizing phase changes of the first phase change material and the second phase change material to regulate a temperature of the medicine.

Storage systems can include instructions that help users (e.g., customers, caregivers) to know how to use the storage systems. Manufacturers have many different means of delivering these instructions to users. For example, the storage system can have written instructions (e.g., printed on an external portion of the container or lid). Storage systems can be shipped and/or put on store shelves in packaging configured to protect the storage system from shipping damage and/or to help promote key benefits to customers. The packaging can be a box, a clamshell, and/or any other suitable packaging. The packaging can include a paper with printed instructions and/or a booklet with printed instructions.

In some cases, the instructions are printed on a paper that the manufacturer places inside the storage system (e.g., in the first chamber). This helps keep the instructions with the storage system and provides a natural place for the user to find the instructions when she opens the storage system (e.g., by removing the lid).

In some cases, the manufacturer creates a website with the instructions or a video with the instructions. The manufacturer can associate the website information or the video with the storage system by labeling the website information or video with information that helps the user understand that the information or video relates to the storage system. The storage system and/or packaging of the storage system can include a Quick Response ("QR") Code that enables users to access digital instructions associated with the storage system. As used herein, digital instructions are electronic instructions provided to users via the Internet and/or computing devices. Embodiments of digital instructions include videos, websites, audio files, "apps," and images on electronic displays.

Some embodiments comprise storing the storage system in the first environment until the first phase change material is liquid and the second phase change material is solid in response to receiving a first instruction, comprising the period of time, from at least one of the storage system, packaging of the storage system, written instructions included with the storage system, and digital instructions associated with the storage system.

Several embodiments comprise receiving a first instruction and a second instruction from at least one of the storage system, packaging of the storage system, written instructions included with the storage system, and digital instructions associated with the storage system; moving the storage system to a second environment that is cooler than the first and second melting temperatures, and then, in response to the first instruction, moving the storage system to a third environment. The third environment can have a third temperature that is greater than the first melting temperature and less than the second melting temperature. The first instruction can comprise a first recommended maximum time (e.g., at least 3 hours and less than 24 hours) that the storage system can be in the second environment before being moved to the third environment.

Some embodiments comprise moving the storage system to a fourth environment that is warmer than the first and second melting temperatures, and then, in response to the second instruction, moving the storage system to a fifth environment. The fifth environment can have a fifth temperature greater than the first melting temperature and less than the second melting temperature. The second instruction can comprise a second recommended maximum time (e.g., at least 3 hours and less than 24 hours) that the storage system can be in the fourth environment before being moved to the fifth environment.

The first environment, the third environment, and/or the fifth environment can be the same environment in the same location and/or building. The first environment, the third environment, and/or the fifth environment can be different environments in different locations and/or in different buildings.

In several embodiments, the period of time is configured such that the first phase change material is liquid and the second phase change material is solid. Methods can include storing the storage system in an environment (having a temperature greater than the first melting temperature and less than the second melting temperature) until the first phase change material is liquid and the second phase change material is solid.

In some embodiments, maintaining an internal temperature that is close to a melting temperature of a phase change material is enabled by creating a system that can absorb and/or release heat as quickly as heat enters and/or leaves the storage system.

Embodiments can comprise configuring the storage system such that, after being in a first air having a first air temperature of 100 degrees Fahrenheit for one hour, a first rate at which a first heat enters the storage system is within ten percent of a second rate at which a second heat is absorbed by a first phase change of the second phase change material; and/or configuring the storage system such that, after being in a second air having a second air temperature of 32 degrees Fahrenheit for one hour, a third rate at which a third heat leaves the storage system is within ten percent of a fourth rate at which a fourth heat is released by a second phase change of the first phase change material. These configuring elements can be performed by coupling a lid to an insulated container such that a seal reduces heat transfer in and/or out of the storage system.

Storage systems can monitor an internal temperature and then send an alert to the user in response to an internal temperature that is indicative of potential damage to the medicine (e.g., immediate damage or damage in the near future). A storage system can comprise a thermometer configured to measure a temperature of an interior area of the insulated container; and a computing system configured to emit at least one of a visual indicator and an audio indicator in response to at least one of (1) the temperature falling below a predetermined minimum temperature threshold, (2) the temperature rising above a predetermined maximum temperature threshold, (3) falling below a first predetermined amount of time until the temperature is predicted to fall below the predetermined minimum temperature threshold, and (4) falling below a second predetermined amount of time until the temperature is predicted to rise above the predetermined maximum temperature threshold.

Several embodiments comprise moving the storage system to a second environment that is cooler than the first and second melting temperatures, and then moving the storage system to a third environment in response to a first alert emitted by the storage system in response to at least one of (1) an interior temperature of an interior area of the storage system and (2) a duration over which the storage system has been in the second environment. The third environment can have a third temperature that is greater than the first melting temperature and less than the second melting temperature.

Some embodiments include moving the storage system to a fourth environment that is warmer than the first and second melting temperatures, and then moving the storage system to a fifth environment in response to a second alert emitted by the storage system. The fifth environment can have a fifth temperature that is greater than the first melting temperature and less than the second melting temperature.

The first environment, the third environment, and/or the fifth environment can be the same environment in the same location and/or building. The first environment, the third environment, and/or the fifth environment can be different environments in different locations and/or in different buildings.

Several embodiments include moving the storage system to a second environment that is cooler than the first and second melting temperatures, and then moving the storage system to a third environment in response to a first alert emitted by a remote computing device in response to at least one of (1) an interior temperature of an interior area of the storage system and (2) a duration over which the storage system has been in the second environment. The third environment can have a third temperature that is greater than the first melting temperature and less than the second melting temperature.

Some embodiments include moving the storage system to a fourth environment that is warmer than the first and second melting temperatures, and then moving the storage system to a fifth environment in response to a second alert emitted by the remote computing device. The fifth environment can have a fifth temperature that is greater than the first melting temperature and less than the second melting temperature.

Storage systems can send (e.g., directly or indirectly) temperature information to remote computing devices (e.g., a smartphone, a laptop computer, a desktop computer, a server). Several embodiments include measuring, by the storage system, an interior temperature of an interior area of the storage system, and/or receiving, by a remote computing device, an alert in response to the interior temperature falling below a predetermined minimum temperature threshold. Wireless communication between the storage system and the remote computing device can be enabled by the Internet, cellular communication systems, wireless networks, WiFi, Bluetooth, Low Energy Bluetooth, and/or any other suitable systems or technologies.

Some embodiments comprise measuring a temperature of an interior area of the storage system; sending, wirelessly, temperature data comprising the temperature to a remote computing device, and/or displaying, on the remote computing device, the temperature. For example, the remote computing device can display the temperature on a screen of the remote computing device.

A common challenge with emergency medicines is leaving them behind. For example, a person packing for a hike might forget to put her EpiPen in her backpack. Some embodiments include means to remind her that she has left her EpiPen behind. Systems can sense that she has left her EpiPen behind by, for example, sensing a deteriorating communication strength between the remote computing device and the storage system; knowing the location of the remote computing device (e.g., via GPS) and knowing the location of the storage system (e.g., via GPS); losing direct wireless communication between the remote computing device and the storage system; and/or sensing that the storage system is communicatively coupled to a wireless network of a building, but determining that the remote computing device is no longer communicatively coupled to the wireless network of the building.

Some embodiments comprise communicatively coupling the storage system with a first remote computing device via wireless communication (e.g., Bluetooth, WiFi), and/or receiving, by the first remote computing device, a first alert in response to communicatively uncoupling the storage system from the first remote computing device, wherein the communicatively uncoupling is in response to at least one of moving the first remote computing device away from the storage system and moving the storage system away from the first remote computing device. The first alert can cause the first remote computing device to display information regarding the storage system. The information can be a notification that the storage system has been left behind, a location of the storage system, and/or a reminder to acquire the storage system.

Communicatively coupling does not have to comprise continuous communication. Many wireless communication protocols comprise intermittent communication. Communicatively coupling can comprise at least one of intermittent communication and continuous communication.

Several embodiments comprise communicatively coupling a first remote computing device with a first wireless network; communicatively coupling the storage system with the first wireless network; and receiving, by the first remote computing device, a first alert in response to communicatively uncoupling the first remote computing device from the first wireless network while the storage system is communicatively coupled to the first wireless network. For example, a storage system and a remote computing device can be communicatively coupled to a WiFi network of a building. Driving away from the building with the remote computing device (but without the storage system) can uncouple the remote computing device from the WiFi network while the storage system is still communicatively coupled to the WiFi network.

Some embodiments comprise receiving, by a first remote computing device, a first alert in response to increasing a distance between the first remote computing device and the storage system. For example, if a person with the first remote computing device walks home from school while leaving the storage system at school, the distance between the first remote computing device and the storage system increases. The distance also increases if the person walks home from school with her storage system while leaving the remote computing device at school.

Several embodiments comprise communicatively coupling the first remote computing device with the storage system (e.g., directly or indirectly via servers or other items).

Several embodiments comprise communicatively coupling the first remote computing device with a remote computer system, and communicatively coupling the storage system with the remote computer system such that the remote computer system is configured to detect increasing the distance between the first remote computing device and the storage system. The remote computer system can be a server or other computer that is located remotely relative to both the storage system and the remote computing device.

Some embodiments comprise sending, by the first remote computing device, a second alert to a second remote computing device in response to the first remote computing device receiving the first alert. Sending, by the first remote computing device, to the second remote computing device can be indirect or direct. For example, the first remote computing device can send the second alert to the second remote computing device via cellular systems, the Internet, telephonic systems, Bluetooth, WiFi, and/or any suitable systems.

In several embodiments, the first remote computing device is used by a person, and the second remote computing device is used by a guardian of the person. Embodiments can comprise alerting the guardian of the person in response to increasing the distance between the first remote computing device and the storage system.

Some embodiments comprise receiving, by a first remote computing device, a first alert in response to increasing a distance between the first remote computing device and the storage system such that the distance is greater than a distance threshold. In several embodiments, the distance threshold is at least 20 feet and/or less than 200 feet; at least 10 feet and/or less than 500 feet; at least 50 feet and/or less than 600 feet; at least 300 feet and/or less than 1,000 feet; and/or at least 20 feet and/or less than 2,000 feet.

The circumstances surrounding an emergency in which a person needs the medicine in a storage system can be traumatic. For example, during anaphylactic shock, a person may struggle to breathe. This situation can cause people, including family members and caregivers, to panic. In such high-intensity emergencies, some people might not be able to think clearly enough or act quickly enough to find the storage system. Emitting sounds from a speaker of the storage system can help people quickly find the storage system during an emergency.

Some embodiments comprise coupling, communicatively, the storage system to a remote computing device; sending, by the remote computing device, a wireless communication to the storage system; receiving, by the storage system, the wireless communication; and/or emitting, in response to receiving the wireless communication, a sound from the storage system. The sound can be configured to enable a person to find the storage system. The sounds can be at least 60 decibels, at least 75 decibels, and/or less than 140 decibels. The sound can comprise words, beeps, music, and/or any suitable noise.

Some embodiments comprise detecting, by the storage system, a first sound; and emitting, by the storage system, a second sound in response to detecting the first sound. The second sound can be configured to enable a person to find the storage system. The first sound can be a person saying a keyword (e.g., "EpiPen") that the storage system recognizes as indicating that the person wants the storage system to emit the second sound.

One advantage of some embodiments is they can automatically "reset" themselves to a first state without requiring electricity from a power outlet or batteries. (In the first state, the first phase change material is at least partially liquid and the second phase change material is at least partially solid.) As a result, the user does not have to remember extra "steps" to get the storage system ready for another period in hot or cold temperatures.

Some methods include obtaining a storage system comprising a phase change system, a first insulated container configured to hold at least a portion of the phase change system, and a first chamber located within the first insulated container. The first chamber can be configured to hold the medicine. The phase change system can comprise a first phase change material and a second phase change material. The first phase change material can have a first melting temperature greater than 40 degrees Fahrenheit and less than 74 degrees Fahrenheit. The second phase change material can have a second melting temperature greater than 74 degrees Fahrenheit and less than 100 degrees Fahrenheit. Embodiments can comprise placing the medicine in the first chamber.

Several embodiments comprise placing the storage system in a first state by storing the storage system for a period of time in a first environment having a first temperature greater than the first melting temperature and less than the second melting temperature. In the first state, the first phase change material is liquid and the second phase change material is solid.

Several embodiments comprise placing the storage system in a second state by moving the storage system to a second environment having a second temperature less than the first and second melting temperatures. In the second state, the first phase change material is at least partially solid (and/or completely solid) and the second phase change material is solid. Several embodiments comprise then resetting the storage system to the first state by moving the storage system to a third environment having a third temperature greater than the first melting temperature and less than the second melting temperature.

Some embodiments comprise placing the storage system in a third state by moving the storage system to a fourth environment having a fourth temperature greater than the first and second melting temperatures. In the third state, the first phase change material is liquid and the second phase change material is at least partially liquid (and/or completely liquid). Some embodiments comprise then resetting the storage system to the first state by moving the storage system to a fifth environment having a fifth temperature greater than the first melting temperature and less than the second melting temperature.

Any of the embodiments described herein can be used with any medicine. Some embodiments are used to protect insulin from hot or cold temperatures that could damage the insulin. Insulin is often refrigerated, but freezing the insulin can ruin the insulin. Insulin can sometimes last for several weeks in a temperature between 59 degrees Fahrenheit and 86 degrees Fahrenheit, but insulin should not be stored at a temperature above 86 degrees Fahrenheit. Many embodiments provide protection against the danger of freezing insulin and provide protection against the danger of the insulin's temperature rising above 86 degrees Fahrenheit. In several embodiments, this protection may last until a phase change is complete.

Several embodiments comprise a phase change system having a first PCM (with a melting temperature greater than 59 degrees Fahrenheit and less than 74 degrees Fahrenheit) and a second PCM (with a melting temperature greater than 74 degrees Fahrenheit and less than 86 degrees Fahrenheit). These embodiments can guard against temperatures above and below typical room temperatures.

Some embodiments utilize unique phase change systems to create an internal storage environment that is close to typical refrigeration temperatures. These embodiments are sometimes stored in refrigerators to "reset" the phase change materials to a state in which a first phase change material is liquid and a second phase change material is solid. In some embodiments, the melting temperature of the first phase change material is less than typical refrigeration temperatures and the melting temperature of the second phase change material is greater than typical refrigeration temperatures. As a result, the medicine storage system can provide protection from temperatures below 32 degrees Fahrenheit (e.g., if the storage system is taken from the refrigerator into an environment that is below 32 degrees Fahrenheit) and can provide protection from temperatures above 86 degrees Fahrenheit (e.g., if the storage system is taken from the refrigerator into an environment that is above 86 degrees Fahrenheit).

Even though insulin is often stored in a refrigerator (for long-term storage), insulin can be kept at room temperature for short periods of time. Thus, some embodiments utilize unique phase change systems to create an internal storage environment that is close to typical room temperatures (rather than close to typical refrigerator temperatures). These embodiments are sometimes stored at room temperature to "reset" the phase change materials to a state in which a first phase change material is liquid and a second phase change material is solid.

As shown by many figures herein and/or incorporated by reference, a medicine storage system can be configured to protect a medicine from a first external temperature less than a minimum recommended storage temperature and from a second external temperature greater than a maximum recommended storage temperature by utilizing phase changes to regulate a temperature of the medicine. Medicine storage systems can comprise an insulated container; a first chamber located inside the insulated container, wherein the first chamber is configured to hold a removable medicine container; and a phase change system comprising a second chamber having a first phase change material and comprising a third chamber having a second phase change material. The phase change system can be located inside the insulated container. The first phase change material can have a first melting temperature greater than 33 degrees Fahrenheit and less than 74 degrees Fahrenheit. The second phase change material can have a second melting temperature less than 100 degrees Fahrenheit, greater than the first melting temperature, and/or at least four degrees greater than the first melting temperature.

In some cases, refrigerators have a temperature of about 36 degrees Fahrenheit to about 46 degrees Fahrenheit. Thus, the first melting temperature can be less than 36 degrees Fahrenheit and the second melting temperature can be greater than 46 degrees Fahrenheit such that the system comprises one liquid PCM and one frozen PCM regardless of what the actual refrigerator temperature is within the range of 36 degrees Fahrenheit to 46 degrees Fahrenheit. The second melting temperature can be greater than 74 degrees Fahrenheit.

As used herein, "refrigerator" is used in the ordinary sense to mean a device that is used to keep things (such as food and drinks) cold.

Some medicine storage systems are stored in refrigerators to "reset" the PCMs. The first melting temperature can be less than 40 degrees Fahrenheit, and the second melting temperature can be greater than 40 degrees Fahrenheit such that the medicine storage system is configurable for storage in a refrigerator, preventing the medicine from freezing, and preventing the medicine from becoming hotter than 100 degrees Fahrenheit.

In some embodiments, the medicine storage system is configured to keep the medicine well below 100 degrees Fahrenheit, which can be especially advantageous for insulin. The second melting temperature can be less than 65 degrees Fahrenheit (e.g., to keep the medicine cool relative to an external environment that is greater than 74 degrees Fahrenheit and to keep the medicine closer to typical refrigeration temperatures than would be the case with a second melting temperature between 74 degrees Fahrenheit and 100 degrees Fahrenheit).

The removable medicine container can be located inside the first chamber. The removable medicine container can comprise insulin, epinephrine, adrenaline, and/or any other medicine.

The insulated container can comprise an opening to the first chamber. The opening can be covered by a removable lid. The medicine storage system can be configured such that removing the lid enables a user to remove the medicine container from the first chamber.

As shown by many of the figures, the opening is not in fluid communication with the second chamber, and the first phase change material is fully enclosed by the second chamber such that removing the lid does not permit the first phase change material to spill out of the medicine storage system. The opening is not in fluid communication with the third chamber, and the second phase change material is fully enclosed by the third chamber such that removing the lid does not permit the second phase change material to spill out of the medicine storage system.

In some embodiments the medicine storage system comprises a first vacuum chamber located between walls of the insulated container such that the first vacuum chamber insulates the insulated container. The insulated container can comprise an opening to the first chamber. The opening can be covered by a removable lid. The medicine storage system can be configured such that removing the lid enables a user to remove the medicine container from the first chamber. The lid can comprise a second vacuum chamber configured such that screwing the lid into the opening rotates the second vacuum chamber relative to the first chamber system.

The first chamber can comprise many different compartments. Each compartment can be configured to hold at least one medicine case (e.g., an EpiPen, an insulin bottle, an insulin injection device, a plastic pill bottle, a container that holds medicine). For example, FIG. 17 of U.S. Nonprovisional patent application Ser. No. 14/849,884 (which is incorporated by reference herein) illustrates a medicine storage system configured to hold more than one medicine 212. Each compartment can be labeled with patient information. For example, once a person removes a lid of the storage system, paper labels (that are adhered to an interior area next to each compartment) can show the name of the patient to whom the medicine belongs. This approach can be advantageous for schools that prefer to use the particular medicine that belongs to a particular child (rather than a similar medicine that belongs to another child).

The compartments can form a matrix. For example, there can be several rows and several columns of medicines separated by metal or plastic walls. The insulated container can be a Yeti Tundra cooler made by YETI Coolers LLC having an office in Austin, Tex. The first and second phase change materials can be placed inside the cooler to provide bidirectional temperature protection.

Methods of storing a medicine can comprise obtaining a medicine storage system comprising a phase change system, a first insulated container configured to hold at least a portion of the phase change system, and a first chamber located within the first insulated container. The first chamber can be configured to hold the medicine. The phase change system can comprise a first phase change material and a second phase change material. The first phase change material can have a first melting temperature greater than 33 degrees Fahrenheit and less than 74 degrees Fahrenheit. (This 33 degree Fahrenheit cutoff can be advantageous because it is greater than the freezing temperature of insulin and less than typical temperatures of refrigerators. In some embodiments, the first phase change material can have a first melting temperature of greater than 33 degrees Fahrenheit plus or minus one or two degrees.) The second phase change material can have a second melting temperature less than 100 degrees Fahrenheit and at least four degrees greater than the first melting temperature.

Several embodiments comprise placing the medicine in the first chamber, and storing the storage system for a period of time in a first environment having a first temperature greater than the first melting temperature and less than the second melting temperature.

Some embodiments comprise protecting the medicine from a first external temperature less than the first melting temperature and from a second external temperature greater than the second melting temperature by utilizing phase changes of the first phase change material and the second phase change material to regulate a temperature of the medicine.

In several embodiments, the first melting temperature is less than 40 degrees Fahrenheit, and the second melting temperature is greater than 40 degrees Fahrenheit. Methods can comprise storing the medicine storage system in a refrigerator such that the first phase change material is liquid and the second phase change material is solid.

Several methods of storing a medicine comprise obtaining a medicine storage system comprising a phase change system, a first insulated container configured to hold at least a portion of the phase change system, and a first chamber located within the first insulated container. The first chamber can be configured to hold the medicine. The phase change system can comprise a first phase change material and a second phase change material. The first phase change material can have a first melting temperature greater than 33 degrees Fahrenheit and less than 40 degrees Fahrenheit. The second phase change material can have a second melting temperature greater than 40 degrees Fahrenheit and less than 100 degrees Fahrenheit.

Some embodiments comprise placing the medicine in the first chamber, and placing the storage system in a first state by storing the storage system in a first refrigerated area for a period of time. In the first state, the first phase change material is liquid and the second phase change material is solid.

Several embodiments comprise placing the storage system in a second state by moving the storage system to a second environment having a second temperature less than the first and second melting temperatures, wherein in the second state the first phase change material is at least partially solid and the second phase change material is solid, and then resetting the storage system to the first state by placing the storage system in a second refrigerated area.

Some embodiments comprise placing the storage system in a third state by moving the storage system to a third environment having a third temperature greater than the first and second melting temperatures, wherein in the third state the first phase change material is liquid and the second phase change material is at least partially liquid, and then resetting the storage system to the first state by placing the storage system in a third refrigerated area.

The first, second, and third refrigerated areas can be in different refrigerators. However, the first, second, and third refrigerated areas can do not have to be in different refrigerators. The first, second, and third refrigerated areas can be the same area in a single refrigerator.

Referring now to FIG. 3, storage systems can include an outer case, which can be made of plastic, metal, insulation, and/or any suitable material. The storage system can include a vacuum chamber 708 (e.g., in a vacuum flask). The inner wall 710 can be a first flask. The outer wall 712 can be a second flask. The first and second flasks can form a vacuum flask. The vacuum flask can be located inside the outer case such that the outer case can be configured to protect the vacuum flask from damage such as denting or cracking. The vacuum flask can comprise an inner wall 710 and an outer wall 712 with a gas pressure between the inner wall and the outer wall that is less than atmospheric pressure. In some embodiments, the pressure between the inner wall and the outer wall can be less than 60% of atmospheric pressure, less than 40% of atmospheric pressure, or less than 20% of atmospheric pressure. The atmospheric pressure can be measured at sea level. The vacuum flask can include a first flask placed inside a second flask. The first flask and the second flask can be joined at the neck 722 such that the area between the first flask and the second flask is hermetically sealed from the air outside of the area between the first flask and the second flask. The vacuum flask can be made of metal, glass, foam, and/or plastic.

Many embodiments include a phase change system having multiple phase change materials (e.g., one, two, three, four, or more phase change materials with unique melting temperatures). The multiple phase change materials can provide protection from temperatures above and below room temperatures. Thus, one system can shield medicine from temperature variations in both directions without requiring previous knowledge of whether a person will bring the storage system into hot or cold weather.

One way to build a storage system that resists temperature decreases and increases is to include two phase change materials inside the thermal bank. The first phase change material can resist temperature decreases due to cold outside environments. The second phase change material can resist temperature increases due to hot outside environments.

The first phase change material can have a high heat of fusion to enable a relatively lightweight system that can still provide sufficient resistance to temperature changes. The first phase change material can release large amounts of heat before allowing the temperature inside the first chamber to decrease. For example, the first phase change material can release large amounts of heat (per gram of the material) as the material changes from a liquid to a solid. The melting temperature of the first phase change material can be less than 70 Fahrenheit (e.g., just below room temperature) and greater than the minimum recommended medicine storage temperature.

For example, if a manufacturer of a medicine recommends a minimum storage temperature of 45 degrees Fahrenheit, then the first phase change material can be selected with a melting temperature between 45 degrees Fahrenheit and around 70 degrees Fahrenheit (e.g., below a room temperature). Thus, when a temperature inside the insulated container goes below the melting point, the first phase change material releases large amounts of heat before allowing the temperature inside the first chamber to significantly decrease. As a result, the first phase change material dramatically prolongs the time required to decrease the temperature inside the first chamber below the minimum storage temperature.

This additional time can enable the medicine to remain outside much longer without reducing the efficacy of the medicine than would be the case without the storage system. Moreover, the phase change enables the storage system to be much more compact than would be the case with a storage system that only uses water to resist temperature changes (at temperatures above 32 degrees Fahrenheit).

The second phase change material of the storage system can resist temperature increases due to hot outside environments. The second phase change material can have a high heat of fusion and a melting temperature that is greater than room temperature and less than the maximum recommended medicine storage temperature. For example, if the maximum recommended storage temperature is 85 degrees Fahrenheit, then in some embodiments, the second phase change material can have a melting temperature between 80 degrees Fahrenheit and 85 degrees Fahrenheit. Thus, the second phase change material can absorb a large amount of heat (to melt) before the second phase change material would allow the temperature inside the storage system to increase significantly above the melting temperature of the second phase change material.

The rate of heat transfer between the outside environment 30 and the first chamber (e.g., the void 154) is reduced by reducing the temperature difference between the outside environment and the thermal bank 140 (during melting or solidifying). Thus, phase change materials can be selected that have a melting point near the minimum storage temperature (e.g., without being less than the minimum storage temperature) or near the maximum storage temperature (e.g., without being greater than the maximum storage temperature). (The minimum and maximum storage temperatures can be recommended by the manufacturer of the medicine and are often included with literature provided with the medicine.) "Near the minimum" or "near the maximum" can be within 10 degrees Fahrenheit.

Many different materials can be suitable phase change materials as long as the materials have a melting temperature within the target range (as explained above). Entropy Solutions, Inc. has an office in Plymouth, Minn. and provides a wide range of suitable phase change materials under the brand name PureTemp. Climator Sweden AB sells a wide range of phase change materials under the brand name ClimSel. Examples of phase change materials include sodium sulfate, trimethylolethane combined with water, $Mn(NO_3)_2.6H_2O+MnCl_2.4H_2O$, $NaCl.Na_2SO_4.10H_2O$, paraffin 16-carbons, and paraffin 18-carbons.

In several embodiments, phase change materials spontaneously melt and/or solidify in response to temperature (without requiring an additional activation step). For example, just a drop in temperature below a melting temperature can cause a spontaneous phase change material to freeze. Just a rise in temperature above a melting temperature can cause a spontaneous phase change material to solidify.

The phase change materials are not the only part of the system that reduces the rate of temperature change inside the first chamber (e.g., the void 154). An insulated container can reduce the rate of heat transfer. Some embodiments include a vacuum flask. Thermos L.L.C. manufactures a wide range of vacuum flasks. The vacuum is a type of insulation.

Walls of vacuum flasks can be made of glass, stainless steel, or any other suitable material. Many components can be molded plastic.

Insulated containers can have rigid walls or compliant, flexible walls. For example, the insulated container can be a steel Thermos or an insulated, fabric pouch.

Storage systems can use many different types of insulation including multi-layer insulation, closed-cell insulation, closed-cell foam insulation, rubber foam insulation, nitrile rubber foam insulation, nitrile butadiene rubber insulation, polyurethane insulation, reflective foil layers, injected insulation, rigid insulation, flexible insulation, and/or vacuum insulation.

Some embodiments use a first vacuum flask inside a second vacuum flask to form a dual-vacuum layer system. The flask can include reflective walls to reduce heat transfer by radiation.

In several embodiments, the interior of the vacuum flask is cylindrical. The chambers that hold the phase change system plus the first chamber can form a cylindrical shape that is tailored to the interior of the vacuum flask. The phase change system can have a compliant external housing with an outer diameter that is larger than the diameter of an opening to the vacuum flask. The compliant external housing (e.g., a compliant perimeter) can enable pressing the phase change system into the vacuum flask in spite of the outer diameter of the external housing being larger than the diameter of the opening to the vacuum flask.

In several embodiments, storage systems include an insulated container comprising a base and an opening configurable to enable removing a medicine from inside the insulated container; a first chamber located inside the insulated container, wherein the first chamber is configured to hold the medicine; a first phase change material located inside the insulated container; and/or a second phase change material located inside the insulated container.

In some embodiments, the first phase change material can have a first melting temperature greater than 40 degrees Fahrenheit and less than 74 degrees Fahrenheit. The second phase change material can have a second melting temperature greater than 74 degrees Fahrenheit and less than 100 degrees Fahrenheit. The first melting temperature can be at least four degrees Fahrenheit less than the second melting temperature. For example, 74 degrees Fahrenheit can be approximately equal to a typical room temperature (although room temperatures commonly vary in rooms having temperature controlled environments enabled by heating and/or air conditioning).

Using a "temperature dividing line" of 74 degrees Fahrenheit helps enable some embodiments to avoid inappropriately triggering melting and/or freezing while the storage system is located in a temperature controlled room. Imagine if the second phase change material had a melting temperature of less than 74 degrees. As a result, the second phase change material could completely melt before a person even moved the storage system from a room temperature into a hot environment that is warmer than a maximum recommended storage temperature of the medicine. In this case the phase change of the second phase change material would not help reduce the rate of temperature rise inside the first chamber in response to heat transfer caused by the hot environment. Similarly, this "temperature dividing line" helps ensure that the first phase change material will have a sufficiently low melting temperature such that the first phase change material should not solidify before the storage system is moved from a room temperature to an environment that is colder than a minimum recommended storage temperature.

The "temperature dividing line" can vary based on what medicine the storage system will hold. For example, some medicine manufacturers recommend refrigerating certain medicines. In several embodiments, the temperature dividing line is 36 degrees Fahrenheit. Thus, the first phase change material can have a melting temperature above 0 degrees Fahrenheit and/or below 36 degrees Fahrenheit. The second phase change material can have a melting temperature above 36 degrees Fahrenheit and/or below 50 degrees Fahrenheit.

A "target temperature" can be a "temperature dividing line." In several embodiments, the target temperature can be 74 degrees Fahrenheit (e.g., when the manufacturer recommends storing a medicine at room temperature). In several embodiments, the target temperature can be 36 degrees Fahrenheit (e.g., when the manufacturer recommends refrigerating a medicine).

In some embodiments, the storage system is configured to cause the first phase change material to solidify when a first temperature of the first chamber falls below the first melting temperature, and/or the storage system is configured to cause the second phase change material to melt when the first temperature of the first chamber rises above the second melting temperature. As a result, the storage system can be configured to temporarily protect the medicine from a first environment that is colder than a safe minimum storage temperature and/or from a second environment that is hotter than a safe maximum storage temperature. Manufacturers of medicines can recommend minimum storage temperatures and/or maximum storage temperatures for medicines.

In several embodiments, the first phase change material has a first latent heat of at least 40 kJ/kg, and/or the second phase change material has a second latent heat of at least 40 kJ/kg. In some embodiments, the first phase change material has a first latent heat of at least 110 kJ/kg, and/or the second phase change material has a second latent heat of at least 110 kJ/kg. In several embodiments, the first phase change material has a first latent heat of at least 180 kJ/kg, and/or the second phase change material has a second latent heat of at least 180 kJ/kg. These latent heat properties can dramatically reduce the necessary size of the phase change materials, which enables dramatically reducing the overall volume of the storage system.

The chambers of a storage system can include different phase chamber materials. The phase change system can have more than two melting temperatures. In some embodiments, a second chamber contains a first phase change material having a first melting temperature; a third chamber contains a second phase change material having a second melting temperature; a fourth chamber contains a third phase change material having a third melting temperature; and a fifth chamber contains a fourth phase change material having a fourth melting temperature. The first and second melting temperatures can be less than a target temperature (e.g., 74 degrees Fahrenheit), and the first melting temperature can be less than (e.g., at least 3 degrees Fahrenheit less than) the second melting temperature. The third and fourth melting temperatures can be greater than the target temperature, and the third melting temperature can be less than (e.g., at least 3 degrees Fahrenheit less than) the fourth melting temperature.

A phase change system with more than two melting temperatures can provide additional temperature protection reliability. For example, a third phase change material can protect against temperatures that are just slightly above a target temperature (e.g., 74 degrees Fahrenheit, 36 degrees Fahrenheit). Thus, the system can protect against even minor temperature variations above the target temperature. However, phase change materials that protect against temperatures that are just slightly above a target temperature are susceptible to changing phase while the storage system is located indoors.

For example, a manufacturer can recommend a maximum EpiPen storage temperature of 77 degrees Fahrenheit, which is very close to typical room temperatures. The phase change system can include a third phase change material with a melting temperature of 76 degrees Fahrenheit. If the storage system is kept in a room that is below 76 degrees Fahrenheit for at least enough time for the third phase change material to solidify, then once the storage system is moved into an outdoor environment that is 79 degrees Fahrenheit, the third phase change material will begin protecting the EpiPen from the outdoor environment that is 79 degrees Fahrenheit.

However, if the storage system is kept in a room that is 78 degrees Fahrenheit for at least enough time for the third phase change material to melt, then once the storage system is moved into an outdoor environment that is 80 degrees Fahrenheit, the third phase change material will fail to protect the EpiPen from the outdoor environment that is 80 degrees Fahrenheit (because the phase change will have occurred before the storage system reaches the outdoor environment). In this case, having a fourth phase change material can be helpful. The fourth phase change material can have a fourth melting temperature that is not as close to typical room temperatures. For example, the fourth melting temperature can be 82 degrees Fahrenheit, which is typically higher than room temperatures. Thus, the fourth phase change material would not be melting while kept in a room that is 78 degrees Fahrenheit for at least enough time for the third phase change material to melt. Then, once the storage system is moved into an outdoor environment that is 80 degrees Fahrenheit, the fourth phase change material will protect the EpiPen from the outdoor environment that is 80 degrees Fahrenheit (by melting).

A manufacturer of a medicine can recommend a minimum storage temperature and a maximum storage temperature for the medicine. In some embodiments, the storage system includes a first phase change material with a first melting temperature that is lower than the target temperature and lower than the minimum storage temperature; the storage system includes a second phase change material with a second melting temperature that is lower than the target temperature, higher than the minimum storage temperature, and higher than the first melting temperature; the storage system includes a fourth phase change material with a fourth melting temperature that is higher than the target temperature and higher than the maximum storage temperature; and/or the storage system includes a third phase change material with a third melting temperature that is higher than the target temperature, lower than the maximum storage temperature, and lower than the fourth melting temperature.

Several phase change system embodiments include two different melting temperatures below a target temperature (e.g., 74 degrees Fahrenheit) and one melting temperature above the target temperature. Some phase change system embodiments include two different melting temperatures above a target temperature (e.g., 74 degrees Fahrenheit) and one melting temperature below the target temperature.

If a difference between a target temperature and an expected cold outdoor temperature is greater than a difference between the target temperature and an expected hot outdoor temperature, then the phase change system can include two different melting temperatures below the target temperature and one melting temperature above the target temperature.

If a difference between a target temperature and an expected hot outdoor temperature is greater than a difference between the target temperature and an expected cold outdoor temperature, then the phase change system can include two different melting temperatures above the target temperature and one melting temperature below the target temperature.

The expected cold outdoor temperature is less than the target temperature. The expected hot outdoor temperature is greater than the target temperature. The expected cold outdoor temperature can be the maximum expected cold outdoor temperature. The expected hot outdoor temperature can be the maximum expected hot outdoor temperature.

A manufacturer of a medicine can recommend a minimum storage temperature and a maximum storage temperature for the medicine. If a difference between a target temperature and the minimum storage temperature is greater than a difference between the target temperature and the maximum storage temperature, then the phase change system can include two different melting temperatures below the target temperature and one melting temperature above the target temperature.

If a difference between a target temperature and the maximum storage temperature is greater than a difference between the target temperature and the minimum storage temperature, then the phase change system can include two different melting temperatures above the target temperature and one melting temperature below the target temperature.

If a difference between the minimum storage temperature and the expected cold outdoor temperature is greater than a difference between the maximum storage temperature and the expected hot outdoor temperature, then the phase change system can include two different melting temperatures below the target temperature and one melting temperature above the target temperature.

If a difference between the maximum storage temperature and the expected hot outdoor temperature is greater than a difference between the minimum storage temperature and the expected cold outdoor temperature, then the phase change system can include two different melting temperatures above the target temperature and one melting temperature below the target temperature.

Any of the storage systems shown in the figures, described herein, and/or incorporated by reference can be configured according to the temperature information above and according to the phase change material information described above.

Any of the storage systems shown in the figures, described herein, or incorporated by reference can include three, four, or more phase change materials (e.g., each with different melting temperatures). The chambers described herein can be subdivided into additional chambers by walls to hold phase change materials with different melting temperatures.

In some embodiments in which a first phase change material has a melting temperature greater than 40 degrees Fahrenheit and less than 74 degrees Fahrenheit, the phase change material comprises at least one of PureTemp 6, PureTemp 15, PureTemp 18, and PureTemp 20 made by Entropy Solutions, Inc., which has an office in Plymouth, Minn. In some embodiments where a first phase change material has a melting temperature greater than 40 degrees Fahrenheit and less than 74 degrees Fahrenheit, the phase change material comprises at least one of Paraffin 14-Carbons, Paraffin 15-Carbons, and Paraffin 16-Carbons.

In some embodiments in which a second phase change material has a melting temperature greater than 74 degrees Fahrenheit and less than 100 degrees Fahrenheit, the phase change material comprises at least one of PureTemp 25, PureTemp 27, PureTemp 28, PureTemp 29, and PureTemp 35 made by Entropy Solutions, Inc., which has an office in Plymouth, Minn. In some embodiments where a second phase change material has a melting temperature greater than 74 degrees Fahrenheit and less than 100 degrees Fahrenheit, the phase change material comprises at least one of Paraffin 18-Carbons, Paraffin 19-Carbons, and Paraffin 20-Carbons.

In some embodiments in which a first phase change material has a melting temperature greater than 28 degrees Fahrenheit, greater than 30 degrees Fahrenheit, greater than 32 degrees Fahrenheit, greater than 33 degrees Fahrenheit, greater than 34 degrees Fahrenheit, less than 40 degrees Fahrenheit, and/or less than 74 degrees Fahrenheit, the phase change material comprises at least one of PureTemp −2, PureTemp 1, PureTemp 4. In some embodiments in which a second phase change material has a melting temperature greater than 40 degrees Fahrenheit and less than 100 degrees Fahrenheit, the phase change material comprises at least one of PureTemp 6, PureTemp 8, PureTemp 18, PureTemp 29, and PureTemp 35.

Many embodiments are described herein and/or incorporated by reference to communicate a vast number of features and methods. Describing all of the features and methods in every embodiment would lead to unnecessary redundancy. Each of the features and methods described herein and/or incorporated by reference can be included in each of the embodiments described herein and/or incorporated by reference. Thus, elements of one embodiment can be combined with elements of other embodiments.

Many embodiments described herein and/or incorporated by reference greatly benefit people by enabling them to take their temperature-sensitive medicines outdoors (even in hot or cold weather). Rather than risk being without their medicine (by leaving their medicine behind when going outdoors), the specially constructed storage systems described herein and/or incorporated by reference can protect medicines from damage due to hot and cold weather without requiring the bulky structures or expensive components of traditional refrigerators.

Interpretation

None of the steps described herein and/or incorporated by reference is essential or indispensable. Any of the steps can be adjusted or modified. Other or additional steps can be used. Any portion of any of the steps, processes, structures, and/or devices disclosed or illustrated in one embodiment, flowchart, or example in this specification can be combined or used with or instead of any other portion of any of the steps, processes, structures, and/or devices disclosed or illustrated in a different embodiment, flowchart, or example. The embodiments and examples provided herein are not intended to be discrete and separate from each other.

The section headings and subheadings provided herein are nonlimiting. The section headings and subheadings do not represent or limit the full scope of the embodiments described in the sections to which the headings and subheadings pertain. For example, a section titled "Topic 1" may include embodiments that do not pertain to Topic 1 and embodiments described in other sections may apply to and be combined with embodiments described within the "Topic 1" section.

Some of the devices, systems, embodiments, and processes use computers. Each of the routines, processes, methods, and algorithms described in the preceding sections may be embodied in, and fully or partially automated by, code modules executed by one or more computers, computer processors, or machines configured to execute computer instructions. The code modules may be stored on any type of non-transitory computer-readable storage medium or tangible computer storage device, such as hard drives, solid state memory, flash memory, optical disc, and/or the like. The processes and algorithms may be implemented partially or wholly in application-specific circuitry. The results of the disclosed processes and process steps may be stored, persistently or otherwise, in any type of non-transitory computer storage such as, e.g., volatile or non-volatile storage.

The various features and processes described above may be used independently of one another, or may be combined in various ways. All possible combinations and subcombinations are intended to fall within the scope of this disclosure. In addition, certain method, event, state, or process blocks may be omitted in some implementations. The methods, steps, and processes described herein are also not limited to any particular sequence, and the blocks, steps, or states relating thereto can be performed in other sequences that are appropriate. For example, described tasks or events may be performed in an order other than the order specifically disclosed. Multiple steps may be combined in a single block or state. The example tasks or events may be performed in serial, in parallel, or in some other manner. Tasks or events may be added to or removed from the disclosed example embodiments. The example systems and components described herein may be configured differently than described. For example, elements may be added to, removed from, or rearranged compared to the disclosed example embodiments.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require at least one of X, at least one of Y, and at least one of Z to each be present.

The term "and/or" means that "and" applies to some embodiments and "or" applies to some embodiments. Thus, A, B, and/or C can be replaced with A, B, and C written in one sentence and A, B, or C written in another sentence. A, B, and/or C means that some embodiments can include A and B, some embodiments can include A and C, some embodiments can include B and C, some embodiments can only include A, some embodiments can include only B, some embodiments can include only C, and some embodiments include A, B, and C. The term "and/or" is used to avoid unnecessary redundancy.

While certain example embodiments have been described, these embodiments have been presented by way of example only, and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the inventions disclosed herein.

We claim:

1. A medicine storage system configured to protect a medicine from a first external temperature less than a minimum recommended storage temperature and from a second external temperature greater than a maximum recommended storage temperature by utilizing phase changes to regulate a temperature of the medicine, the medicine storage system comprising:
   an insulated container;
   a first chamber located inside the insulated container, wherein the first chamber is configured to hold a removable medicine container; and
   a phase change system comprising a second chamber having a first phase change material and comprising a third chamber having a second phase change material, wherein the phase change system is located inside the insulated container,
   wherein the first phase change material has a first melting temperature greater than 33 degrees Fahrenheit and less than 74 degrees Fahrenheit, and the second phase change material has a second melting temperature less than 100 degrees Fahrenheit and at least four degrees greater than the first melting temperature.

2. The medicine storage system of claim 1, wherein the second melting temperature is greater than 74 degrees Fahrenheit.

3. The medicine storage system of claim 1, wherein the first melting temperature is less than 40 degrees Fahrenheit, and the second melting temperature is greater than 40 degrees Fahrenheit such that the medicine storage system is configurable for storage in a refrigerator, preventing the medicine from freezing, and preventing the medicine from becoming hotter than 100 degrees Fahrenheit.

4. The medicine storage system of claim 3, wherein the second melting temperature is less than 65 degrees Fahrenheit.

5. The medicine storage system of claim 1, wherein the removable medicine container is located inside the first chamber, and the removable medicine container comprises insulin.

6. The medicine storage system of claim 1, wherein the removable medicine container is located inside the first chamber, and the removable medicine container comprises at least one of epinephrine and adrenaline.

7. The medicine storage system of claim 1, wherein the insulated container comprises an opening to the first chamber, the opening is covered by a removable lid, and the medicine storage system is configured such that removing the lid enables a user to remove the medicine container from the first chamber,
   wherein the opening is not in fluid communication with the second chamber, and the first phase change material is fully enclosed by the second chamber such that removing the lid does not permit the first phase change material to spill out of the medicine storage system, and the opening is not in fluid communication with the third chamber, and the second phase change material is fully enclosed by the third chamber such that removing the lid does not permit the second phase change material to spill out of the medicine storage system.

8. The medicine storage system of claim 1, further comprising a first vacuum chamber located between walls of the insulated container such that the first vacuum chamber insulates the insulated container.

9. The medicine storage system of claim 8, wherein the insulated container comprises an opening to the first chamber, the opening is covered by a removable lid, and the medicine storage system is configured such that removing the lid enables a user to remove the medicine container from the first chamber, and
   wherein the lid comprises a second vacuum chamber configured such that screwing the lid into the opening rotates the second vacuum chamber relative to the first chamber system.

10. The medicine storage system of claim 1, further comprising a liner located in the first chamber, wherein the liner surrounds at least a majority of the removable medicine container, the liner is made from a first material, and the first chamber is made from a second material that is at least two times harder than the first material as measured on the Brinell scale.

11. The medicine storage system of claim 1, wherein the insulated container comprises an opening to the first chamber, the opening is covered by a removable lid, and the medicine storage system is configured such that removing the lid enables a user to remove the medicine container from the first chamber,
   the medicine storage system further comprising a first seal located between the lid and the opening such that the first seal is configured to block fluid from entering the first chamber to keep the medicine container dry, and the first seal is configured to reduce heat transfer from an internal portion of the medicine storage system to an area outside the medicine storage system.

12. The medicine storage system of claim 11, wherein the lid is coupled to the insulated container by screw threads, and the first seal is compressed by inserting a portion of the lid into the opening such that the first seal is compressed between the portion of the lid and a radially inward protrusion of the opening.

13. The medicine storage system of claim 1, wherein the first chamber comprises at least ten compartments, wherein the compartments are configured to hold at least one medicine case.

14. The medicine storage system of claim 13, wherein the compartments form a matrix, and at least some of the compartments are labeled with patient information.

15. The medicine storage system of claim 1, wherein the first melting temperature of the first phase change material is greater than 59 degrees Fahrenheit and less than 74 degrees Fahrenheit, and the second melting temperature of the second phase change material is greater than 74 degrees Fahrenheit and less than 86 degrees Fahrenheit.

16. A method of storing a medicine, the method comprising:
   obtaining a medicine storage system comprising a phase change system, a first insulated container configured to hold at least a portion of the phase change system, and a first chamber located within the first insulated container, wherein the first chamber is configured to hold the medicine, and wherein the phase change system comprises a first phase change material and a second phase change material, the first phase change material having a first melting temperature greater than 33 degrees Fahrenheit and less than 74 degrees Fahrenheit, and the second phase change material having a second melting temperature less than 100 degrees Fahrenheit and at least four degrees greater than the first melting temperature;

placing the medicine in the first chamber;

storing the storage system for a period of time in a first environment having a first temperature greater than the first melting temperature and less than the second melting temperature; and protecting the medicine from a first external temperature less than the first melting temperature and from a second external temperature greater than the second melting temperature by utilizing phase changes of the first phase change material and the second phase change material to regulate a temperature of the medicine.

17. The method of claim 16, wherein the first melting temperature is less than 40 degrees Fahrenheit, and the second melting temperature is greater than 40 degrees Fahrenheit, the method further comprising storing the medicine storage system in a refrigerator such that the first phase change material is liquid and the second phase change material is solid.

18. The method of claim 16, further comprising storing the storage system in the first environment until the first phase change material is liquid and the second phase change material is solid in response to receiving a first instruction, comprising the period of time, from at least one of the storage system, packaging of the storage system, written instructions included with the storage system, and digital instructions associated with the storage system.

19. The method of claim 16, further comprising receiving a first instruction and a second instruction from at least one of the storage system, packaging of the storage system, written instructions included with the storage system, and digital instructions associated with the storage system, moving the storage system to a second environment that is cooler than the first and second melting temperatures, and then, in response to the first instruction, moving the storage system to a third environment, wherein the third environment has a third temperature that is greater than the first melting temperature and less than the second melting temperature, and the first instruction comprises a first recommended maximum time that the storage system can be in the second environment before being moved to the third environment, the method further comprising moving the storage system to a fourth environment that is warmer than the first and second melting temperatures, and then, in response to the second instruction, moving the storage system to a fifth environment, wherein the fifth environment has a fifth temperature greater than the first melting temperature and less than the second melting temperature, and the second instruction comprises a second recommended maximum time that the storage system can be in the fourth environment before being moved to the fifth environment.

20. A method of storing a medicine, the method comprising:

obtaining a medicine storage system comprising a phase change system, a first insulated container configured to hold at least a portion of the phase change system, and a first chamber located within the first insulated container, wherein the first chamber is configured to hold the medicine, and wherein the phase change system comprises a first phase change material and a second phase change material, the first phase change material having a first melting temperature greater than 33 degrees Fahrenheit and less than 40 degrees Fahrenheit, and the second phase change material having a second melting temperature greater than 40 degrees Fahrenheit and less than 100 degrees Fahrenheit;

placing the medicine in the first chamber;

placing the storage system in a first state by storing the storage system in a first refrigerated area for a period of time, wherein in the first state the first phase change material is liquid and the second phase change material is solid;

placing the storage system in a second state by moving the storage system to a second environment having a second temperature less than the first and second melting temperatures, wherein in the second state the first phase change material is at least partially solid and the second phase change material is solid, and then resetting the storage system to the first state by placing the storage system in a second refrigerated area; and placing the storage system in a third state by moving the storage system to a third environment having a third temperature greater than the first and second melting temperatures, wherein in the third state the first phase change material is liquid and the second phase change material is at least partially liquid, and then resetting the storage system to the first state by placing the storage system in a third refrigerated area.

21. The method of claim 20, wherein the first, second, and third refrigerated areas are located in a single refrigerator.

* * * * *